(12) United States Patent
Gore et al.

(10) Patent No.: US 7,439,360 B2
(45) Date of Patent: Oct. 21, 2008

(54) VANILLOID RECEPTOR LIGANDS AND THEIR USE IN TREATMENTS

(75) Inventors: Vijay Keshav Gore, Thousand Oaks, CA (US); Vu Van Ma, Simi Valley, CA (US); Mark H. Norman, Thousand Oaks, CA (US); Vassil I. Ognyanov, Thousand Oaks, CA (US); Ning Xi, Thousand Oaks, CA (US)

(73) Assignee: AMGEN Inc., Thousand Oaks, CA (US)

( * ) Notice: Subject to any disclaimer, the term of this patent is extended or adjusted under 35 U.S.C. 154(b) by 0 days.

(21) Appl. No.: 11/251,445

(22) Filed: Oct. 14, 2005

(65) Prior Publication Data

US 2006/0084640 A1 Apr. 20, 2006

Related U.S. Application Data

(60) Provisional application No. 60/619,138, filed on Oct. 15, 2004.

(51) Int. Cl.
*A61K 31/496* (2006.01)
*C07D 401/14* (2006.01)

(52) U.S. Cl. .................... 544/364; 544/370; 514/253.01

(58) Field of Classification Search ................. 544/364, 544/370
See application file for complete search history.

(56) References Cited

U.S. PATENT DOCUMENTS

| | | | |
|---|---|---|---|
| 6,444,687 B1 * | 9/2002 | Stamford et al. | ............ 514/318 |
| 2004/0152690 A1 | 8/2004 | Balan et al. | |

FOREIGN PATENT DOCUMENTS

| JP | 54/48763 A * | 4/1979 |
|---|---|---|
| WO | WO-99/31089 A1 * | 6/1999 |
| WO | WO 1999/31089 | 6/1999 |

OTHER PUBLICATIONS

CA Registry No. 753435-35-7, indexed in the Registry file on STN on Sep. 29, 2004.*
CA Registry No. 736915-29-0, indexed in the Registry file on STN on Sep. 1, 2004.*
CA Registry No. 733726-92-6, indexed in the Registry file on STN on Aug. 27, 2004.*
CA Registry No. 696583-01-4, indexed in the Registry file on STN on Jun. 20, 2004.*
An English translation of JP 54-48763, 1979.*
Schroder, et al., Eur J. Med Chem., "Nichtsteroidale Entzndungshemmer.7. Entz ndungshemmende Methansulfonanilide II" 17 (2) 165-172 (1982).

* cited by examiner

*Primary Examiner*—Laura L. Stockton
(74) *Attorney, Agent, or Firm*—Richard V. Person

(57) ABSTRACT

Therapeutic benzimidazoles and compositions containing them, for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders.

11 Claims, No Drawings

VANILLOID RECEPTOR LIGANDS AND THEIR USE IN TREATMENTS

This application claims the benefit of U.S. Provisional Application No. 60/619,138 filed Oct. 15, 2004, which is hereby incorporated by reference.

BACKGROUND

The vanilloid receptor 1 (VR1) is the molecular target of capsaicin, the active ingredient in hot peppers. Julius et al. reported the molecular cloning of VR1 (Caterina et al., 1997). VR1 is a non-selective cation channel which is activated or sensitized by a series of different stimuli including capsaicin and resiniferatoxin (exogenous activators), heat & acid stimulation and products of lipid bilayer metabolism, anandamide (Premkumar et al., 2000, Szabo et al., 2000, Gauldie et al., 2001, Olah et al., 2001) and lipoxygenase metabolites (Hwang et al., 2000). VR1 is highly expressed in primary sensory neurons (Caterina et al., 1997) in rats, mice and humans (Onozawa et al., 2000, Mezey et al., 2000, Helliwell et al., 1998, Cortright et al., 2001). These sensory neurons innervate many visceral organs including the dermis, bones, bladder, gastrointestinal tract and lungs; VR1 is also expressed in other neuronal and non-neuronal tissues including but not limited to, CNS nuclei, kidney, stomach and T-cells (Nozawa et al., 2001, Yiangou et al., 2001, Birder et al., 2001). Presumably expression in these various cells and organs may contribute to their basic properties such as cellular signaling and cell division.

Prior to the molecular cloning of VR1, experimentation with capsaicin indicated the presence of a capsaicin sensitive receptor, which could increase the activity of sensory neurons in humans, rats and mice (Holzer, 1991; Dray, 1992, Szallasi and Blumberg 1996, 1999). The results of acute activation by capsaicin in humans was pain at injection site and in other species increased behavioral sensitivity to sensory stimuli (Szallasi and Blumberg, 1999). Capsaicin application to the skin in humans causes a painful reaction characterized not only by the perception of heat and pain at the site of administration but also by a wider area of hyperalgesia and allodynia, two characteristic symptoms of the human condition of neuropathic pain (Holzer, 1991). Taken together, it seems likely that increased activity of VR1 plays a significant role in the establishment and maintenance of pain conditions. Topical or intradermal injection of capsaicin has also been shown to produce localized vasodilation and edema production (Szallasi and Blumberg 1999, Singh et al., 2001). This evidence indicates that capsaicin through it's activation of VR1 can regulate afferent and efferent function of sensory nerves. Sensory nerve involvement in diseases could therefore be modified by molecules which effect the function of the vanilloid receptor to increase or decrease the activity of sensory nerves.

VR1 gene knockout mice have been shown to have reduced sensory sensitivity to thermal and acid stimuli (Caterina et al., 2000)). This supports the concept that VR1 contributes not only to generation of pain responses (i.e. via thermal, acid or capsaicin stimuli) but also to the maintenance of basal activity of sensory nerves. This evidence agrees with studies demonstrating capsaicin sensitive nerve involvement in disease. Primary sensory nerves in humans and other species can be made inactive by continued capsaicin stimulation. This paradigm causes receptor activation induced desensitization of the primary sensory nerve—such reduction is sensory nerve activity in vivo makes subjects less sensitive to subsequent painful stimuli. In this regard both capsaicin and resiniferatoxin (exogenous activators of VR1), produce desensitization and they have been used for many proof of concept studies in in vivo models of disease (Holzer, 1991, Dray 1992, Szallasi and Blumberg 1999).

BIBLIOGRAPHY

Birder-L A. Kanai-A J. de-Groat-W C. Kiss-S. Nealen-M L. Burke-N E. Dineley-K E. Watkins-S. Reynolds-I J. Caterina-M J. (2001) Vanilloid receptor expression suggests a sensory role for urinary bladder epithelial cells. PNAS 98: 23: 13396-13401.

Caterina, M. J., Schumacher, M. A., Tominaga, M., Rosen, T. A., Levine, J. D., and Julius, D, (1997). The capsaicin receptor: a heat-activated ion channel in the pain pathway. Nature 389: 816-824.

Caterina-M J. Leffler-A. Malmberg-A B. Martin-W J. Trafton-J. Petersen-Zeitz K R. Koltzenburg-M. Basbaum-A I. Julius-D (2000) Impaired nociception and pain sensation in mice lacking the capsaicin receptor. Science- (WASH-DC). 288: 5464: 306-313.

Cortright-D N. Crandall-M. Sanchez-J F. Zou-T. Krause-J E. White-G (2001) The tissue distribution and functional characterization of human VR1. Biochemical and Biophysical Research Communications 281: 5: 1183-1189

Dray, A., (1992). Therapeutic potential of capsaicin-like molecules. Life Sciences 51: 1759-1765.

Gauldie-S D. McQueen-D S. Pertwee-R. Chessell-I P. (2001) Anandamide activates peripheral nociceptors in normal and arthritic rat knee joints. British Journal of Pharmacology 132: 3: 617-621.

Helliwell-R J A. McLatchie-L M. Clarke-M. Winter-J. Bevan-S. McIntyre-P (1998) Capsaicin sensitivity is associated with expression of the vanilloid (capsaicin) receptor (VR1) mRNA in adult rat sensory ganglia. Neuroscience Lett. 250: 3: 177-180.

Holzer, P. (1991) Capsaicin: Cellular targets, Mechanisms of Action and selectivity for thin sensory neurons. Pharmacological reviews 43: 2: 143-201

Hwang-S W. Cho-H. Kwak-J. Lee-S Y. Kang-C J. Jung-J. Cho-S. Min-K H. Suh-Y G. Kim-D. Oh-U. (2000) Direct activation of capsaicin receptors by products of lipoxygenases: Endogenous capsaicin-like substances. PNAS 97: 11: 6155-6160.

Mezey-E. Toth-Z E. Cortright-D N. Arzubi-M K. Krause-J E. Elde-R. Guo-A. Blumberg-P M. Szallasi-A (2000) Distribution of mRNA for vanilloid receptor subtype 1 (VR1), and VR1-like immunoreactivity, in the central nervous system of the rat and human. PNAS 97: 7: 3655-3660.

Nozawa-Y. Nishihara-K. Yamamoto-A. Nakano-M. Ajioka-H. Matsuura-N. (2001) Distribution and characterization of vanilloid receptors in the rat stomach. Neuroscience Letters 309: 1: 33-36.

Olah-Z. Karai-L. Iadarola-M J. (2001) Anandamide activates vanilloid receptor 1 (VR1) at acidic pH in dorsal root ganglia neurons and cells ectopically expressing VR1. Journal of Biological Chemistry 276: 33, 31163-31170.

Onozawa-K. Nakamura-A. Tsutsumi-S. Yao-J. Ishikawa-R. Kohama-K. (2000) Tissue distribution of capsaicin receptor in the various organs of rats. Proc. Jpn. Acad. Ser. B, Phys.-Biol. Sci. 76: 5: 68-72.

Premkumar-L S. Ahern-G P. (2000) Induction of vanilloid receptor channel activity by protein kinase C. Nature (London) 408: 6815: 985-990.

Singh-L K. Pang-X. Alexacos-N. Letourneau-R. Theoharides-T C. (1999) Acute immobilization stress triggers skin mast cell degranulation via corticotropin releasing hormone, neurotensin, and substance P: A link to neurogenic skin disorders. Brain Behav. Immun. 13: 3: 225-239.

Szallasi, A. Blumberg-P M (1996) Vanilloid receptors: New insights enhance potential as a therapeutic target. Pain 68: 195-208

Szallasi-A. Blumberg-P M. (1999) Vanilloid (capsaicin) receptors and mechanisms. Pharmacol. Rev. 51: 2: 159-211.

Szabo-T. Wang-J. Gonzalez-A. Kedei-N. Lile-J. Treanor-J. Blumberg-P M. (2000) Pharmacological characterization of the human vanilloid receptor type-1 (hVR1). Society for Neuroscience Abstracts. 26:1-2: 634.18.

Tominaga M., Caterina, M. J., Malmberg, A. B., Rosen, T. A., Gilbert, H., Skinner, K., Raumann, B. E., Basbaum, A. I., and Julius, D., (1998). The cloned capsaicin receptor integrates multiple pain-producing stimuli. Neuron 21: 531-543.

Yiangou-Y. Facer-P. Dyer-N H C. Chan-C L H. Knowles-C. Williams-N S. Anand-P. (2001) Vanilloid receptor 1 immunoreactivity in inflamed human bowel. Lancet (North American Edition) 357: 9265: 1338-1339.

Yiangou-Y. Facer-P. Ford-A. Brady-C. Wiseman-O. Fowler-C J. Anand-P. (2001) Capsaicin receptor VR1 and ATP-gated ion channel P2X3 in human urinary bladder. BJU International 87: 9: 774-779.

Wang-H. Bian-D. Zhu-D. Zajic-G. Loeloff-R. Lile-J. Wild-K. Treanor-J. Curran-E. (2000) Inflammation-induced upregulation of VR1 in rat spinal cord and DRG correlates with enhanced nociceptive processing. Society for Neuroscience Abstracts 26:1-2: 632.15.

SUMMARY

The present invention comprises a new class of compounds useful in the treatment of diseases, such as vanilloid-receptor-mediated diseases and other maladies, such as inflammatory or neuropathic pain and diseases involving sensory nerve function such as asthma, rheumatoid arthritis, osteoarthritis, inflammatory bowel disorders, urinary incontinence, migraine and psoriasis. In particular, the compounds of the invention are useful for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders. Accordingly, the invention also comprises pharmaceutical compositions comprising the compounds, methods for the treatment of vanilloid-receptor-mediated diseases, such as inflammatory or neuropathic pain, asthma, rheumatoid arthritis, osteoarthritis, inflammatory bowel disorders, urinary incontinence, migraine and psoriasis diseases, using the compounds and compositions of the invention, and intermediates and processes useful for the preparation of the compounds of the invention.

The compounds of the invention are represented by the following general structure:

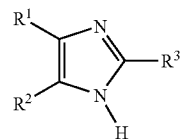

or a pharmaceutically acceptable salt thereof, wherein $R^1$, $R^2$ and $R^3$ are defined herein.

The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION

One aspect of the current invention relates to compounds having the general structure:

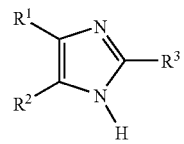

or any pharmaceutically-acceptable salt or hydrate thereof, wherein:

$R^1$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from $R^e$, halo, cyano, nitro, $-C(=O)R^b$, $-C(=O)OR^b$, $-C(=O)NR^aR^a$, $-C(=NR^a)NR^aR^a$, $-OR^a$, $-OC(=O)R^b$, $-OC(=O)NR^aR^a$, $-OC(=O)N(R^a)S(=O)_2R^b$, $-OC_{2-6}alkylNR^aR^a$, $-OC_{2-6}alkylOR^a$, $-SR^a$, $-S(=O)R^b$, $-S(=O)_2R^b$, $-S(=O)_2NR^aR^a$, $-S(=O)_2N(R^a)C(=O)R^b$, $-S(=O)_2N(R^a)C(=O)OR^b$, $-S(=O)_2N(R^a)C(=O)NR^aR^a$, $-NR^aR^a$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-N(R^a)S(=O)_2NR^aR^a$, $-NR^aC_{2-6}alkylNR^aR^a$ and $-NR^aC_{2-6}alkylOR^a$, and the ring is additionally substituted by 0, 1, 2, 3, 4 or 5 substituents independently selected from Br, Cl, F and I;

$R^2$ is (A) a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from $R^e$, halo, cyano, nitro, —C(=O)$R^b$, —C(=O)O$R^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2\text{-}6}$alkylNR$^a$R$^a$, —OC$_{2\text{-}6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2\text{-}6}$alkylNR$^a$R$^a$ and —NR$^a$C$_{2\text{-}6}$alkylOR$^a$, and the ring is additionally substituted by 0, 1, 2, 3, 4 or 5 substituents independently selected from Br, Cl, F and I; or $R^2$ is (B) $C_{1\text{-}6}$alkyl substituted by 0, 1, 2 or 3 substituents independently selected from $C_{1\text{-}4}$haloalkyl, halo, oxo, cyano, nitro, —C(=O)$R^b$, —C(=O)O$R^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2\text{-}6}$alkylNR$^a$R$^a$, —OC$_{2\text{-}6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2\text{-}6}$alkylNR$^a$R$^a$ and —NR$^a$C$_{2\text{-}6}$alkylOR$^a$, and additionally substituted by 0 or 1 saturated, partially saturated or unsaturated 5-, 6- or 7-membered monocyclic or 6-, 7-, 8-, 9-, 10- or 11-membered bicyclic rings containing 0, 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from $C_{1\text{-}8}$alkyl, $C_{1\text{-}4}$haloalkyl, halo, cyano, oxo, nitro, —C(=O)$R^b$, —C(=O)O$R^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2\text{-}6}$alkylNR$^a$R$^a$, —OC$_{2\text{-}6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2\text{-}6}$alkylNR$^a$R$^a$ and —NR$^a$C$_{2\text{-}6}$alkylOR$^a$, and the ring is additionally substituted by 0, 1, 2, 3, 4 or 5 substituents independently selected from Br, Cl, F and I; or $R^2$ is (C) halo, cyano, nitro, —C(=O)$R^b$, —C(=O)O$R^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2\text{-}6}$alkylNR$^a$R$^a$, —OC$_{2\text{-}6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2\text{-}6}$alkylNR$^a$R$^a$ or —NR$^a$C$_{2\text{-}6}$alkylOR$^a$;

$R^3$ is

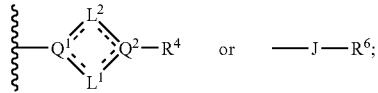

J is NH, N($C_{1\text{-}3}$alkyl), O, S(=O) or S(=O)$_2$;

$L^1$ is a saturated, unsaturated, or partially-saturated chain of 1, 2 or 3 carbon atoms substituted at each open position by $R^5$;

$L^2$ is a saturated, unsaturated, or partially-saturated chain of 1, 2 or 3 carbon atoms substituted at each open position by $R^{5'}$; wherein the combined number of carbon atoms in the $L^1$ and $L^2$ chains is 3, 4 or 5;

$R^4$ is phenyl or naphthyl, wherein the phenyl and naphthyl are substituted by 1, 2, 3 or 4 substituents selected from $R^c$, $R^e$, halo, $C_{1\text{-}4}$haloalkyl, cyano, nitro, —C(=O)$R^e$, —C(=O)OR$^h$, —C(=O)NR$^a$R$^h$, —C(=NR$^a$)NR$^a$R$^h$, —OR$^h$, —OC(=O)R$^e$, —OC(=O)NR$^a$R$^h$, —OC(=O)N(R$^a$)S(=O)$_2$R$^e$, —OC$_{2\text{-}6}$alkylNR$^a$R$^h$, —OC$_{2\text{-}6}$alkylOR$^h$, —SR$^e$, —S(=O)R$^e$, —S(=O)$_2$R$^e$, —S(=O)$_2$NR$^a$R$^h$, —S(=O)$_2$N(R$^a$)C(=O)R$^e$, —S(=O)$_2$N(R$^a$)C(=O)OR$^h$, —S(=O)$_2$N(R$^a$)C(=O)NR$^a$R$^h$, —NR$^a$R$^h$, —N(R$^a$)C(=O)R$^e$, —N(R$^a$)C(=O)OR$^h$, —N(R$^a$)C(=O)NR$^a$R$^h$, —N(R$^a$)C(=NR$^a$)NR$^a$R$^h$, —N(R$^a$)S(=O)$_2$R$^e$, —N(R$^a$)S(=O)$_2$NR$^a$R$^h$, —NR$^a$C$_{2\text{-}6}$alkylNR$^a$R$^h$, —NR$^a$C$_{2\text{-}6}$alkylOR$^h$, —C(=O)R$^g$, —C(=O)OR$^g$, —C(=O)NR$^a$R$^g$, —C(=NR$^a$)NR$^a$R$^g$, —OR$^g$, —OC(=O)R$^g$, —OC(=O)NR$^a$R$^g$, —OC(=O)N(R$^a$)S(=O)$_2$R$^g$, —OC(=O)N(R$^g$)S(=O)$_2$R$^e$, —OC$_{2\text{-}6}$alkylNR$^a$R$^g$, —OC$_{2\text{-}6}$alkylOR$^g$, —SR$^g$, —S(=O)R$^g$, —S(=O)$_2$R$^g$, —S(=O)$_2$NR$^a$R$^g$, —S(=O)$_2$N(R$^g$)C(=O)R$^e$, —S(=O)$_2$N(R$^a$)C(=O)R$^g$, —S(=O)$_2$N(R$^g$)C(=O)OR$^h$, —S(=O)$_2$N(R$^a$)C(=O)OR$^g$, —S(=O)$_2$N(R$^g$)C(=O)NR$^a$R$^h$, —S(=O)$_2$N(R$^a$)C(=O)NR$^a$R$^g$, —NR$^a$R$^g$, —N(R$^g$)C(=O)R$^e$, —N(R$^a$)C(=O)R$^g$, —N(R$^g$)C(=O)OR$^h$, —N(R$^a$)C(=O)OR$^g$, —N(R$^g$)C(=O)NR$^a$R$^h$, —N(R$^a$)C(=O)NR$^a$R$^g$, —N(R$^g$)C(=NR$^a$)NR$^a$R$^h$, —N(R$^a$)C(=NR$^a$)NR$^a$R$^g$, —N(R$^g$)S(=O)$_2$R$^e$, —N(R$^a$)S(=O)$_2$R$^g$, —N(R$^g$)S(=O)$_2$NR$^a$R$^h$, —N(R$^a$)S(=O)$_2$NR$^a$R$^g$, —NR$^h$C$_{2\text{-}6}$alkylNR$^a$R$^g$, —NR$^a$C$_{2\text{-}6}$alkylNR$^a$R$^g$, —NR$^g$C$_{2\text{-}6}$alkylOR$^h$ and —NR$^a$C$_{2\text{-}6}$alkylOR$^g$; or $R^4$ is $R^c$ substituted by 0, 1, 2, 3 or 4 substituents selected from $R^c$, $R^e$, halo, $C_{1\text{-}4}$haloalkyl, cyano, nitro, —C(=O)R$^e$, —C(=O)OR$^h$, —C(=O)NR$^a$R$^h$, —C(=NR$^a$)NR$^a$R$^h$, —OR$^h$, —OC(=O)R$^e$, —OC(=O)NR$^a$R$^h$, —OC(=O)N(R$^a$)S(=O)$_2$R$^e$, —OC$_{2\text{-}6}$alkylNR$^a$R$^h$, —OC$_{2\text{-}6}$alkylOR$^h$, —SR$^e$, —S(=O)R$^e$, —S(=O)$_2$R$^e$, —S(=O)$_2$NR$^a$R$^h$, —S(=O)$_2$N(R$^a$)C(=O)R$^e$, —S(=O)$_2$N(R$^a$)C(=O)OR$^h$, —S(=O)$_2$N(R$^a$)C(=O)NR$^a$R$^h$, —NR$^a$R$^h$, —N(R$^a$)C(=O)R$^e$, —N(R$^a$)C(=O)OR$^h$, —N(R$^a$)C(=O)NR$^a$R$^h$, —N(R$^a$)C(=NR$^a$)NR$^a$R$^h$, —N(R$^a$)S(=O)$_2$R$^e$, —N(R$^a$)S(=O)$_2$NR$^a$R$^h$, —NR$^a$C$_{2\text{-}6}$alkylNR$^a$R$^h$, —NR$^a$C$_{2\text{-}6}$alkylOR$^h$, —C(=O)R$^g$, —C(=O)OR$^g$, —C(=O)NR$^a$R$^g$, —C(=NR$^a$)NR$^a$R$^g$, —OR$^g$, —OC(=O)R$^g$, —OC(=O)NR$^a$R$^g$, —OC(=O)N(R$^a$)S(=O)$_2$R$^g$, —OC(=O)N(R$^g$)S(=O)$_2$R$^e$, —OC$_{2\text{-}6}$alkylNR$^a$R$^g$, —OC$_{2\text{-}6}$alkylOR$^g$, —SR$^g$, —S(=O)R$^g$, —S(=O)$_2$R$^g$, —S(=O)$_2$NR$^a$R$^g$, —S(=O)$_2$N(R$^g$)C(=O)R$^e$, —S(=O)$_2$N(R$^a$)C(=O)R$^g$, —S(=O)$_2$N(R$^g$)C(=O)OR$^h$, —S(=O)$_2$N(R$^a$)C(=O)OR$^g$, —S(=O)$_2$N(R$^g$)C(=O)NR$^a$R$^h$, —S(=O)$_2$N(R$^a$)C(=O)NR$^a$R$^g$, —NR$^a$R$^g$, —N(R$^g$)C(=O)R$^e$, —N(R$^a$)C(=O)R$^g$, —N(R$^g$)C(=O)OR$^h$, —N(R$^a$)C(=O)OR$^g$, —N(R$^g$)C(=O)NR$^a$R$^h$, —N(R$^a$)C(=O)NR$^a$R$^g$, —N(R$^g$)C(=NR$^a$)NR$^a$R$^h$, —N(R$^a$)C(=NR$^a$)NR$^a$R$^g$, —N(R$^g$)S(=O)$_2$R$^e$, —N(R$^a$)S(=O)$_2$R$^g$, —N(R$^g$)S(=O)$_2$NR$^a$R$^h$, —N(R$^a$)S(=O)$_2$NR$^a$R$^g$, —NR$^h$C$_{2-6}$alkylNR$^a$R$^g$, —NR$^a$C$_{2-6}$ alkylNR$^a$R$^g$, —NR$^g$C$_{2-6}$alkylOR$^h$ and —NR$^a$C$_{2-6}$alkylOR$^g$;

R$^5$ is, independently, in each instance, H, C$_{1-8}$alkyl, C$_{1-4}$haloalkyl, —O(C$_{1-7}$alkyl), —N(C$_{1-7}$alkyl)R$^a$, or a C$_{1-6}$alkyl substituted by 1, 2 or 3 substituents selected from halo, cyano, —OR$^a$, —OC(=O)R$^b$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —NR$^a$C$_{2-6}$alkylNR$^a$R$^a$ and —NR$^a$C$_{2-6}$alkylOR$^a$; wherein any two geminal R$^5$ groups may additionally be oxo;

R$^{5'}$ is, independently, in each instance, H, C$_{1-8}$alkyl, C$_{1-4}$haloalkyl, —O(C$_{1-7}$alkyl), —N(C$_{1-7}$alkyl)R$^a$, or a C$_{1-6}$alkyl substituted by 1, 2 or 3 substituents selected from halo, cyano, —OR$^a$, —OC(=O)R$^b$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —NR$^a$C$_{2-6}$alkylNR$^a$R$^a$ and —NR$^a$C$_{2-6}$alkylOR$^a$; wherein any two geminal R$^{5'}$ groups may additionally be oxo;

R$^6$ is phenyl vicinally fused with a 5-, 6- or 7-membered saturated, partially-saturated or unsaturated ring containing 0, 1, 2 or 3 heteroatoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and the ring is additionally substituted by 0, 1, 2, 3, 4 or 5 substituents independently selected from Br, Cl, F and I;

R$^a$ is independently, at each instance, H or R$^b$;

R$^b$ is independently, at each instance, phenyl, benzyl or C$_{1-6}$alkyl, the phenyl, benzyl and C$_{1-6}$alkyl being substituted by 0, 1, 2 or 3 substituents selected from halo, C$_{1-4}$alkyl, C$_{1-3}$haloalkyl, —OC$_{1-4}$alkyl, —NH$_2$, —NHC$_{1-4}$alkyl, —N(C$_{1-4}$alkyl)C$_{1-4}$alkyl;

R$^c$ is independently at each instance a saturated, partially saturated or unsaturated 5-, 6- or 7-membered monocyclic or 6-, 7-, 8-, 9-, 10- or 11-membered bicyclic ring containing 1, 2, 3 or 4 atoms selected from N, O and S, wherein the carbon atoms of the ring are substituted by 0, 1 or 2 oxo groups;

R$^d$ is independently at each instance C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O) R$^b$, —OC(=O)NR$^a$R$^a$, —OC(=O)N(R$^a$)S(=O)$_2$R$^b$, —OC$_{2-6}$alkylNR$^a$R$^a$, —OC$_2$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O) R$^b$, —S(=O)$_2$N(R$^a$)C(=O)OR$^b$, —S(=O)$_2$N(R$^a$)C(=O) NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

R$^e$ is independently at each instance C$_{1-6}$alkyl substituted by 0, 1, 2 or 3 substituents independently selected from R$^d$ and additionally substituted by 0 or 1 substituents selected from R$^g$;

R$^g$ is independently at each instance a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O) NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; and R$^h$ is independently at each instance R$^e$ or H.

In another embodiment, in conjunction with any one of the above and below embodiments, L$^1$ is a saturated, unsaturated, or partially-saturated chain of 2 or 3 carbon atoms substituted at each open position by R$^5$.

In another embodiment, in conjunction with any one of the above and below embodiments, L$^1$ is a saturated, unsaturated, or partially-saturated chain of 2 carbon atoms substituted at each open position by R$^5$.

In another embodiment, in conjunction with any one of the above and below embodiments, L$^2$ is is a saturated, unsaturated, or partially-saturated chain of 2 or 3 carbon atoms substituted at each open position by R$^{5'}$.

In another embodiment, in conjunction with any one of the above and below embodiments, L$^2$ is is a saturated, unsaturated, or partially-saturated chain of 2 carbon atoms substituted at each open position by R$^{5'}$.

In another embodiment, in conjunction with any one of the above and below embodiments, the combined number of carbon atoms in the L$^1$ and L$^2$ chains is 3.

In another embodiment, in conjunction with any one of the above and below embodiments, the combined number of carbon atoms in the L$^1$ and L$^2$ chains is 4.

In another embodiment, in conjunction with any one of the above and below embodiments, the combined number of carbon atoms in the L$^1$ and L$^2$ chains is 5.

In another embodiment, in conjunction with any one of the above and below embodiments, the group:

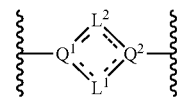

is selected from

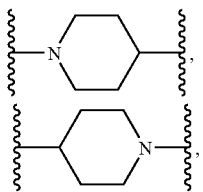 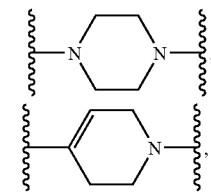

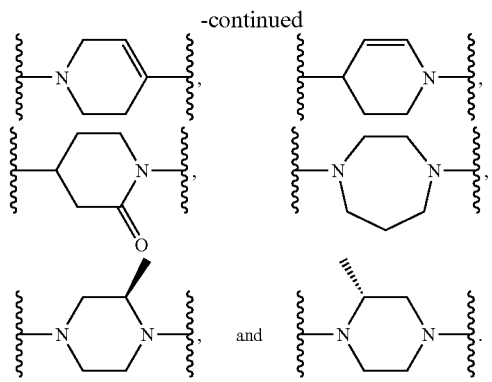

In another embodiment, in conjunction with any one of the above and below embodiments, $Q^1$ is N.

In another embodiment, in conjunction with any one of the above and below embodiments, $Q^2$ is N.

In another embodiment, in conjunction with any one of the above and below embodiments, $R^1$ is a saturated, partially saturated or unsaturated 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from $R^e$, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkylN$R^aR^a$ and —N$R^a$C$_{2-6}$alkylO$R^a$, and the ring is additionally substituted by 0, 1, 2, 3, 4 or 5 substituents independently selected from Br, Cl, F and I.

In another embodiment, in conjunction with any one of the above and below embodiments, $R^1$ is a saturated, partially saturated or unsaturated 5-, 6- or 7-membered monocyclic ring containing 0, 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from $R^e$, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkylN$R^aR^a$ and —N$R^a$C$_{2-6}$alkylO$R^a$, and the ring is additionally substituted by 0, 1, 2 or 3 substituents independently selected from Br, Cl, F and I.

In another embodiment, in conjunction with any one of the above and below embodiments, $R^1$ is a saturated, partially saturated or unsaturated 5-, 6- or 7-membered monocyclic ring containing 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from $R^e$, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkylN$R^aR^a$ and —N$R^a$C$_{2-6}$alkylO$R^a$, and the ring is additionally substituted by 0, 1, 2 or 3 substituents independently selected from Br, Cl, F and I.

In another embodiment, in conjunction with any one of the above and below embodiments, $R^1$ is a saturated, partially saturated or unsaturated 5-, 6- or 7-membered monocyclic carbocyclic ring, wherein the carbon atoms of the ring are substituted by 0, 1 or 2 oxo or thioxo groups, and the ring is substituted by 0, 1, 2 or 3 substituents selected from $R^e$, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkylN$R^aR^a$ and —N$R^a$C$_{2-6}$alkylO$R^a$, and the ring is additionally substituted by 0, 1, 2 or 3 substituents independently selected from Br, Cl, F and I.

In another embodiment, in conjunction with any one of the above and below embodiments, $R^1$ is phenyl, pyridinyl or pyrimidinyl, all of which are substituted by 0, 1, 2 or 3 substituents selected from $R^e$, halo, cyano, nitro, —C(=O)$R^b$, —C(=O)O$R^b$, —C(=O)N$R^aR^a$, —C(=N$R^a$)N$R^aR^a$, —O$R^a$, —C(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkylN$R^aR^a$ and —N$R^a$C$_{2-6}$alkylO$R^a$, and the phenyl, pyridinyl or pyrimidinyl is additionally substituted by 0, 1, 2 or 3 substituents independently selected from Br, Cl, F and I.

In another embodiment, in conjunction with any one of the above and below embodiments, $R^1$ is phenyl, pyridinyl or pyrimidinyl, all of which are substituted by 1, 2 or 3 substituents selected from $R^e$, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —C$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkylN$R^aR^a$ and —N$R^a$C$_{2-6}$alkylO$R^a$, and the phenyl, pyridinyl or pyrimidinyl is additionally substituted by 0, 1, 2 or 3 substituents independently selected from Br, Cl, F and I.

In another embodiment, in conjunction with any one of the above and below embodiments, $R^1$ is phenyl substituted by 1, 2 or 3 substituents selected from $R^e$, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkylN$R^aR^a$ and —N$R^a$C$_{2-6}$alkylO$R^a$, and the phenyl is additionally substituted by 0, 1, 2 or 3 substituents independently selected from Br, Cl, F and I.

In another embodiment, in conjunction with any one of the above and below embodiments, $R^1$ is phenyl substituted by a $C_{1-3}$haloalkyl group and additionally substituted by 0, 1, 2 or 3 F atoms.

In another embodiment, in conjunction with any one of the above and below embodiments, $R^1$ is 4-trifluoromethylphenyl.

In another embodiment, in conjunction with any one of the above and below embodiments, $R^2$ is a saturated, partially saturated or unsaturated 5-, 6- or 7-membered monocyclic or 6-, 7-, 8-, 9-, 10- or 11-membered bicyclic ring containing 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from $R^e$, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkylN$R^aR^a$ and —N$R^a$C$_{2-6}$alkylO$R^a$, and the ring is additionally substituted by 0, 1, 2, 3, 4 or 5 substituents independently selected from Br, Cl, F and I.

In another embodiment, in conjunction with any one of the above and below embodiments, $R^2$ is a saturated, partially saturated or unsaturated 6-, 7-, 8-, 9-, 10- or 11-membered bicyclic ring containing 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from $R^e$, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkylN$R^aR^a$ and —N$R^a$C$_{2-6}$alkylO$R^a$, and the ring is additionally substituted by 0, 1, 2, 3, 4 or 5 substituents independently selected from Br, Cl, F and I.

In another embodiment, in conjunction with any one of the above and below embodiments, $R^2$ is a saturated, partially saturated or unsaturated 5-, 6- or 7-membered monocyclic ring containing 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from $R^e$, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkylN$R^aR^a$ and —N$R^a$C$_{2-6}$alkylO$R^a$, and the ring is additionally substituted by 0, 1, 2 or 3 substituents independently selected from Br, Cl, F and I.

In another embodiment, in conjunction with any one of the above and below embodiments, $R^2$ is naphthyl or phenyl substituted by 0, 1, 2 or 3 substituents selected from $R^e$, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkylN$R^aR^a$ and —N$R^a$C$_{2-6}$alkylO$R^a$, and the ring is additionally substituted by 0, 1, 2, 3, 4 or 5 substituents independently selected from Br, Cl, F and I.

In another embodiment, in conjunction with any one of the above and below embodiments, $R^2$ is phenyl substituted by 0, 1, 2 or 3 substituents selected from $R^e$, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkylN$R^aR^a$ and —N$R^a$C$_{2-6}$alkylO$R^a$, and the ring is additionally substituted by 0, 1, 2, 3 or 4 substituents independently selected from Br, Cl, F and I.

In another embodiment, in conjunction with any one of the above and below embodiments, $R^2$ is phenyl substituted by 1, 2 or 3 substituents selected from $R^e$, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkylN$R^aR^a$ and —N$R^a$C$_{2-6}$alkylO$R^a$, and the ring is additionally substituted by 0, 1, 2, 3 or 4 substituents independently selected from Br, Cl, F and I.

In another embodiment, in conjunction with any one of the above and below embodiments, $R^2$ is $C_{1-6}$alkyl substituted by 0, 1, 2 or 3 substituents independently selected from $C_{1-4}$haloalkyl, halo, oxo, cyano, nitro, —C(=O)$R^b$, —C(=O)O$R^b$, —C(=O)N$R^aR^a$, —C(=N$R^a$)N$R^aR^a$, —O$R^a$, —C(=O)

$R^b$, —OC(=O)$NR^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2NR^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2NR^aR^a$, —N$R^c$C$_{2-6}$alkylN$R^aR^a$ and —N$R^c$C$_{2-6}$alkylO$R^a$, and additionally substituted by 0 or 1 saturated, partially saturated or unsaturated 5-, 6- or 7-membered monocyclic or 6-, 7-, 8-, 9-, 10- or 11-membered bicyclic rings containing 0, 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from $C_{1-8}$alkyl, $C_{1-4}$haloalkyl, halo, cyano, oxo, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2NR^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2NR^aR^a$, —N$R^c$C$_{2-6}$alkylN$R^aR^a$ and —N$R^c$C$_{2-6}$alkylO$R^a$, and the ring is additionally substituted by 0, 1, 2, 3, 4 or 5 substituents independently selected from Br, Cl, F and I.

In another embodiment, in conjunction with any one of the above and below embodiments, $R^2$ is $C_{1-6}$alkyl.

In another embodiment, in conjunction with any one of the above and below embodiments, $R^2$ is halo, cyano, nitro, —C(=O)$R^g$, —C(=O)$R^b$, —C(=O)$R^b$, —C(=O)O$R^b$, —C(=O)O$R^e$, —C(=O)O$R^g$, —C(=O)N$R^aR^a$, —C(=O)N$R^aR^e$, —C(=O)N$R^aR^g$, —C(=N$R^a$)N$R^aR^a$, —C(=N$R^a$)N$R^aR^e$, —C(=N$R^a$)N$R^aR^g$, —O$R^a$, —O$R^e$, —O$R^g$, —OC(=O)$R^b$, —OC(=O)$R^e$, —OC(=O)$R^g$, —OC(=O)N$R^aR^a$, —OC(=O)N$R^aR^e$, —OC(=O)N$R^aR^g$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2NR^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, N$R^aR^e$, N$R^aR^g$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2NR^aR^a$, —N$R^c$C$_{2-6}$alkylN$R^aR^a$ or —N$R^c$C$_{2-6}$alkylO$R^a$.

In another embodiment, in conjunction with any one of the above and below embodiments, $R^2$ is halo.

In another embodiment, in conjunction with any one of the above and below embodiments, $R^2$ is —C(=O)$R^g$, —C(=O)$R^b$, —C(=O)$R^b$, —C(=O)O$R^b$, —C(=O)O$R^e$, —C(=O)O$R^g$, —C(=O)N$R^aR^a$, —C(=O)N$R^aR^e$, —C(=O)N$R^aR^g$, —C(=N$R^a$)N$R^aR^a$, —C(=N$R^a$)N$R^aR^e$, —C(=N$R^a$)N$R^aR^g$, —O$R^a$, —O$R^e$, —O$R^g$, —OC(=O)$R^b$, —OC(=O)$R^e$, —OC(=O)$R^g$, —OC(=O)N$R^aR^a$, —OC(=O)N$R^aR^e$, —OC(=O)N$R^aR^g$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2NR^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, N$R^aR^e$, N$R^aR^g$, —N($R^a$)C(=O)$R^b$, —N($R^a$)C(=O)$R^e$, —N($R^a$)C(=O)$R^g$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2NR^aR^a$, —N$R^c$C$_{2-6}$alkylN$R^aR^a$ or —N$R^c$C$_{2-6}$alkylO$R^a$.

In another embodiment, in conjunction with any one of the above and below embodiments, $R^3$ is

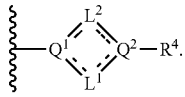

In another embodiment, in conjunction with any one of the above and below embodiments, $R^3$ is -J-$R^6$.

In another embodiment, in conjunction with any one of the above and below embodiments, J is NH, N($C_{1-3}$alkyl) or O.

In another embodiment, in conjunction with any one of the above and below embodiments, J is NH or N($C_{1-3}$alkyl).

In another embodiment, in conjunction with any one of the above and below embodiments, J is O.

In another embodiment, in conjunction with any one of the above and below embodiments, $R^4$ is phenyl or naphthyl, wherein the phenyl and naphthyl are substituted by 1, 2, 3 or 4 substituents selected from $R^c$, $R^e$, halo, $C_{1-4}$haloalkyl, cyano, nitro, —C(=O)$R^e$, —C(=O)O$R^h$, —C(=O)N$R^aR^h$, —C(=N$R^a$)N$R^aR^h$, —O$R^h$, —OC(=O)$R^e$, —OC(=O)N$R^aR^h$, —OC(=O)N($R^a$)S(=O)$_2R^e$, —OC$_{2-6}$alkylN$R^aR^h$, —OC$_{2-6}$alkylO$R^h$, —S$R^e$, —S(=O)$R^e$, —S(=O)$_2R^e$, —S(=O)$_2NR^aR^h$, —S(=O)$_2$N($R^a$)C(=O)$R^e$, —S(=O)$_2$N($R^a$)C(=O)O$R^h$, —S(=O)$_2$N($R^a$)C(=O)N$R^aR^h$, —N$R^aR^h$, —N($R^a$)C(=O)$R^e$, —N($R^a$)C(=O)O$R^h$, —N($R^a$)C(=O)N$R^aR^h$, —N($R^a$)C(=N$R^a$)N$R^aR^h$, —N($R^a$)S(=O)$_2R^e$, —N($R^a$)S(=O)$_2NR^aR^h$, —N$R^c$C$_{2-6}$alkylN$R^aR^h$, —N$R^c$C$_{2-6}$alkylO$R^h$, —C(=O)$R^g$, —C(=O)O$R^g$, —C(=O)N$R^aR^g$, —C(=N$R^a$)N$R^aR^g$, —O$R^g$, —OC(=O)$R^g$, —OC(=O)N$R^aR^g$, —OC(=O)N($R^a$)S(=O)$_2R^g$, —OC(=O)N($R^g$)S(=O)$_2R^e$, —OC$_{2-6}$alkylN$R^aR^g$, —OC$_{2-6}$alkylO$R^g$, —S$R^g$, —S(=O)$R^g$, —S(=O)$_2R^g$, —S(=O)$_2NR^aR^g$, —S(=O)$_2$N($R^g$)C(=O)$R^e$, —S(=O)$_2$N($R^a$)C(=O)$R^g$, —S(=O)$_2$N($R^g$)C(=O)O$R^h$, —S(=O)$_2$N($R^a$)C(=O)O$R^g$, —S(=O)$_2$N($R^g$)C(=O)N$R^aR^h$, —S(=O)$_2$N($R^a$)C(=O)N$R^aR^g$, —N$R^aR^g$, —N($R^g$)C(=O)$R^e$, —N($R^a$)C(=O)$R^g$, —N($R^g$)C(=O)O$R^h$, —N($R^a$)C(=O)O$R^g$, —N($R^g$)C(=O)N$R^aR^h$, —N($R^a$)C(=O)N$R^aR^g$, —N($R^g$)C(=N$R^a$)N$R^aR^h$, —N($R^a$)C(=N$R^a$)N$R^aR^g$, —N($R^g$)S(=O)$_2R^e$, —N($R^a$)S(=O)$_2R^g$, —N($R^g$)S(=O)$_2NR^aR^h$, —N($R^a$)S(=O)$_2NR^aR^g$, —N$R^h$C$_{2-6}$alkylN$R^aR^g$, —N$R^a$C$_{2-6}$alkylN$R^aR^g$, —N$R^g$C$_{2-6}$alkylO$R^h$ and —N$R^c$C$_{2-6}$alkylO$R^g$.

In another embodiment, in conjunction with any one of the above and below embodiments, $R^4$ is $R^c$ substituted by 0, 1, 2, 3 or 4 substituents selected from $R^c$, $R^e$, halo, $C_{1-4}$haloalkyl, cyano, nitro, —C(=O)$R^e$, —C(=O)O$R^h$, —C(=O)N$R^aR^h$, —C(=N$R^a$)N$R^aR^h$, —O$R^h$, —OC(=O)$R^e$, —OC(=O)N$R^aR^h$, —OC(=O)N($R^a$)S(=O)$_2R^e$, —OC$_{2-6}$alkylN$R^aR^h$, —OC$_{2-6}$alkylO$R^h$, —S$R^e$, —S(=O)$R^e$, —S(=O)$_2R^e$, —S(=O)$_2NR^aR^h$, —S(=O)$_2$N($R^a$)C(=O)$R^e$, —S(=O)$_2$N($R^a$)C(=O)O$R^h$, —S(=O)$_2$N($R^a$)C(=O)N$R^aR^h$, —N$R^aR^h$, —N($R^a$)C(=O)$R^e$, —N($R^a$)C(=O)O$R^h$, —N($R^a$)C(=O)N$R^aR^h$, —N($R^a$)C(=N$R^a$)N$R^aR^h$, —N($R^a$)S(=O)$_2R^e$, —N($R^a$)S(=O)$_2NR^aR^h$, —N$R^c$C$_{2-6}$alkylN$R^aR^h$, —N$R^c$C$_{2-6}$alkylO$R^h$, —C(=O)$R^g$, —C(=O)O$R^g$, —C(=O)N$R^aR^g$, —C(=N$R^a$)N$R^aR^g$, —O$R^g$, —OC(=O)$R^g$, —OC(=O)N$R^aR^g$, —OC(=O)N($R^a$)S(=O)$_2R^g$, —OC(=O)N($R^g$)S(=O)$_2R^e$, —OC$_{2-6}$alkylN$R^aR^g$, —OC$_{2-6}$alkylO$R^g$, —S$R^g$, —S(=O)$R^g$, —S(=O)$_2R^g$, —S(=O)$_2NR^aR^g$, —S(=O)$_2$N($R^g$)C(=O)$R^e$, —S(=O)$_2$N($R^a$)C(=O)$R^g$, —S(=O)$_2$N($R^g$)C(=O)O$R^h$, —S(=O)$_2$N($R^a$)C(=O)O$R^g$, —S(=O)$_2$N($R^g$)C(=O)N$R^aR^h$, —S(=O)$_2$N($R^a$)C(=O)N$R^aR^g$, —N$R^aR^g$, —N($R^g$)C(=O)$R^e$, —N($R^a$)C(=O)$R^g$, —N($R^g$)C(=O)O$R^h$, —N($R^a$)C(=O)O$R^g$, —N($R^g$)C(=O)N$R^aR^h$, —N($R^a$)C(=O)N$R^aR^g$, —N($R^g$)C (=NR$^a$)NR$^a$R$^h$, —N(R$^a$)C(=NR$^a$)NR$^a$R$^g$, —N(R$^g$)S(=O)$_2$ R$^e$, —N(R$^a$)S(=O)$_2$R$^g$, —N(R$^g$)S(=O)$_2$NR$^a$R$^h$, —N(R$^a$)S(=O)$_2$NR$^a$R$^g$, —NR$^h$C$_{2-6}$alkylNR$^a$R$^g$, —NR$^a$C$_{2-6}$ alkylNR$^a$R$^g$, —NR$^g$C$_{2-6}$alkylOR$^h$ and —NR$^a$C$_{2-6}$ alkylOR$^g$, wherein R$^4$ is not imidazole or any substituted derivative thereof.

In another embodiment, in conjunction with any one of the above and below embodiments, R$^4$ is R$^c$ substituted by 1, 2, 3 or 4 substituents selected from R$^c$, R$^e$, halo, C$_{1-4}$haloalkyl, cyano, nitro, —C(=O)R$^e$, —C(=O)OR$^h$, —C(=O)NR$^a$R$^h$, —C(=NR$^a$)NR$^a$R$^h$, —OR$^h$, —OC(=O)R$^e$, —OC(=O)NR$^a$R$^h$, —OC(=O)N(R$^a$)S(=O)$_2$R$^e$, —OC$_{2-6}$alkylNR$^a$R$^h$, —OC$_{2-6}$alkylOR$^h$, —SR$^e$, —S(=O)R$^e$, —S(=O)$_2$R$^e$, —S(=O)$_2$NR$^a$R$^h$, —S(=O)$_2$N(R$^a$)C(=O)R$^e$, —S(=O)$_2$N(R$^a$)C(=O)OR$^h$, —S(=O)$_2$N(R$^a$)C(=O)NR$^a$R$^h$, —NR$^a$R$^h$, —N(R$^a$)C(=O)R$^e$, —N(R$^a$)C(=O)OR$^h$, —N(R$^a$)C(=O)NR$^a$R$^h$, —N(R$^a$)C(=NR$^a$)NR$^a$R$^h$, —N(R$^a$)S(=O)$_2$R$^e$, —N(R$^a$)S(=O)$_2$NR$^a$R$^h$, —NR$^a$C$_{2-6}$alkylNR$^a$R$^h$, —NR$^a$C$_{2-6}$alkylOR$^h$, —C(=O)R$^g$, —C(=O)OR$^g$, —C(=O)NR$^a$R$^g$, —C(=NR$^a$)NR$^a$R$^g$, —OR$^g$, —OC(=O)R$^g$, —OC(=O)NR$^a$R$^g$, —OC(=O)N(R$^a$)S(=O)$_2$R$^g$, —OC(=O)N(R$^g$)S(=O)$_2$R$^e$, —OC$_{2-6}$alkylNR$^a$R$^g$, —OC$_{2-6}$alkylOR$^g$, —SR$^g$, —S(=O)R$^g$, —S(=O)$_2$R$^g$, —S(=O)$_2$NR$^a$R$^g$, —S(=O)$_2$N(R$^g$)C(=O)R$^e$, —S(=O)$_2$N(R$^a$)C(=O)R$^g$, —S(=O)$_2$N(R$^g$)C(=O)OR$^h$, —S(=O)$_2$N(R$^a$)C(=O)OR$^g$, —S(=O)$_2$N(R$^g$)C(=O)NR$^a$R$^h$, —S(=O)$_2$N(R$^a$)C(=O)NR$^a$R$^g$, —NR$^a$R$^g$, —N(R$^g$)C(=O)R$^e$, —N(R$^a$)C(=O)R$^g$, —N(R$^g$)C(=O)OR$^h$, —N(R$^a$)C(=O)OR$^g$, —N(R$^g$)C(=O)NR$^a$R$^h$, —N(R$^a$)C(=O)NR$^a$R$^g$, —N(R$^g$)C(=NR$^a$)NR$^a$R$^h$, —N(R$^a$)C(=NR$^a$)NR$^a$R$^g$, —N(R$^g$)S(=O)$_2$ R$^e$, —N(R$^a$)S(=O)$_2$R$^g$, —N(R$^g$)S(=O)$_2$NR$^a$R$^h$, —N(R$^a$)S(=O)$_2$NR$^a$R$^g$, —NR$^h$C$_{2-6}$alkylNR$^a$R$^g$, —NR$^a$C$_{2-6}$ alkylNR$^a$R$^g$, —NR$^g$C$_{2-6}$alkylOR$^h$ and —NR$^a$C$_{2-6}$ alkylOR$^g$, wherein R$^4$ is not imidazole or any substituted derivative thereof.

In another embodiment, in conjunction with any one of the above and below embodiments, R$^4$ is R$^c$, wherein R$^4$ is not imidazole or any substituted derivative thereof.

In another embodiment, in conjunction with any one of the above and below embodiments, R$^4$ is a ring selected from thiophene, pyrrole, 1,3-oxazole, 1,3-thiazole, 1,3,4-oxadiazole, 1,3,4-thiadiazole, 1,2,3-oxadiazole, 1,2,3-thiadiazole, 1H-1,2,3-triazole, isothiazole, 1,2,4-oxadiazole, 1,2,4-thiadiazole, 1,2,3,4-oxatriazole, 1,2,3,4-thiatriazole, 1H-1,2,4-tetraazole, 1,2,3,5-oxatriazole, 1,2,3,5-thiatriazole, furan, imidazol-1-yl, imidazol-4-yl, 1,2,4-triazol-4-yl, 1,2,4-triazol-5-yl, isoxazol-3-yl, isoxazol-5-yl, thiolane, pyrrolidine, tetrahydrofuran, 4,5-dihydrothiophene, 2-pyrroline, 4,5-dihydrofuran, pyridazine, pyrimidine, pyrazine, 1,2,3-triazine, 1,2,4-triazine, 1,2,4-triazine, 1,3,5-triazine, pyridine, 2H-3,4,5,6-tetrahydropyran, thiane, 1,2-diazaperhydroine, 1,3-diazaperhydroine, piperazine, 1,3-oxazaperhydroine, morpholine, 1,3-thiazaperhydroine, 1,4-thiazaperhydroine, piperidine, 2H-3,4-dihydropyran, 2,3-dihydro-4H-thiin, 1,4,5,6-tetrahydropyridine, 2H-5,6-dihydropyran, 2,3-dihydro-6H-thiin, 1,2,5,6-tetrahydropyridine, 3,4,5,6-tetrahydropyridine, 4H-pyran, 4H-thiin, 1,4-dihydropyridine, 1,4-dithiane, 1,4-dioxane, 1,4-oxathiane, 1,2-oxazolidine, 1,2-thiazolidine, pyrazolidine, 1,3-oxazolidine, 1,3-thiazolidine, imidazolidine, 1,2,4-oxadiazolidine, 1,3,4-oxadiazolidine, 1,2,4-thiadiazolidine, 1,3,4-thiadiazolidine, 1,2,4-triazolidine, 2-imidazoline, 3-imidazoline, 2-pyrazoline, 4-imidazoline, 2,3-dihydroisothiazole, 4,5-dihydroisoxazole, 4,5-dihydroisothiazole, 2,5-dihydroisoxazole, 2,5-dihydroisothiazole, 2,3-dihydrooxazole, 4,5-dihydrooxazole, 2,3-dihydrooxazole, 2,5-dihydrooxazole, 4,5-dihydrothiazole, 2,3-dihydrothiazole, 2,5-dihydrothiazole, 1,3,4-oxathiazolidine, 1,4,2-oxathiazolidine, 2,3-dihydro-1H-[1,2,3]triazole, 2,5-dihydro-1H-[1,2,3]triazole, 4,5-dihydro-1H-[1,2,3]triazole, 2,3-dihydro-1H-[1,2,4]triazole, 4,5-dihydro-1H-[1,2,4]triazole, 2,3-dihydro-[1,2,4]oxadiazole, 2,5-dihydro-[1,2,4]oxadiazole, 4,5-dihydro-[1,2,4]oxadiazole, 2,3-dihydro-[1,2,4]thidiazole, 2,5-dihydro-[1,2,4]thiadiazole, 4,5-dihydro-[1,2,4]thiadiazole, 2,5-dihydro-[1,2,4]oxadiazole, 2,3-dihydro-[1,2,4]oxadiazole, 4,5-dihydro-[1,2,4]oxadiazole, 2,5-dihydro-[1,2,4]thiadiazole, 2,3-dihydro-[1,2,4]thiadiazole, 4,5-dihydro-[1,2,4]thiadiazole, 2,3-dihydro-[1,3,4]oxadiazole, 2,3-dihydro-[1,3,4]thiadiazole, [1,4,2]oxathiazole, [1,3,4]oxathiazole, 1,3,5-triazaperhydroine, 1,2,4-triazaperhydroine, 1,4,2-dithiazaperhydroine, 1,4,2-dioxazaperhydroine, 1,3,5-oxadiazaperhydroine, 1,2,5-oxadiazaperhydroine, 1,3,4-thiadiazaperhydroine, 1,3,5-thiadiazaperhydroine, 1,2,5-thiadiazaperhydroine, 1,3,4-oxadiazaperhydroine, 1,4,3-oxathiazaperhydroine, 1,4,2-oxathiazaperhydroine, 1,4,5,6-tetrahydropyridazine, 1,2,3,4-tetrahydropyridazine, 1,2,3,6-tetrahydropyridazine, 1,2,5,6-tetrahydropyrimidine, 1,2,3,4-tetrahydropyrimidine, 1,4,5,6-tetrahydropyrimidine, 1,2,3,6-tetrahydropyrazine, 1,2,3,4-tetrahydropyrazine, 5,6-dihydro-4H-[1,2]oxazine, 5,6-dihydro-2H-[1,2]oxazine, 3,6-dihydro-2H-[1,2]oxazine, 3,4-dihydro-2H-[1,2]oxazine, 5,6-dihydro-4H-[1,2]thiazine, 5,6-dihydro-2H-[1,2]thiazine, 3,6-dihydro-2H-[1,2]thiazine, 3,4-dihydro-2H-[1,2]thiazine, 5,6-dihydro-2H-[1,3]oxazine, 5,6-dihydro-4H-[1,3]oxazine, 3,6-dihydro-2H-[1,3]oxazine, 3,4-dihydro-2H-[1,3]oxazine, 3,6-dihydro-2H-[1,4]oxazine, 3,4-dihydro-2H-[1,4]oxazine, 5,6-dihydro-2H-[1,3]thiazine, 5,6-dihydro-4H-[1,3]thiazine, 3,6-dihydro-2H-[1,3]thiazine, 3,4-dihydro-2H-[1,3]thiazine, 3,6-dihydro-2H-[1,4]thiazine, 3,4-dihydro-2H-[1,4]thiazine, 1,2,3,6-tetrahydro-[1,2,4]triazine, 1,2,3,4-tetrahydro-[1,2,4]triazine, 1,2,3,4-tetrahydro-[1,3,5]triazine, 2,3,4,5-tetrahydro-[1,2,4]triazine, 1,4,5,6-tetrahydro-[1,2,4]triazine, 5,6-dihydro-[1,4,2]dioxazine, 5,6-dihydro-[1,4,2]dioxazine, 5,6-dihydro-[1,4,2]dithiazine, 2,3-dihydro-[1,4,2]dioxazine, 3,4-dihydro-2H-[1,3,4]oxadiazine, 3,6-dihydro-2H-[1,3,4]oxadiazine, 3,4-dihydro-2H-[1,3,5]oxadiazine, 3,6-dihydro-2H-[1,3,5]oxadiazine, 5,6-dihydro-2H-[1,2,5]oxadiazine, 5,6-dihydro-4H-[1,2,5]oxadiazine, 3,4-dihydro-2H-[1,3,4]thiadiazine, 3,6-dihydro-2H-[1,3,4]thiadiazine, 3,4-dihydro-2H-[1,3,5]thiadiazine, 3,6-dihydro-2H-[1,3,5]thiadiazine, 5,6-dihydro-2H-[1,2,5]thiadiazine, 5,6-dihydro-4H-[1,2,5]thiadiazine, 5,6-dihydro-2H-[1,2,3]oxadiazine, 3,6-dihydro-2H-[1,2,5]oxadiazine, 5,6-dihydro-4H-[1,3,4]oxadiazine, 3,4-dihydro-2H-[1,2,5]oxadiazine, 5,6-dihydro-2H-[1,2,3]thiadiazine, 3,6-dihydro-2H-[1,2,5]thiadiazine, 5,6-dihydro-4H-[1,3,4]thiadiazine, 3,4-dihydro-2H-[1,2,5]thiadiazine, 5,6-dihydro-[1,4,3]oxathiazine, 5,6-dihydro-[1,4,2]oxathiazine, 2,3-dihydro-[1,4,3]oxathiazine, 2,3-dihydro-[1,4,2]oxathiazine, 4,5-dihydropyridine, 1,6-dihydropyridine, 5,6-dihydropyridine, 2H-pyran, 2H-thiin, 3,6-dihydropyridine, 2,3-dihydropyridazine, 2,5-dihydropyridazine, 4,5-dihydropyridazine, 1,2-dihydropyridazine, 2,3-dihydropyrimidine, 2,5-dihydropyrimidine, 5,6-dihydropyrimidine, 3,6-dihydropyrimidine, 4,5-dihydropyrazine, 5,6-dihydropyrazine, 3,6-dihydropyrazine, 4,5-dihydropyrazine, 1,4-dihydropyrazine, 1,4-dithiin, 1,4-dioxin, 2H-1,2-oxazine, 6H-1,2-oxazine, 4H-1,2-oxazine, 2H-1,3-oxazine, 4H-1,3-oxazine, 6H-1,3-oxazine, 2H-1,4-oxazine, 4H-1,4-oxazine, 2H-1,3-thiazine, 2H-1,4-thiazine, 4H-1,2-thiazine, 6H-1,3-thiazine, 4H-1,4-thiazine, 2H-1,2-thiazine, 6H-1,2-thiazine, 1,4-oxathiin, 2H,5H-1,2,3-triazine, 1H,4H-1,2,3-triazine, 4,5-dihydro-1,2,3-triazine, 1H,6H-1,2,3-triazine, 1,2-dihydro-1,2,3-triazine, 2,3-dihydro-1,2,4-triazine, 3H,6H-1,2,4-triazine, 1H,6H-1,2,4-triazine, 3,4-dihydro-1,2,4-triazine, 1H,4H-1,2,4-triazine, 5,6-dihydro-1,2,4-triazine, 4,5-dihydro-1,2,4-triazine, 2H,5H-1,2, 4-triazine, 1,2-dihydro-1,2,4-triazine, 1H,4H-1,3,5-triazine, 1,2-dihydro-1,3,5-triazine, 1,4,2-dithiazine, 1,4,2-dioxazine, 2H-1,3,4-oxadiazine, 2H-1,3,5-oxadiazine, 6H-1,2,5-oxadiazine, 4H-1,3,4-oxadiazine, 4H-1,3,5-oxadiazine, 4H-1,2,5-oxadiazine, 2H-1,3,5-thiadiazine, 6H-1,2,5-thiadiazine, 4H-1,3,4-thiadiazine, 4H-1,3,5-thiadiazine, 4H-1,2,5-thiadiazine, 2H-1,3,4-thiadiazine, 6H-1,3,4-thiadiazine, 6H-1,3,4-oxadiazine, 1,4,2-oxathiazine and any bicyclic derivative of any of the above rings containing a vicinally-fused phenyl, pyridine or pyrimidine, wherein the carbon atoms of the ring and bicyclic derivative are substituted by 0, 1 or 2 oxo or thioxo groups; wherein the ring or bicyclic derivative there of is substituted by 0, 1, 2, 3 or 4 substituents selected from $R^e$, $R^e$, halo, $C_{1-4}$haloalkyl, cyano, nitro, —C(=O)$R^e$, —C(=O)O$R^h$, —C(=O)NR$^a$R$^h$, —C(=NR$^a$)NR$^a$R$^h$, —OR$^h$, —OC(=O)R$^e$, —OC(=O)NR$^a$R$^h$, —OC(=O)N(R$^a$)S(=O)$_2$R$^e$, —OC$_{2-6}$alkylNR$^a$R$^h$, —OC$_{2-6}$alkylOR$^h$, —SR$^e$, —S(=O)R$^e$, —S(=O)$_2$R$^e$, —S(=O)$_2$NR$^a$R$^h$, —S(=O)$_2$N(R$^a$)C(=O)R$^e$, —S(=O)$_2$N(R$^a$)C(=O)OR$^h$, —S(=O)$_2$N(R$^a$)C(=O)NR$^a$R$^h$, —NR$^a$R$^h$, —N(R$^a$)C(=O)R$^e$, —N(R$^a$)C(=O)OR$^h$, —N(R$^a$)C(=O)NR$^a$R$^h$, —N(R$^a$)C(=NR$^a$)NR$^a$R$^h$, —N(R$^a$)S(=O)$_2$R$^e$, —N(R$^a$)S(=O)$_2$NR$^a$R$^h$, —NR$^a$C$_{2-6}$alkylNR$^a$R$^h$, —C(=O)R$^g$, —C(=O)OR$^g$, —C(=O)NR$^a$R$^g$, —C(=NR$^a$)NR$^a$R$^g$, —OR$^g$, —OC(=O)R$^g$, —OC(=O)NR$^a$R$^g$, —OC(=O)N(R$^a$)S(=O)$_2$R$^g$, —OC(=O)N(R$^g$)S(=O)$_2$R$^e$, —OC$_{2-6}$alkylNR$^a$R$^g$, —OC$_{2-6}$alkylOR$^g$, —SR$^g$, —S(=O)R$^g$, —S(=O)$_2$R$^g$, —S(=O)$_2$NR$^a$R$^g$, —S(=O)$_2$N(R$^g$)C(=O)R$^e$, —S(=O)$_2$N(R$^a$)C(=O)R$^g$, —S(=O)$_2$N(R$^g$)C(=O)OR$^h$, —S(=O)$_2$N(R$^a$)C(=O)OR$^g$, —S(=O)$_2$N(R$^g$)C(=O)NR$^a$R$^h$, —S(=O)$_2$N(R$^a$)C(=O)NR$^a$R$^g$, —NR$^a$R$^g$, —N(R$^g$)C(=O)R$^e$, —N(R$^a$)C(=O)R$^g$, —N(R$^g$)C(=O)OR$^h$, —N(R$^a$)C(=O)OR$^g$, —N(R$^g$)C(=O)NR$^a$R$^h$, —N(R$^a$)C(=O)NR$^a$R$^g$, —N(R$^g$)C(=NR$^a$)NR$^a$R$^h$, —N(R$^a$)C(=NR$^a$)NR$^a$R$^g$, —N(R$^g$)S(=O)$_2$R$^e$, —N(R$^a$)S(=O)$_2$R$^g$, —N(R$^g$)S(=O)$_2$NR$^a$R$^h$, —N(R$^a$)S(=O)$_2$NR$^a$R$^g$, —NR$^h$C$_{2-6}$alkylNR$^a$R$^g$, —NR$^a$C$_{2-6}$alkylNR$^a$R$^g$, —NR$^g$C$_{2-6}$alkylOR$^h$ and —NR$^a$C$_{2-6}$alkylOR$^g$.

In another embodiment, in conjunction with any one of the above and below embodiments, $R^5$ is, independently, in each instance, H or $C_{1-3}$alkyl.

In another embodiment, in conjunction with any one of the above and below embodiments, $R^{5'}$ is, independently, in each instance, H or $C_{1-3}$alkyl.

In another embodiment, in conjunction with any one of the above and below embodiments, $R^6$ is phenyl vicinally fused with a 5-, 6- or 7-membered saturated, partially-saturated or unsaturated ring containing 0, 1, 2 or 3 heteroatoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from $C_{1-8}$alkyl, $C_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —C(=O)R$^b$, —C(=O)NR$^a$R$^a$, —OC(=O)N(R$^a$)S(=O)$_2$R$^b$, —OC$_{2-6}$alkylNR$^a$R$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and the ring is additionally substituted by 0, 1, 2, 3 or 4 substituents independently selected from Br, Cl, F and I.

In another embodiment, in conjunction with any one of the above and below embodiments, $R^6$ is naphthyl, quinolinyl, isoquinolinyl or 5,6,7,8-tetrahydronaphthyl substituted by 0, 1, 2 or 3 substituents selected from $C_{1-8}$alkyl, $C_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by 0, 1, 2, 3, 4 or 5 substituents independently selected from Br, Cl, F and I.

Another aspect of the invention relates to a method of treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound according to any of the above embodiments.

Another aspect of the invention relates to a pharmaceutical composition comprising a compound according to any of the above embodiments and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders.

The compounds of this invention may have in general several asymmetric centers and are typically depicted in the form of racemic mixtures. This invention is intended to encompass racemic mixtures, partially racemic mixtures and separate enantiomers and diasteromers.

Unless otherwise specified, the following definitions apply to terms found in the specification and claims:

"$C_{\alpha-\beta}$alkyl" means an alkyl group comprising a minimum of α and a maximum of β carbon atoms in a branched, cyclical or linear relationship or any combination of the three, wherein α and β represent integers. The alkyl groups described in this section may also contain one or two double or triple bonds. Examples of $C_{1-6}$alkyl include, but are not limited to the following:

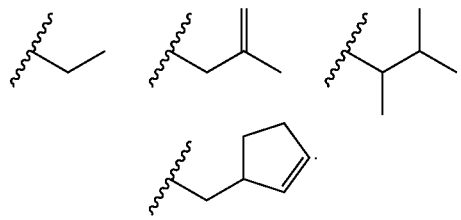

"Benzo group", alone or in combination, means the divalent radical $C_4H_4=$, one representation of which is —CH=CH—CH=CH—, that when vicinally attached to another ring forms a benzene-like ring—for example tetrahydronaphthylene, indole and the like.

"Halo" or "halogen" means a halogen atoms selected from F, Cl, Br and I. "$C_{V-W}$haloalkyl" means an alkyl group, as described above, wherein any number—at least one—of the hydrogen atoms attached to the alkyl chain are replaced by F, Cl, Br or I.

"Heterocycle" means a ring comprising at least one carbon atom and at least one other atom selected from N, O and S. Examples of heterocycles that may be found in the claims include, but are not limited to, the following:

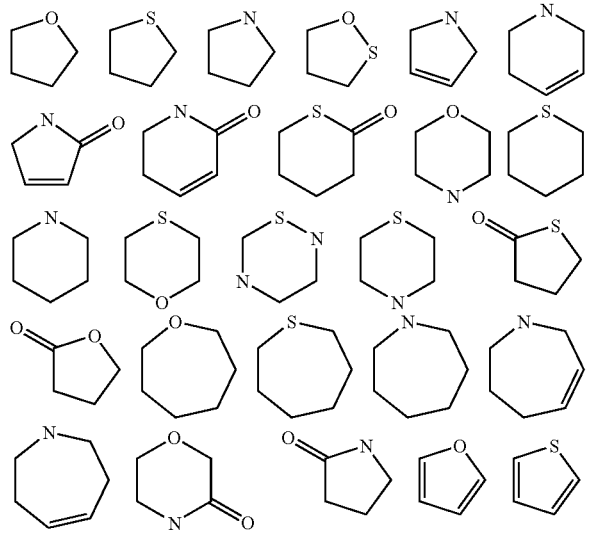

-continued

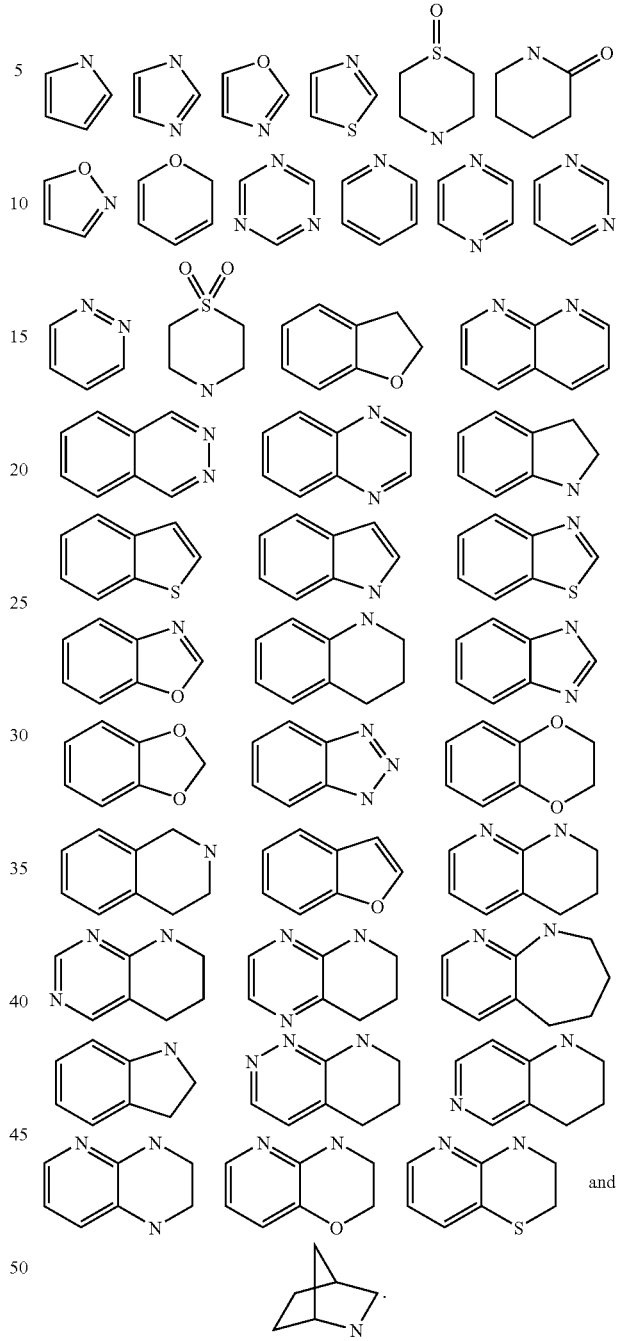

"Available nitrogen atoms" are those nitrogen atoms that are part of a heterocycle and are joined by two single bonds (e.g. piperidine), leaving an external bond available for substitution by, for example, H or $CH_3$.

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

The symbol ===== indicates a single or double bond.

"Saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyldimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

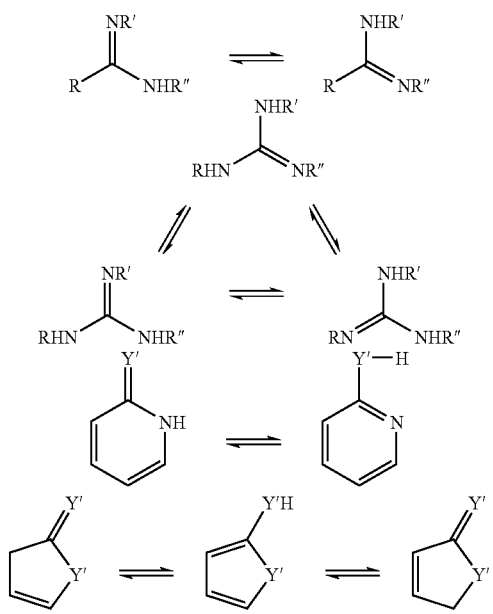

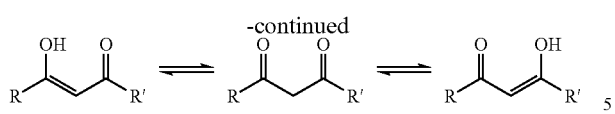

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

EXPERIMENTAL

Unless otherwise noted, all materials were obtained from commercial suppliers and used without further purification. All parts are by weight and temperatures are in degrees centigrade unless otherwise indicated. All microwave assisted reactions were conducted with a Smith Synthesizer from Personal Chemistry, Uppsala, Sweden. All compounds showed NMR spectra consistent with their assigned structures. Melting points were determined on a Buchi apparatus and are uncorrected. Mass spectral data was determined by electrospray ionization technique. All examples were purified to >90% purity as determined by high-performance liquid chromatography. Unless otherwise stated, reactions were run at RT.

The following abbreviations are used:
DMSO—dimethyl sulfoxide
DMF—N,N-dimethylformamide
THF—tetrahydrofuran
$Et_2O$—diethyl ether
EtOAc—ethyl acetate
MeOH—methyl alcohol
EtOH—ethyl alcohol
MeCN—acetonitrile
MeI—iodomethane
NMP—1-methyl-2-pyrrolidinone
DCM—dichloromethane
TFA—trifluoroacetic acid
Sat.—saturated
h—hour
min—minutes
mL milliliters
g grams
mg milligrams
RT room temperature

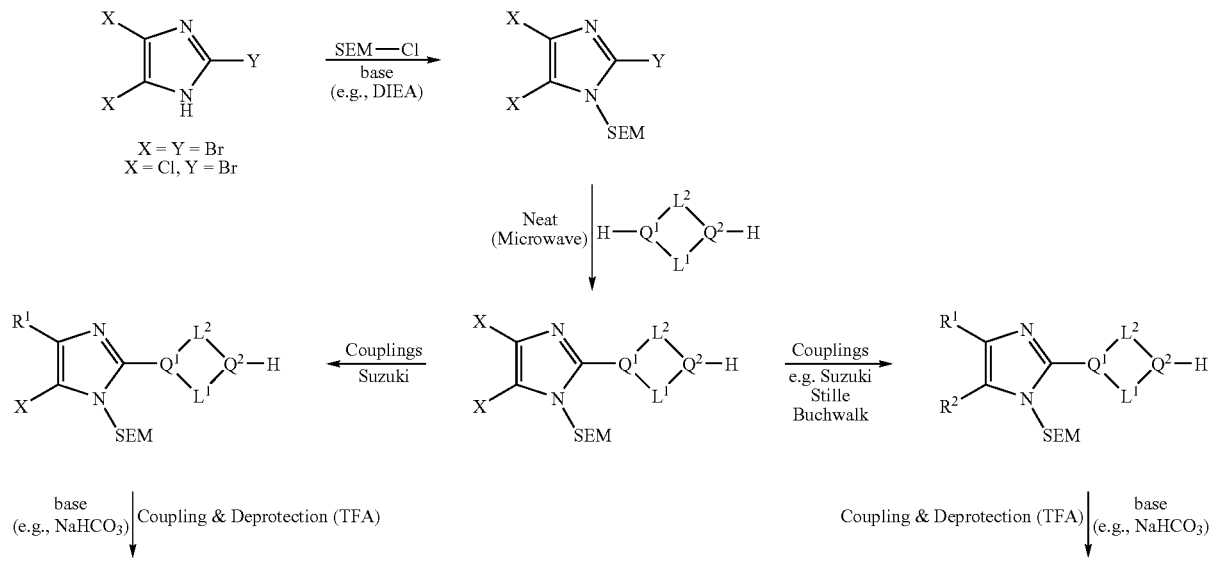

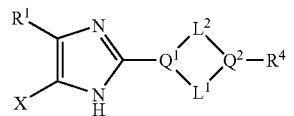

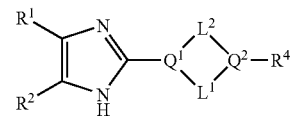

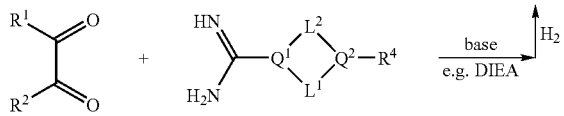

EXAMPLE 1

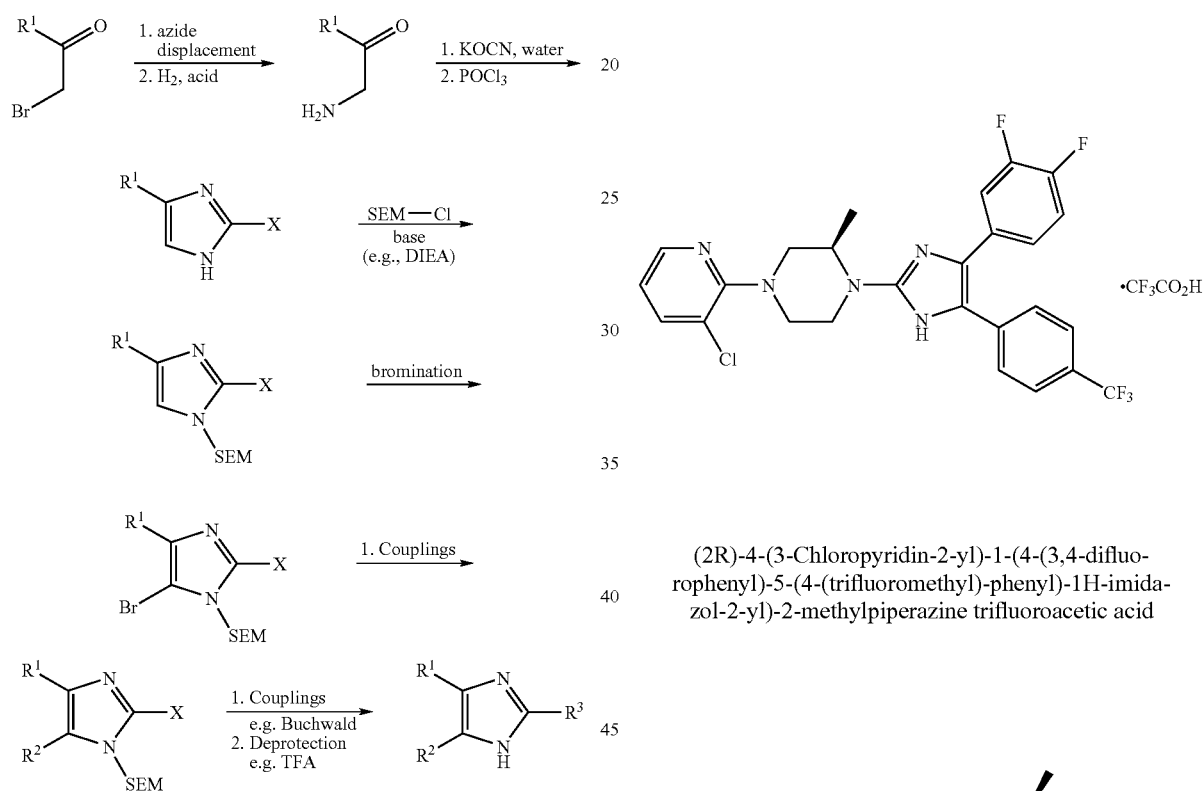

(2R)-4-(3-Chloropyridin-2-yl)-1-(4-(3,4-difluorophenyl)-5-(4-(trifluoromethyl)-phenyl)-1H-imidazol-2-yl)-2-methylpiperazine trifluoroacetic acid

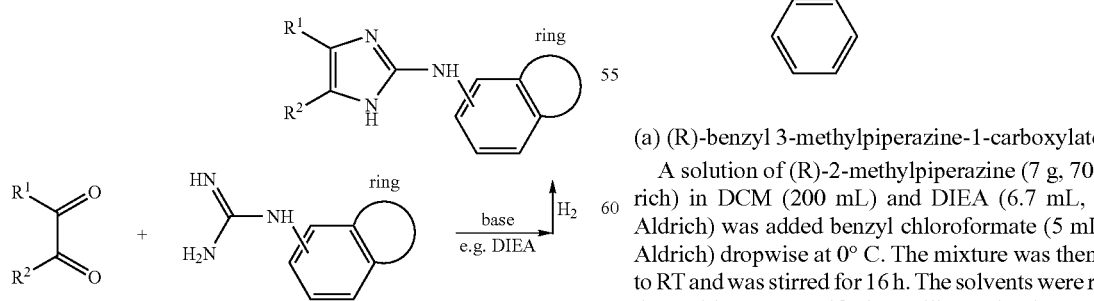

(a) (R)-benzyl 3-methylpiperazine-1-carboxylate

A solution of (R)-2-methylpiperazine (7 g, 70 mmol, Aldrich) in DCM (200 mL) and DIEA (6.7 mL, 38.5 mmol, Aldrich) was added benzyl chloroformate (5 mL, 35 mmol, Aldrich) dropwise at 0° C. The mixture was then warmed up to RT and was stirred for 16 h. The solvents were removed and the residue was purified on silica gel using ISCO Combiflash® system with DCM/2M methanolic ammonia gradient to give the title compound as light yellow oil. MS (ESI, positive ion) m/z: 235 (M+1).

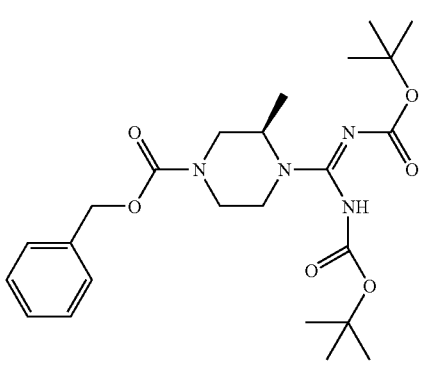

(b) (R,E)-benzyl 4-(N,N'-(bis(tert-butoxycarbonyl))carbamimidoyl)-3-methylpiperazine-1-carboxylate A mixture of (R)-benzyl 3-methylpiperazine-1-carboxylate (4.8 g, 20.5 mmol) from step (a) above, 1,3-bis(tertbutoxycarbonyl)-2-methylisothiourea (6.5 g, 23 mmol, Aldrich), and triethylamine (3.4 mL, 24.6 mmol, Aldrich) in DCM (140 mL) was added mercury(II)chloride (5.8 g, 21.6 mmol, Aldrich). The reaction mixture was stirred at RT for 16 h. Then, the mixture was filtered and the solid was washed with DCM (2×100 mL). The combined filtrates were concentrated in vacuo and the residue was purified on silica gel using ISCO Combiflash® system with DCM/2M methanolic ammonia gradient to give the title compound as a white solid. MS (ESI, positive ion) m/z: 477 (M+1).

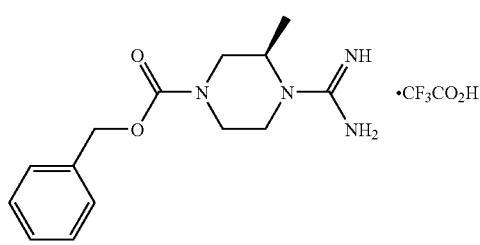

(c) (R)-benzyl 4-carbamimidoyl-3-methylpiperazine-1-carboxylate, trifluoroacetic acid salt A solution of (R,E)-benzyl 4-(N,N'-(bis(tert-butoxycarbonyl))carbamimidoyl)-3-methylpiperazine-1-carboxylate from step (b) above (8.8 g, 18 mmol) in TFA (13.2 mL) and DCM (50 mL) was stirred at RT for 7 h. The solvents were removed and the residue was purified on silica gel using ISCO Combiflash® system with DCM/2M methanolic ammonia gradient to give the title compound as a white solid. MS (ESI, positive ion) m/z: 277 (M+1).

(d) (2R)-1-(4-(3,4-difluorophenyl)-5-(4-(trifluoromethyl)phenyl)-1H-imidazol-2-yl)-2-methylpiperazine, trifluoroacetic acid salt A mixture of (R)-benzyl 4-carbamimidoyl-3-methylpiperazine-1-carboxylate from step (c) above (1.52 g, 5.51 mmol) and 1-(4-(trifluoromethyl)phenyl)-2-(3,4,5-trifluorophenyl)ethane-1,2-dione (1.22 g, 3.67 mmol, Example 39(b)) in MeOH (24 mL) was stirred at RT for 16 h. Then, ammonium formate (6.9 g, 110 mmol, Aldrich) and palladium(II) hydroxide (300 mg) were added. The mixture was heated to 65° C. for 48 h. Then, the mixture was cooled to RT and was filtered through a CELITE® pad. The filter cake was washed with MeOH (2×10 mL) and the filtrate was concentrated. The residue was dissolved in MeOH (20 mL) and purified by preparative HPLC [gradient 10-85% MeCN (0.1% TFA)/H₂O (0.1% TFA)] to give the title compound as a white solid. MS (ESI, positive ion) m/z: 423 (M+1).

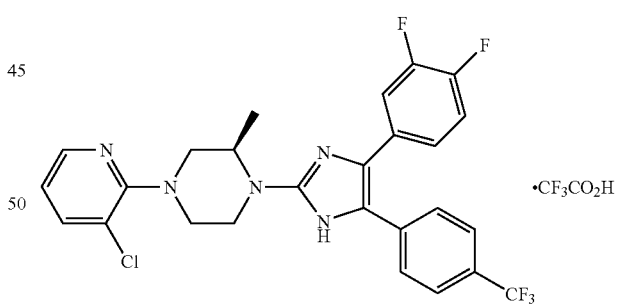

(e) (2R)-4-(3-chloropyridin-2-yl)-1-(4-(3,4-difluorophenyl)-5-(4-(trifluoromethyl)phenyl)-1H-imidazol-2-yl)-2-methylpiperazine, trifluoroacetic acid salt.

A mixture of (2R)-1-(4-(3,4-difluorophenyl)-5-(4-(trifluoromethyl)phenyl)-1H-imidazol-2-yl)-2-methylpiperazine from step (d) above (150 mg, 0.355 mmol), 2,3-dichloropyridine (104 mg, 0.71 mmol, Lancaster), and sodium bicarbonate (89 mg, 1.1 mmol, Mallinckrodt) in NMP (1.2 mL) was reacted under the condition of Example 12(a) to give the title compound as a tan solid. MS (ESI, positive ion) m/z: 534 (M+1).

EXAMPLE 2

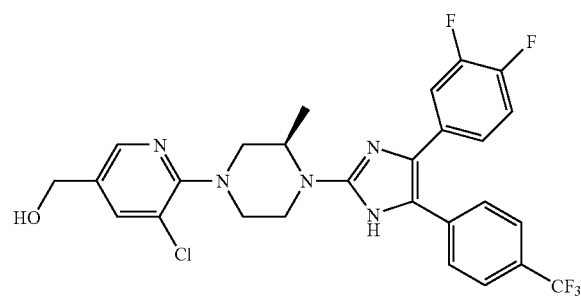

(5-Chloro-6-((R)-4-(4-(3,4-difluorophenyl)-5-(4-(trifluoromethyl)phenyl)-1H-imidazol-2-yl)-3-methylpiperazin-1-yl)pyridin-3-yl)methanol

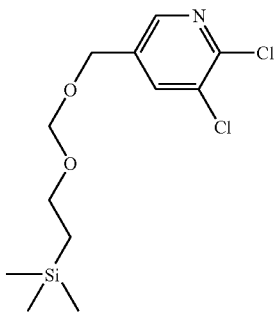

(a) 2,3-Dichloro-5-(((2-(trimethylsilyl)ethoxy)methoxy)methyl)pyridine

To a mixture of sodium hydride (542 mg, 22.6 mmol, Aldrich) and (2-(chloromethoxy)ethyl)trimethylsilane (4 mL, 23 mmol, Aldrich) in THF (20 mL) was added a solution of (5,6-dichloropyridin-3-yl)methanol (2 g, 11 mmol, Lancaster) in THF (15 mL) dropwise at 0° C. The mixture was then allowed to warm up to RT and was stirred for 14 h. Then, H₂O (50 mL) was added dropwise at 0° C. and EtOAc (150 mL) was added at RT. The mixture was stirred at RT for 0.5 h and two separated layers were observed. The organic layer was collected, dried over MgSO₄, and concentrated in vacuo. The residue was purified on silica gel using ISCO Combiflash® system with EtOAc/Hexanes (1:2) as the eluant to give the title compound as colorless oil. MS (ESI, positive ion) m/z: 308 (M+1).

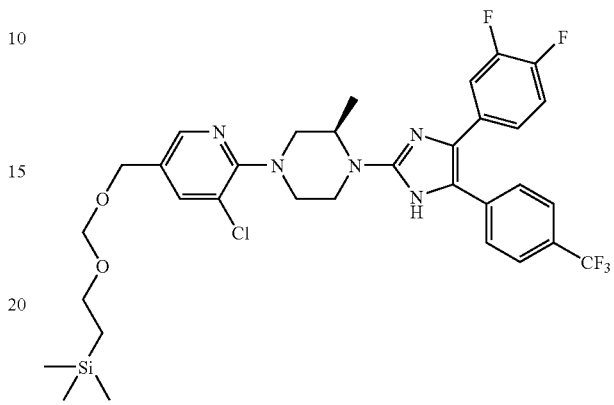

(b) (2R)-4-(3-Chloro-5-(((2-(trimethylsilyl)ethoxy)methoxy)methyl)pyridin-2-yl)-1-(4-(3,4-difluorophenyl)-5-(4-(trifluoromethyl)phenyl)-1H-imidazol-2-yl)-2-methylpiperazine A mixture of 2,3-dichloro-5-(((2-(trimethylsilyl)ethoxy)methoxy)methyl)pyridine from step (a) above (80 mg, 0.26 mmol), (2R)-1-(4-(3,4-difluorophenyl)-5-(4-(trifluoromethyl)phenyl)-1H-imidazol-2-yl)-2-methylpiperazine (100. mg, 0.236 mmol, Example 1(d)), and DIEA (0.082 mL, 0.47 mmol, Aldrich) in NMP (0.7 mL) was subjected to microwave irradiation at 170° C. for 1 h. The mixture was filtered and the filtrate was concentrated in vacuo. The residue was purified on silica gel using ISCO Combiflash® system with EtOAc/Hexanes (1:9) as the eluant to give the title compound as a light brown solid. MS (ESI, positive ion) m/z: 694 (M+1).

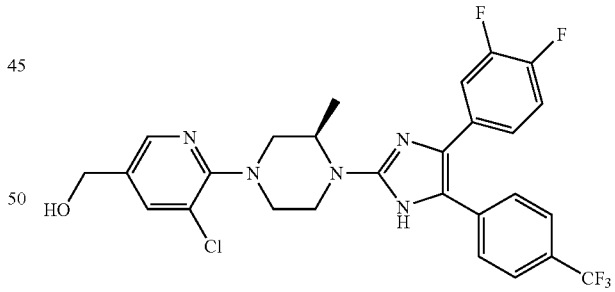

(c) (5-Chloro-6-((R)-4-(4-(3,4-difluorophenyl)-5-(4-(trifluoromethyl)phenyl)-1H-imidazol-2-yl)-3-methylpiperazin-1-yl)pyridin-3-yl)methanol A solution of (2R)-4-(3-chloro-5-(((2-(trimethylsilyl)ethoxy)methoxy)methyl)pyridin-2-yl)-1-(4-(3,4-difluorophenyl)-5-(4-(trifluoromethyl)phenyl)-1H-imidazol-2-yl)-2-methylpiperazine from step (b) above (160 mg, 0.23 mmol) in TFA (3 mL) was stirred at RT for 1.5 h. The solvent was removed and the residue was added solution of MeOH: DCM (1:1, 3 mL). The mixture was cooled to 0° C. and potassium carbonate (200 mg) was added. The mixture was then stirred at RT for 2.5 h and the solvents were removed.

The residue was purified on silica gel using ISCO Combiflash® system with EtOAc/Hexanes (1:1) as the eluant to give the title compound as a light yellow solid. MS (ESI, positive ion) m/z: 564 (M+1).

EXAMPLE 3

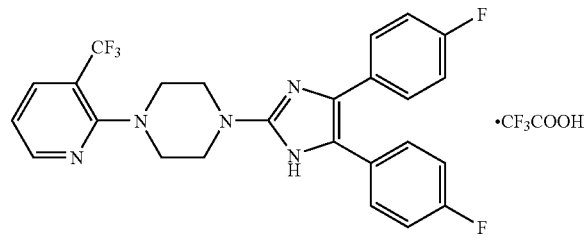

1-(4,5-Bis(4-fluorophenyl)-1H-imidazol-2-yl)-4-(3-(trifluoromethyl)pyridin-2-yl)piperazine, trifluoroacetic acid salt

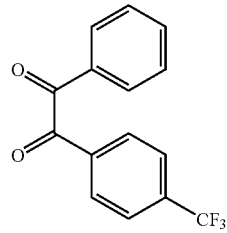

(a) 4-(3-(Trifluoromethyl)pyridin-2-yl)piperazine-1-carboxamidine

To a stirred solution of 1-(3-(trifluoromethyl)pyridin-2-yl)piperazine (1.00 g, 4.35 mmol, Oakwood) and 1,3-bis(benzyloxycarbonyl)-2-methyl-2-thiopseudourea (2.04 g, 5.68 mmol, Aldrich) in DCM (20 mL) was added triethylamine (0.76 g, 7.53 mmol, Aldrich) and mercuric chloride (1.54 g, 5.65 mmol, Aldrich). The reaction mixture was stirred at RT for 2 h and diluted with DCM (150 mL) and water (25 mL). The resulting emulsion was filtered through a Celite® pad and the DCM layer of the filtrate was separated, dried over anhydrous sodium sulfate, and filtered. The filtrate was evaporated in vacuo and the resulting colorless oil was dissolved in ethanol (25 mL). To the solution was added 20% palladium hydroxide on carbon (250 mg, Aldrich) and the mixture was stirred under H₂ atmosphere for 16 h at RT. The reaction mixture was filtered through a Celite® pad, and the filtrate was concentrated in vacuo to give the title compound as a foamy white solid. MS (ESI, pos. ion) m/z: 274 (M+1).

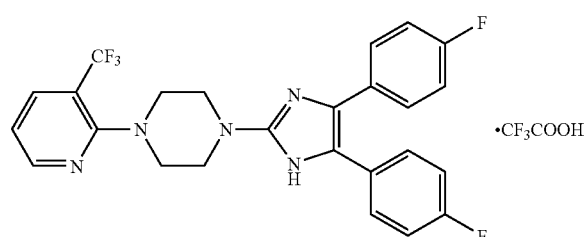

(b) 1-(4,5-Bis(4-fluorophenyl)-1H-imidazol-2-yl)-4-(3-(trifluoromethyl)pyridin-2-yl)piperazine, trifluoroacetic acid salt To a solution of 4-(3-(trifluoromethyl)pyridin-2-yl)piperazine-1-carboxamidine from step (a) above (104 mg, 0.38 mmol) and 1,2-bis(4-fluorophenyl)ethane-1,2-dione (102 mg, 0.41 mmol, Aldrich) in methanol (2 mL) was added N,N-diisopropylethylamine (93 mg, 0.72 mmol, Aldrich), and the mixture was stirred at RT for 21 h. The reaction mixture was diluted with methanol (5 mL) and stirred with 10% palladium on carbon (45 mg, Aldrich) under H₂ atmosphere for 21 h at RT. The reaction mixture was filtered through a Celite® pad, and the filtrate was concentrated in vacuo. The residue was dissolved in MeOH (3 mL) and purified by preparative HPLC [gradient 10-90% MeCN (0.1% TFA)/H₂O (0.1% TFA)] to give the title compound as a white amorphous solid. MS (ESI, pos. ion) m/z: 486 (M+1).

EXAMPLE 4

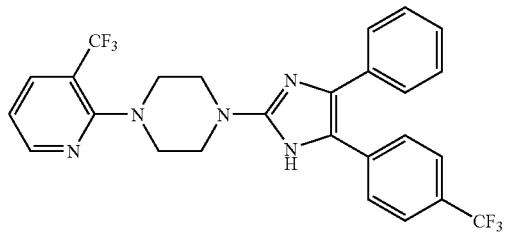

1-(4-Phenyl-5-(4-(trifluoromethyl)phenyl)-1H-imidazol-2-yl)-4-(3-(trifluoromethyl)pyridin-2-yl)piperazine (a) 1-Phenyl-2-(4-(trifluoromethyl)phenyl)ethane-1,2-dione A solution of N-bromosuccinimide (3.87 g, 21.7 mmol, Aldrich) and 2-phenyl-1-(4-(trifluoromethyl)phenyl)ethanone (2.8 g, 10.6 mmol, Rieke Metals) in DMSO (25 mL) was heated to 65° C. for 20 min. The reaction mixture was cooled to RT, and diluted with DCM (75 mL) and water (25 mL). The DCM layer was separated, washed with brine (25 mL), dried over anhydrous sodium sulfate and filtered. The filtrate was evaporated in vacuo and the residue purified by silica gel column chromatography, eluting with EtOAc/hexane (1:10) to afford the title compound as yellow amorphous solid. MS (ESI, pos. ion) m/z: 279 (M+1).

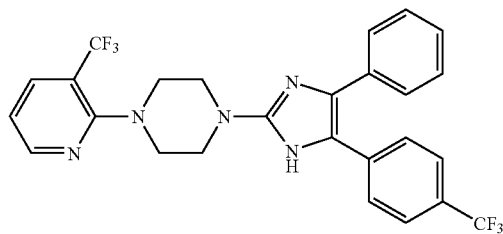

(b) 1-(4-Phenyl-5-(4-(trifluoromethyl)phenyl)-1H-imidazol-2-yl)-4-(3-(trifluoromethyl)pyridin-2-yl)piperazine To a solution of 4-(3-(trifluoromethyl)pyridin-2-yl)piperazine-1-carboxamidine (525 mg, 1.92 mmol, Example 3(a)) and 1-phenyl-2-(4-(trifluoromethyl)phenyl)ethane-1,2-dione from step (a) above (535 mg, 1.92 mmol) in methanol (12 mL) was added N,N-diisopropylethylamine (631 mg, 4.88 mmol, Aldrich), and the mixture stirred at RT for 22 h. The reaction mixture was evaporated and the residue was purified on silica gel column with EtOAc/hexane (1:5) as the eluant to yield the intermediate imidazol-4-ol derivative. This intermediate was dissolved in methanol (15 mL) and stirred with 10% palladium on carbon (70 mg, Aldrich) under $H_2$ atmosphere for 15 h at RT. The reaction mixture was filtered through a Celite® pad, and the filtrate was concentrated in vacuo. The residue was purified on silica gel column chromatography, eluting with EtOAc/hexane (1:5) to give the title compound as a white amorphous solid. MS (ESI, pos. ion) m/z: 518.

EXAMPLE 5

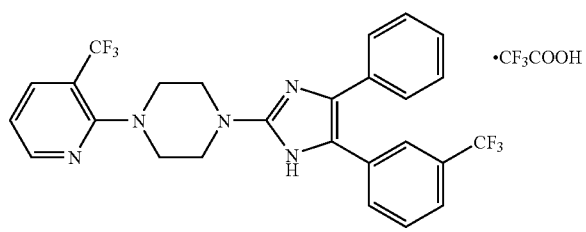

1-(4-Phenyl-5-(3-(trifluoromethyl)phenyl)-1H-imidazol-2-yl)-4-(3-(trifluoromethyl)pyridin-2-yl)piperazine, trifluoroacetic acid salt

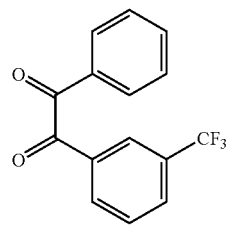

(a) 1-Phenyl-2-(3-(trifluoromethyl)phenyl)ethane-1,2-dione

A solution of N-bromosuccinimide (715 mg, 4.02 mmol, Aldrich) and 2-phenyl-1-(3-(trifluoromethyl)phenyl)ethanone (531 mg, 2.01 mmol, Rieke Metals) in DMSO (8 mL) was heated to 60° C. for 18 h. The reaction mixture was cooled to RT, diluted with DCM (75 mL) and water (15 mL). The DCM layer was separated, washed with brine (25 mL), dried over anhydrous sodium sulfate, and filtered. The filtrate was evaporated in vacuo and the residue purified by silica gel column chromatography, eluting with EtOAc/hexanes (1:10) to afford the title compound as yellow amorphous solid. MS (ESI, pos. ion) m/z: 279 (M+1).

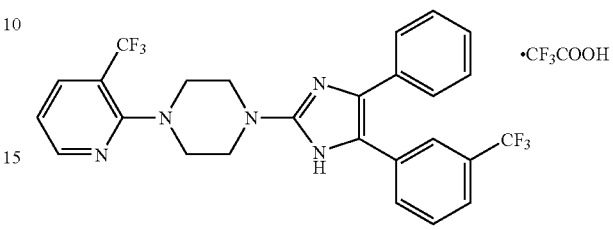

(b) 1-(4-Phenyl-5-(3-(trifluoromethyl)phenyl)-1H-imidazol-2-yl)-4-(3-(trifluoromethyl)pyridin-2-yl)piperazine, trifluoroacetic acid salt 1-Phenyl-2-(3-(trifluoromethyl)phenyl)ethane-1,2-dione from step (a) above (93 mg, 0.33 mmol) reacted with 4-(3-(trifluoromethyl)pyridin-2-yl)piperazine-1-carboxamidine (81 mg, 0.30 mmol, Example 3(a)) under the conditions of Example 3(b). The crude product was purified by preparative HPLC [gradient 10-90% MeCN (0.1% TFA)/$H_2O$ (0.1% TFA)] to give the title compound as a white amorphous solid. MS (ESI, pos. ion) m/z: 518 (M+1).

EXAMPLE 6

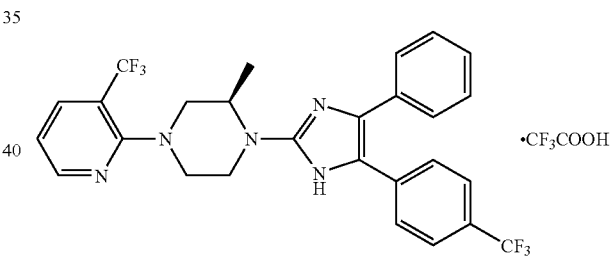

(2R)-2-Methyl-1-(4-phenyl-5-(4-(trifluoromethyl)phenyl)-1H-imidazol-2-yl)-4-(3-(trifluoromethyl)pyridin-2-yl)piperazine, trifluoroacetic acid salt

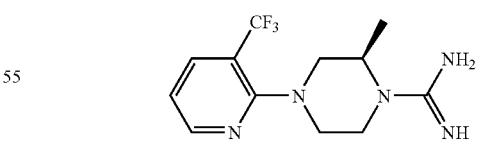

(a) (2R)-2-Methyl-4-(3-(trifluoromethyl)pyridin-2-yl)piperazine-1-carboxamidine (3R)-3-Methyl-1-(3-(trifluoromethyl)pyridin-2-yl)piperazine (1.06 g, 4.31 mmol, WO2004/035549) reacted with 1,3-bis(benzyloxycarbonyl)-2-methyl-2-thiopseudourea under the conditions of Example 3(a) to give 700 mg (96%) of the title compound as a foamy white solid. MS (ESI, pos. ion) m/z: 288 (M+1).

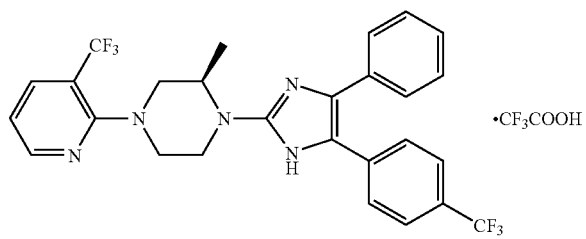

(b) (2R)-2-Methyl-1-(4-phenyl-5-(4-(trifluoromethyl)phenyl)-1H-imidazol-2-yl)-4-(3-(trifluoromethyl)pyridin-2-yl)piperazine, trifluoroacetic acid salt (2R)-2-Methyl-4-(3-(trifluoromethyl)pyridin-2-yl)piperazine-1-carboxamidine from step (a) above (380 mg, 1.32 mmol) reacted with 1-phenyl-2-(4-(trifluoromethyl)phenyl)ethane-1,2-dione (310 mg, 1.11 mmol, Example 4(a)) under the conditions of Example 4(b). The crude product was purified by preparative HPLC [gradient 10-90% MeCN (0.1% TFA)/H$_2$O (0.1% TFA)] to give the title compound as an amorphous solid. MS (ESI, pos. ion) m/z: 532 (M+1).

EXAMPLE 7

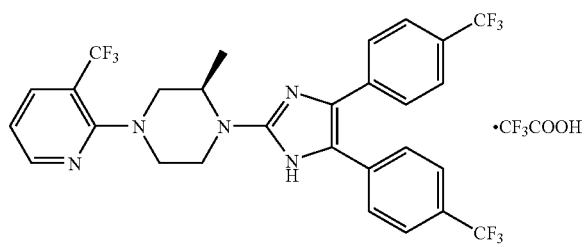

(2R)-1-(4,5-Bis(4-(trifluoromethyl)phenyl)-1H-imidazol-2-yl)-2-methyl-4-(3-(trifluoromethyl)pyridin-2-yl)piperazine, trifluoroacetic acid salt

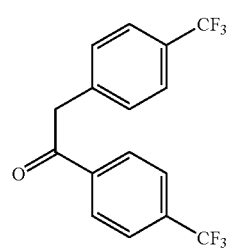

(a) 1,2-bis(4-(trifluoromethyl)phenyl)ethanone

To a cooled to –50° C. solution of CuCN (85 mg, 0.95 mmol, Aldrich) and LiBr (80 mg, 0.92 mmol, Aldrich) in THF (10 mL) was added (4-(trifluoromethyl)benzyl)zinc(II) chloride (1.25 g, 4.81 mmol, Rieke Metals) and 4-(trifluoromethyl)benzoyl chloride (0.996 g, 4.78 mmol, Aldrich) with stirring. The reaction mixture was left to reach RT and the stirring was continued for 21 h. The reaction mixture was diluted with EtOAc (125 mL) and 5N HCl (30 mL). The EtOAc layer was separated, washed with water (35 mL) and brine (35 mL), dried over anhydrous sodium sulfate, and filtered. The filtrate was evaporated in vacuo and the residue was purified by silica gel column chromatography, eluting with EtOAc/hexane (1:10), to give the title compound as a yellow amorphous solid. MS (ESI, pos. ion) m/z: 333.

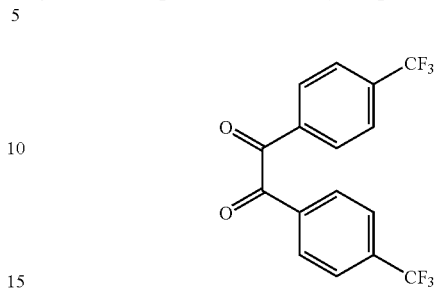

(b) 1,2-Bis(4-(trifluoromethyl)phenyl)ethane-1,2-dione

A solution of 1,2-bis(4-(trifluoromethyl)phenyl)ethanone from step (a) above (0.40 g, 1.20 mmol) and N-bromosuccimide (0.450 g, 2.53 mmol, Aldrich) in DMSO (8 mL) was heated to 65° C. for 4.5 h. The reaction mixture was cooled to RT diluted with EtOAc (75 mL) and water (25 mL). The EtOAc layer was separated, washed with brine (20 mL), dried over anhydrous sodium sulfate, and filtered. The filtrate was evaporated in vacuo and the residue was purified by silica gel column chromatography, eluting with EtOAc/hexane (1:10), to give the title compound as a yellow amorphous solid. MS (ESI, pos. ion) m/z: 347.

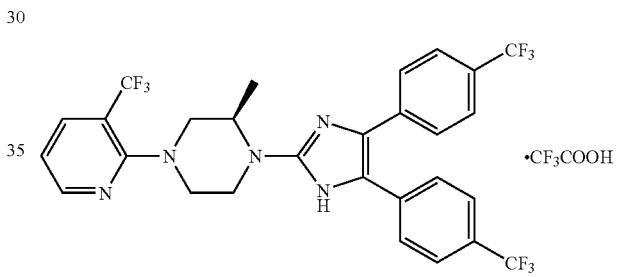

(c) (2R)-1-(4,5-Bis(4-(trifluoromethyl)phenyl)-1H-imidazol-2-yl)-2-methyl-4-(3-(trifluoromethyl)pyridin-2-yl)piperazine, trifluoroacetic acid salt 1,2-Bis(4-(trifluoromethyl)phenyl)ethane-1,2-dione from step (b) above (300 mg, 0.87 mmol) reacted with (2R)-2-methyl-4-(3-(trifluoromethyl)pyridin-2-yl)piperazine-1-carboxamidine (71 mg, 0.25 mmol, Example 6(a)) under the conditions of Example 4(b). The crude product was purified by preparative HPLC [gradient 10-90% MeCN (0.1% TFA)/H$_2$O (0.1% TFA)] to give the title compound as an amorphous solid. MS (ESI, pos. ion) m/z: 600 (M+1).

EXAMPLE 8

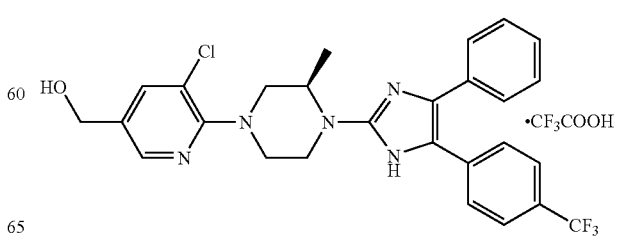

(3R)-(5-Chloro-6-(3-methyl-4-(4-phenyl-5-(4-(trifluoromethyl)phenyl)-1H-imidazol-2-yl)piperazin-1-yl)pyridin-3-yl)methanol, trifluoroacetic acid salt

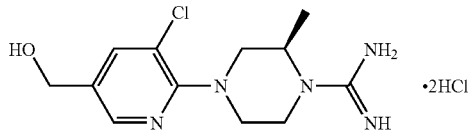

(a) (2R)-4-(3-Chloro-5-(hydroxymethyl)pyridin-2-yl)-2-methylpiperazine-1-carboxamidine dihydrochloride To a stirred solution of (3R)-(5-chloro-6-(3-methylpiperazin-1-yl)pyridin-3-yl)-methanol (1.44 g, 5.96 mmol, WO2004/035549) and 1,3-bis(tert-butoxycarbonyl)-2-methyl-2-thiopseudourea (1.84 g, 6.34 mmol, Aldrich) in DCM (50 mL) was added triethylamine (0.76 g, 7.5 mmol, Aldrich) and mercuric chloride (1.78 g, 6.56 mmol, Aldrich). The reaction mixture was stirred at RT for 15 h and filtered. The filter cake was washed with DCM (2×100 mL). The combined filtrates were washed with water (75 mL) and brine (50 mL), dried over anhydrous sodium sulfate, and filtered. The filtrate was evaporated in vacuo to give a foamy solid [MS (ESI, pos. ion) m/z: 484 (M+1)], which was dissolved in a mixture of dioxane (50 mL) and 4M solution of HCl in dioxane (50 mL, Aldrich), and stirred at RT for 16 h. The reaction mixture was evaporated in vacuo and the residue was purified by silica gel column chromatography, eluting with DCM/MeOH (5:1) to give the title compound as a pale-yellow amorphous solid. MS (ESI, pos. ion) m/z: 284.

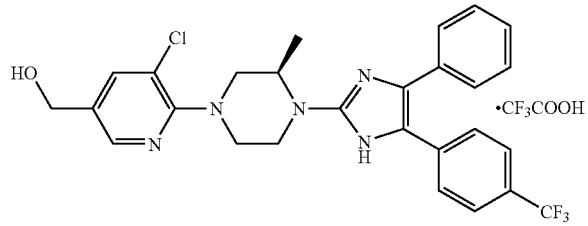

(b) (3R)-(5-Chloro-6-(3-methyl-4-(4-phenyl-5-(4-(trifluoromethyl)phenyl)-1H-imidazol-2-yl)piperazin-1-yl)pyridin-3-yl)methanol, trifluoroacetic acid salt To a solution of (2R)-4-(3-chloro-5-(hydroxymethyl)pyridin-2-yl)-2-methylpiperazine-1-carboxamidine dihydrochloride from step (a) above (148 mg, 0.42 mmol) and 1-phenyl-2-(4-(trifluoromethyl)phenyl)ethane-1,2-dione (106 mg, 0.38 mmol, Example 4(a)) in methanol (10 mL) was added N,N-diisopropylethylamine (0.33 g, 2.58 mmol, Aldrich), and the mixture was stirred at RT for 1.5 h. The reaction mixture was diluted with methanol (5 mL) and stirred with 10% palladium on carbon (80 mg, Aldrich) and LiCl (330 mg, 7.78 mmol) under H$_2$ atmosphere at RT for 22 h. The palladium catalyst was removed by filtration over a Celite® pad and the filtrate was concentrated in vacuo. The residue was dissolved in MeOH (3 mL) and purified by preparative HPLC [gradient 10-90% MeCN (0.1% TFA)/H$_2$O (0.1% TFA)] to give the title compound as an off-white amorphous solid. MS (ESI, pos. ion) m/z: 528 (M+1).

EXAMPLE 9

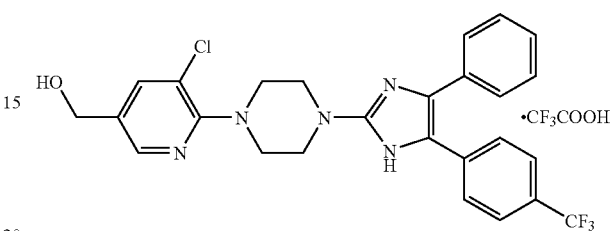

(5-Chloro-6-(4-(4-phenyl-5-(4-(trifluoromethyl)phenyl)-1H-imidazol-2-yl)piperazin-1-yl)pyridin-3-yl)methanol, trifluoroacetic acid salt

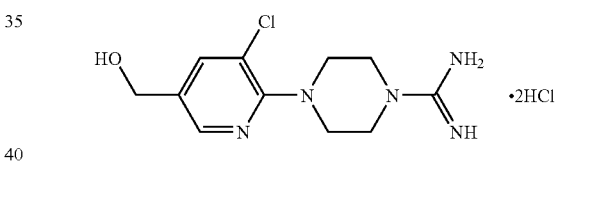

(a) (4-(3-Chloro-5-(hydroxymethyl)pyridin-2-yl)piperazine-1-carboxamidine dihydrochloride (5-Chloro-6-(piperazin-1-yl)pyridin-3-yl)methanol (2.04 g, 8.99 mmol, WO2004/035549) reacted with 1,3-bis(tert-butoxycarbonyl)-2-methyl-2-thiopseudourea (2.66 g, 9.16 mmol, Aldrich) under the conditions of Example 8(a) to give the title compound as a foamy white solid. MS (ESI, pos. ion) m/z: 270 (M+1).

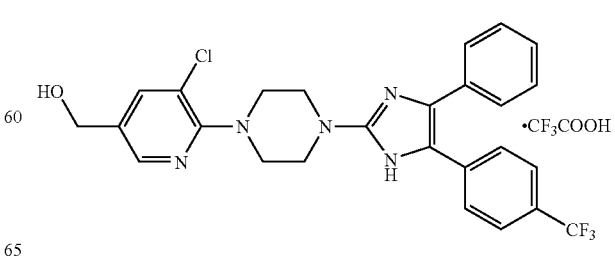

(b) (5-Chloro-6-(4-(4-phenyl-5-(4-(trifluoromethyl)phenyl)-1H-imidazol-2-yl)piperazin-1-yl)pyridin-3-yl)methanol, trifluoroacetic acid salt (4-(3-Chloro-5-(hydroxymethyl)pyridin-2-yl)piperazine-1-carboxamidine dihydrochloride from step (a) above (164 mg, 0.48 mmol) reacted with 1-phenyl-2-(4-(trifluoromethyl)phenyl)ethane-1,2-dione (133 mg, 0.48 mmol, Example 4(a)) under the conditions of Example 8(b). The crude product was purified by preparative HPLC [gradient 10-90% MeCN (0.1% TFA)/H$_2$O (0.1% TFA)] to give the title compound as an off-white amorphous solid. MS (ESI, pos. ion) m/z: 514 (M+1).

EXAMPLE 10

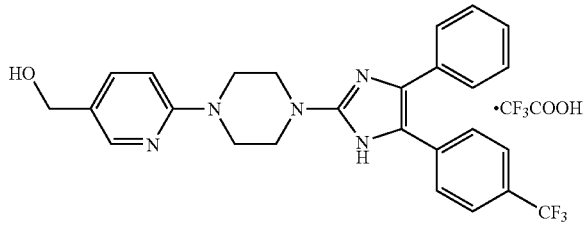

(6-(4-(4-Phenyl-5-(4-(trifluoromethyl)phenyl)-1H-imidazol-2-yl)piperazin-1-yl)pyridin-3-yl)methanol, trifluoroacetic acid salt The title compound was formed as a side product under the conditions for the reduction of the intermediate of Example 9(b). The crude product was purified by preparative HPLC [gradient 10-90% MeCN (0.1% TFA)/H$_2$O (0.1% TFA)] to give the title compound as a foamy white solid. MS (ESI, pos. ion) m/z: 480 (M+1).

EXAMPLE 11

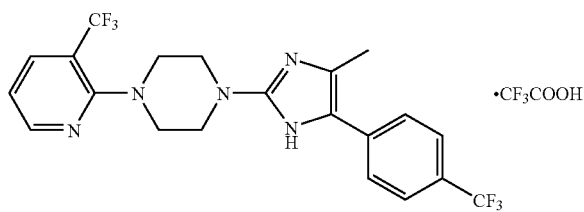

1-(4-Methyl-5-(4-(trifluoromethyl)phenyl)-1H-imidazol-2-yl)-4-(3-(trifluoromethyl)pyridin-2-yl)piperazine, trifluoroacetic acid salt 4-(3-(Trifluoromethyl)pyridin-2-yl)piperazine-1-carboxamidine (89 mg, 0.33 mmol, Example 3(a)) reacted with 1-(4-(trifluoromethyl)phenyl)propane-1,2-dione (80 mg, 0.37 mmol, Matrix) under the conditions of Example 4(b). The crude product was purified by preparative HPLC [gradient 10-90% MeCN (0.1% TFA)/H$_2$O (0.1% TFA)] to give the title compound as an amorphous solid. MS (ESI, pos. ion) m/z: 456 (M+1).

EXAMPLE 12

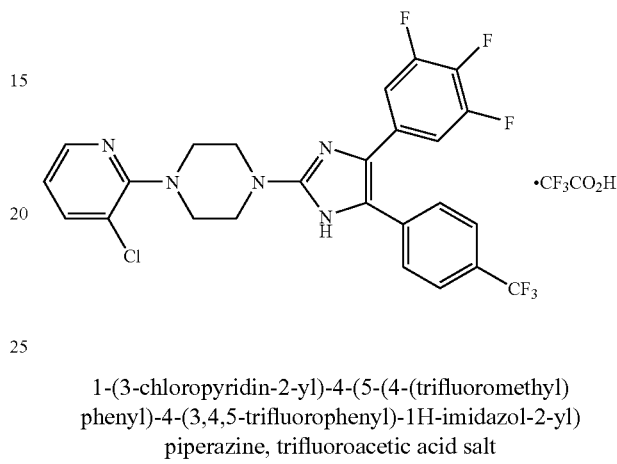

1-(3-chloropyridin-2-yl)-4-(5-(4-(trifluoromethyl)phenyl)-4-(3,4,5-trifluorophenyl)-1H-imidazol-2-yl)piperazine, trifluoroacetic acid salt

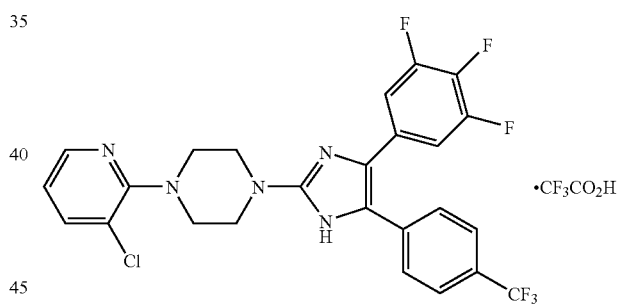

(a) 1-(3-Chloropyridin-2-yl)-4-(5-(4-(trifluoromethyl)phenyl)-4-(3,4,5-trifluorophenyl)-1H-imidazol-2-yl)piperazine trifluoroacetic acid A mixture of 1-[5-(4-trifluoromethyl-phenyl)-4-(3,4,5-trifluorophenyl)-1-(2-trimethylsilanyl-ethoxymethyl)-1H-imidazol-2-yl]-piperazine (80. mg, 0.14 mmol, Example 35(d)), 2,3-dichloropyridine (42 mg, 0.29 mmol, Lancaster), and sodium bicarbonate (24 mg, 0.29 mmol, Mallinckrodt) in NMP (1 mL) was subjected to microwave irradiation at 180° C. for 1 h. The reaction mixture was filtered and the solid was washed with MeOH:DCM (1:1, 2 mL). The filtrate was then concentrated in vacuo and the residue was dissolved in MeOH (1 mL) and purified by preparative HPLC [gradient 10-85% MeCN (0.1% TFA)/H$_2$O (0.1% TFA)] to give the desired product which was dissolved in TFA (1 mL) and was reacted under the condition of Example 16(g) to give the title compound as a light yellow solid. MS (ESI, positive ion) m/z: 538 (M+1).

EXAMPLE 13

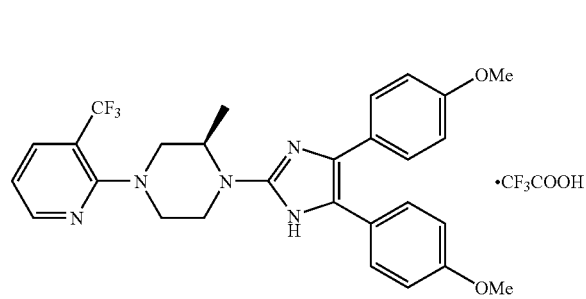

(2R)-1-(4,5-Bis(4-methoxyphenyl)-1H-imidazol-2-yl)-2-methyl-4-(3-(trifluoromethyl)pyridin-2-yl)piperazine, trifluoroacetic acid salt (2R)-2-Methyl-4-(3-(trifluoromethyl)pyridin-2-yl)piperazine-1-carboxamidine (83 mg, 0.30 mmol, Example 6(a)) reacted with 1,2-bis(4-methoxyphenyl)ethane-1,2-dione (88 mg, 0.33 mmol, Aldrich) under the conditions of Example 4(b). The crude product was purified by preparative HPLC [gradient 10-90% MeCN (0.1% TFA)/H$_2$O (0.1% TFA)] to give the title compound as an amorphous solid. MS (ESI, pos. ion) m/z: 524 (M+1).

EXAMPLE 14

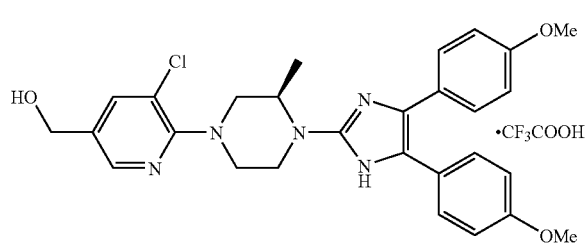

(3R)-(6-(4-(4,5-Bis(4-methoxyphenyl)-1H-imidazol-2-yl)-3-methylpiperazin-1-yl)-5-chloropyridin-3-yl)methanol, trifluoroacetic acid salt (2R)-4-(3-Chloro-5-(hydroxymethyl)pyridin-2-yl)-2-methylpiperazine-1-carboxamidine dihydrochloride (150 mg, 0.42 mmol, Example 8(a)) reacted with 1,2-bis(4-methoxyphenyl)ethane-1,2-dione (115 mg, 0.43 mmol, Aldrich) under the conditions of Example 8(b). The crude product was purified by preparative HPLC [gradient 10-90% MeCN (0.1% TFA)/H$_2$O (0.1% TFA)] to give the title compound as an amorphous solid. MS (ESI, pos. ion) m/z: 520 (M+1).

EXAMPLE 15

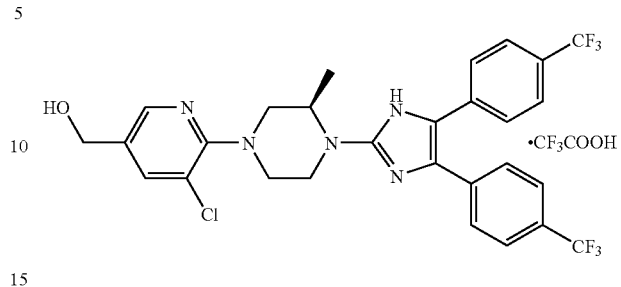

(R)-(6-(4-(4,5-Bis(4-(trifluoromethyl)phenyl)-1H-imidazol-2-yl)-3-methylpiperazin-1-yl)-5-chloropyridin-3-yl)methanol, trifluoroacetic acid salt 1,2-Bis(4-(trifluoromethyl)phenyl)ethane-1,2-dione (155 mg, 0.45 mmol, Example 7(b)) was reacted with (2R)-4-(3-Chloro-5-(hydroxylmethyl)pyridin-2-yl)-2-methylpiperazine-1-carboxamidine dihydrochloride (153 mg, 0.43 mmol, Example 8(a)) under the conditions of Example 8(b). The crude product was purified by preparative HPLC [gradient 10-90% MeCN (0.1% TFA)/H$_2$O (0.1% TFA)] to give the title compound as a pale yellow amorphous solid. MS (ESI, pos. ion) m/z: 596

EXAMPLE 16

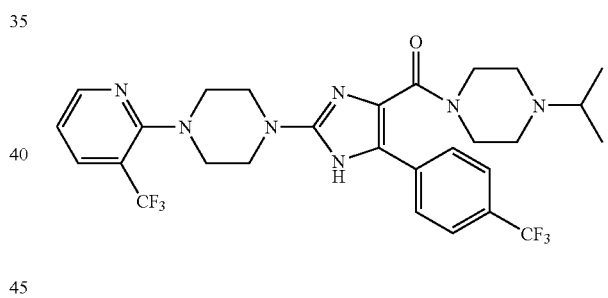

(4-Isopropylpiperazin-1-yl)(5-(4-(trifluoromethyl)phenyl)-2-(4-(3-(trifluoromethyl)pyridin-2-yl)piperazin-1-yl)-1H-imidazol-4-yl)methanone (a) Methyl 2,5-dibromo-1H-imidazole-4-carboxylate A mixture of methyl 1H-imidazole-4-carboxylate (10. g, 79 mmol, Aldrich) and bromine (13 mL, 238 mmol) in acetic acid (264 mL) was stirred at RT for 60 h. Then, saturated NaHCO$_3$ was added to the reaction mixture at 0° C. until pH ~8 was achieved. The solvents were removed and the residue was purified on silica gel using ISCO Combiflash® system with DCM/2M methanolic ammonia gradient to give the title compound as a white amorphous solid. MS (ESI, pos. ion) m/z: 283 (M+1)

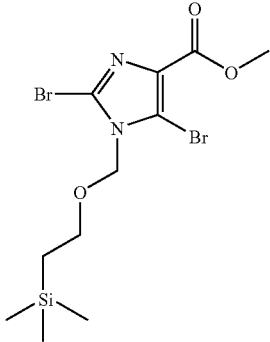

(b) Methyl 2,5-dibromo-1-((2-(trimethylsilyl)ethoxy)methyl)-1H-imidazole-4-carboxylate A mixture of (2-chloromethoxy-ethyl)trimethylsilane (3.9 mL, 22.05 mmol, Aldrich) and sodium hydride (706 mg, 29.4 mmol, Aldrich) in THF (25 mL) was stirred at RT for 0.1 h and a solution of 2,5-dibromo-1H-imidazole-4-carboxylic acid methyl ester from step (a) above (4.15 g, 14.7 mmol) in THF (25 mL) was added slowly at 0° C. The reaction mixture was stirred at RT for 12 h. Then, $H_2O$ (200 mL) was added slowly and the mixture was extracted with EtOAc (2×300 mL). The combined organic extracts were dried over $MgSO_4$ and concentrated in vacuo. The residue was purified on silica gel using ISCO Combiflash® system with EtOAc/Hexanes (1:4) as the eluant to give the title compound as a colorless oil. H-NMR was used for characterization.

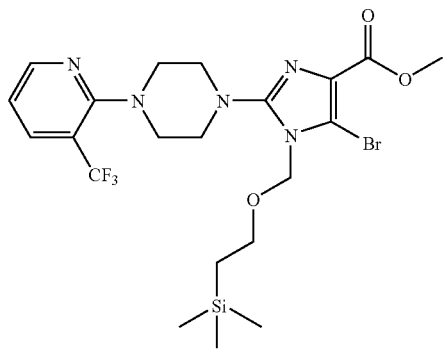

(c) Methyl 5-bromo-2-(4-(3-(trifluoromethyl)pyridin-2-yl)piperazin-1-yl)-1-((2-(trimethylsilyl)ethoxy)methyl)-1H-imidazole-4-carboxylate A mixture of 2,5-dibromo-1-(2-trimethylsilanyl-ethoxymethyl)-1H-imidazole-4-carboxylic acid methyl ester from step (b) above (2.7 g, 6.6 mmol) and 1-(3-trifluoromethyl-pyridin-2-yl)-piperazine (7.6 g, 33 mmol, Oakwood) was subjected to microwave irradiation at 130° C. for 900 s. The reaction mixture was cooled to RT and the resulting residue was purified on silica gel using ISCO Combiflash® system with EtOAc/Hexanes (1:4) as the eluant to give the title compound as colorless oil. MS (ESI, positive ion) m/z: 564 (M+1).

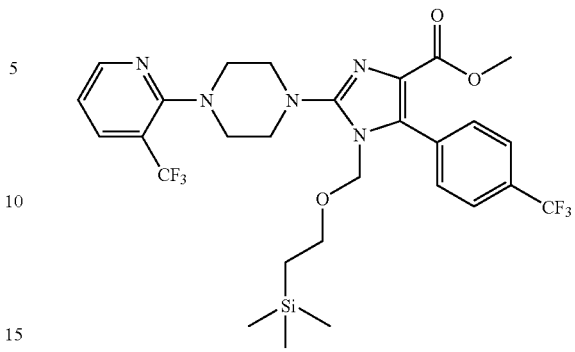

(d) Methyl 5-(4-(trifluoromethyl)phenyl)-2-(4-(3-(trifluoromethyl)pyridin-2-yl)piperazin-1-yl)-1-((2-(trimethylsilyl)ethoxy)methyl)-1H-imidazole-4-carboxylate A mixture of methyl 5-bromo-2-(4-(3-(trifluoromethyl)pyridin-2-yl)piperazin-1-yl)-1-((2-(trimethylsilyl)ethoxy)methyl)-1H-imidazole-4-carboxylate from step (c) above (2 g, 3.55 mmol), 4-(trifluoromethyl)phenylboronic acid (675 mg, 3.55 -mmol, Aldrich), tetrakis(triphenylphosphine)palladium(0) (82 mg, 0.071 mmol, Strem Chemicals), and 2M $Na_2CO_3$ (4.8 mL) in 1,4-dioxane (24 mL) was subjected to microwave irradiation at 130° C. for 0.25 h. The solvents were removed and the residue was purified on silica gel using ISCO Combiflash® system with EtOAc/Hexanes (1:4) as the eluant to give the title compound as colorless oil. MS (ESI, positive ion) m/z: 630 (M+1).

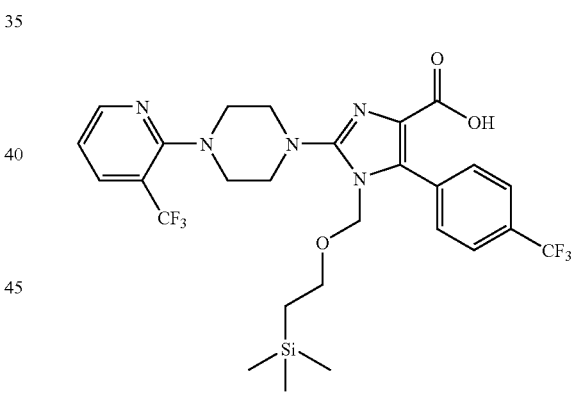

(e) 5-(4-(Trifluoromethyl)phenyl)-2-(4-(3-(trifluoromethyl)pyridin-2-yl)piperazin-1-yl)-1-((2-(trimethylsilyl)ethoxy)methyl)-1H-imidazole-4-carboxylic acid A solution of methyl 5-(4-(trifluoromethyl)phenyl)-2-(4-(3-(trifluoromethyl)pyridin-2-yl)piperazin-1-yl)-1-((2-(trimethylsilyl)ethoxy)methyl)-1H-imidazole-4-carboxylate from step (d) above (500. mg, 0.794 mmol) in $THF:H_2O$ (5:1) was added LiOH (29 mg, 1.19 mmol, Aldrich) at 0° C. The mixture was stirred at RT for 16 h and the solvents were removed. The residue was dissolved in $H_2O$ (20 mL) and the aqueous solution was adjusted to pH ~7. Then, the solvents were removed and the residue was purified on silica gel using ISCO Combiflash® system with EtOAc/Hexanes (1:4) as the eluant to give the title compound as a white solid. MS (ESI, positive ion) m/z: 616 (M+1).

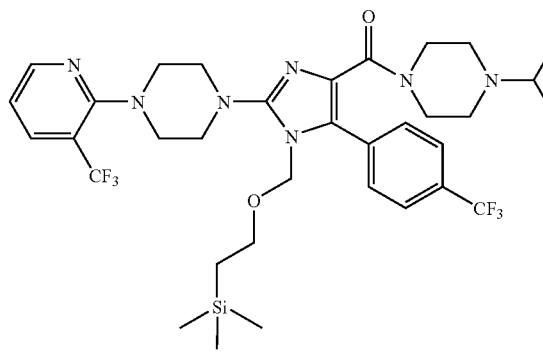

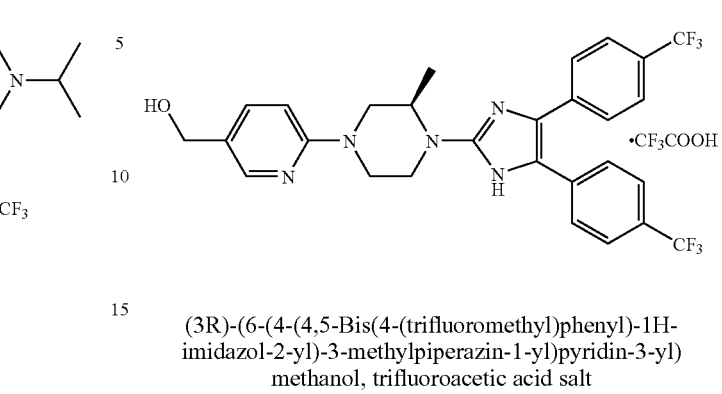

EXAMPLE 17

(3R)-(6-(4-(4,5-Bis(4-(trifluoromethyl)phenyl)-1H-imidazol-2-yl)-3-methylpiperazin-1-yl)pyridin-3-yl)methanol, trifluoroacetic acid salt (f) (4-Isopropylpiperazin-1-yl)(5-(4-(trifluoromethyl)phenyl)-2-(4-(3-(trifluoromethyl)pyridin-2-yl)piperazin-1-yl)-1-((2-(trimethylsilyl)ethoxy)methyl)-1H-imidazol-4-yl)methanone A mixture of 5-(4-(trifluoromethyl)phenyl)-2-(4-(3-(trifluoromethyl)pyridin-2-yl)piperazin-1-yl)-1-((2-(trimethylsilyl)ethoxy)methyl)-1H-imidazole-4-carboxylic acid from step (e) above (200. mg, 0.325 mmol), benzotriazol-1-yloxytris(dimethylamino)phosphonium hexafluorophosphate (216 mg, 0.488 mmol, Aldrich), DIEA (0.17 mL, 0.98 mmol, Aldrich), and 1-isopropylpiperazine (62 mg, 0.49 mmol, Aldrich) in DCM (2 mL) was stirred at RT for 70 h. The solvents were removed and the residue was purified on silica gel using ISCO Combiflash® system with DCM/2M methanolic ammonia gradient to give the title compound, which was used in the next step. MS (ESI, positive ion) m/z: 726 (M+1).

A solution of (2R)-4-(3-chloro-5-(hydroxymethyl)pyridin-2-yl)-2-methylpiperazine-1-carboxamidine dihydrochloride (24 mg, 0.07 mmol, Example 8(a)), 1,2-bis(4-(trifluoromethyl)phenyl)ethane-1,2-dione (19 mg, 0.06 mmol, Example 7(a)) and N,N-diisopropylethylamine (0.04 g, 0.32 mmol, Aldrich) in methanol (7 mL) was stirred at RT for 18.5 h. The reaction mixture was diluted with methanol (2 mL), and stirred with 10% palladium on carbon (45 mg, Aldrich) and LiCl (150 mg, 3.54 mmol) under H₂ atmosphere at RT for 7 h. The palladium catalyst was removed by filtration over a Celite® pad and the filtrate was concentrated in vacuo. The residue was dissolved in MeOH (2 mL) and purified by preparative HPLC [gradient 10-90% MeCN (0.1% TFA)/H₂O (0.1% TFA)] to give the title compound as an off-white amorphous solid. MS (ESI, pos. ion) m/z: 562 (M+1).

EXAMPLE 18

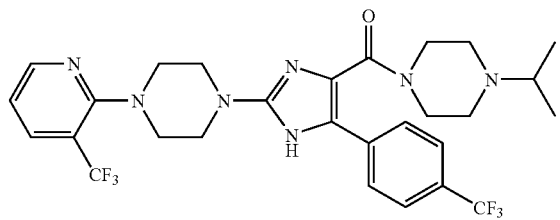

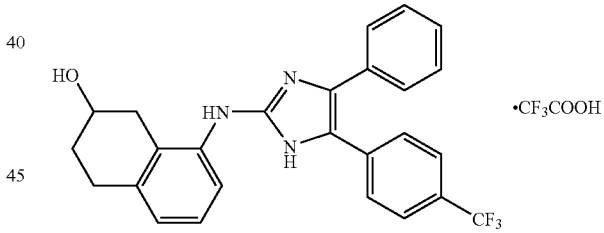

8-(4-Phenyl-5-(4-(trifluoromethyl)phenyl)-1H-imidazol-2-ylamino)-1,2,3,4-tetrahydronaphthalen-2-ol, trifluoroacetic acid salt (g) (4-Isopropylpiperazin-1-yl)(5-(4-(trifluoromethyl)phenyl)-2-(4-(3-(trifluoromethyl)pyridin-2-yl)piperazin-1-yl)-1H-imidazol-4-yl)methanone A solution of (4-isopropylpiperazin-1-yl)(5-(4-(trifluoromethyl)phenyl)-2-(4-(3-(trifluoromethyl)pyridin-2-yl)piperazin-1-yl)-1-((2-(trimethylsilyl)ethoxy)methyl)-1H-imidazol-4-yl)methanone from step (f) above was dissolved in TFA (1 mL). The solution was stirred at RT for 1 h. The solvent was removed and the residue was purified on silica gel using ISCO Combiflash® system with DCM/2M methanolic ammonia gradient to give the title compound as a white solid. MS (ESI, positive ion) m/z: 596 (M+1).

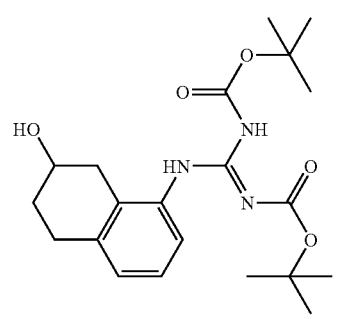

(a) 2,3-Bis(tert-butoxycarbonyl)-1-(7-hydroxy-5,6,7,8-tetrahydronaphthalen-1-yl)guanidine To a solution of 8-amino-1,2,3,4-tetrahydronaphthalen-2-ol (0.238 g, 1.46 mmol) reacted with 1,3-bis(tert-butoxycarbonyl)-2-methyl-2-thiopseudourea (0.45 g, 1.55 mmol, Aldrich) in DCM (10 mL) was added triethylamine (0.38 g, 3.7 mmol, Aldrich) and mercuric chloride (415 mg, 1.53 mmol, Aldrich). The reaction mixture was stirred at RT for 15 h and filtered. The filter cake was washed with DCM (2×5 mL). The combined filtrates were concentrated and the residue was purified by silica gel column chromatography, eluting with EtOAc/hexane (1:5) to give the title compound as a pale-yellow amorphous solid. MS (ESI, pos. ion) m/z: 406 (M+1).

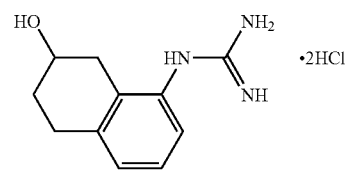

(b) 1-(7-hydroxy-5,6,7,8-tetrahydronaphthalen-1-yl)guanidine dihydrochloride salt A solution of product from step (a) was taken up in dioxane (8 mL) and was treated with HCl (4M in dioxane, 10 mL, Aldrich) and stirred at RT for 48 h. The reaction mixture was concentrated and the residue was purified by silica gel column chromatography, eluting with DCM/MeOH (7:1) to give the title compound as brown oil. MS (ESI, pos. ion) m/z: 206 (M+1).

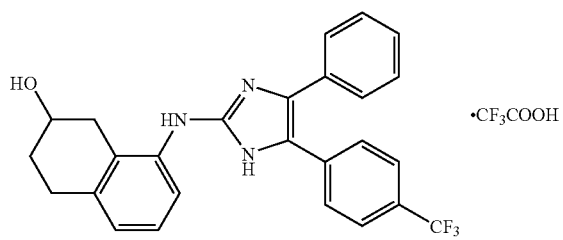

(c) 8-(4-Phenyl-5-(4-(trifluoromethyl)phenyl)-1H-imidazol-2-ylamino)-1,2,3,4-tetrahydronaphthalen-2-ol, trifluoroacetic acid salt 1-(7-Hydroxy-5,6,7,8-tetrahydronaphthalen-1-yl)guanidine, dihydrochloride salt from step (b) above (146 mg, 0.53 mmol) reacted with 1-phenyl-2-(4-(trifluoromethyl)phenyl)ethane-1,2-dione (146 mg, 0.53 mmol, Example 4(a)) under the conditions of Example 4(b). The crude product was purified by preparative HPLC [gradient 10-90% MeCN (0.1% TFA)/H$_2$O (0.1% TFA) to give the title compound as pale-yellow amorphous solid. MS (ESI, pos. ion) m/z: 450 (M+1).

EXAMPLE 19

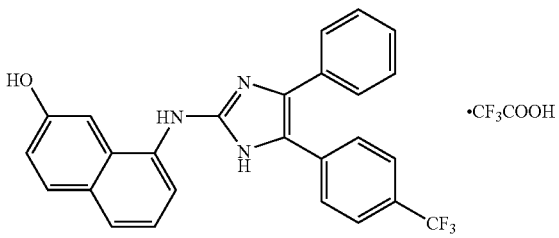

8-(4-Phenyl-5-(4-(trifluoromethyl)phenyl)-1H-imidazol-2-ylamino)naphthalen-2-ol, trifluoroacetic acid salt

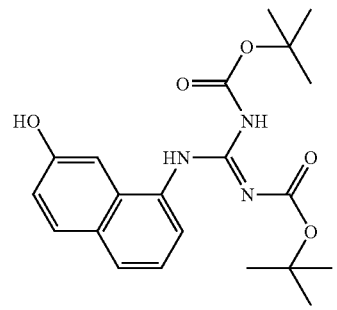

(a) 2,3-Bis(tert-butoxycarbonyl)-1-(7-hydroxynaphthalen-1-yl)guanidine

8-Aminonaphthalen-2-ol (2.5 g, 15.7 mmol, Aldrich) reacted with 1,3-bis(tert-butoxycarbonyl)-2-methyl-2-thiopseudourea (4.94 g, 17.0 mmol, Aldrich) in DCM (35 mL) was added triethylamine (5.08 g, 50.2 mmol, Aldrich) and mercuric chloride (4.22 g, 15.5 mmol, Aldrich). The reaction mixture was stirred at RT for 15 h and filtered. The filter cake was washed with DCM (2×30 mL). The combined filtrates were concentrated to give the title compound as a dark brown oil. MS (ESI, pos. ion) m/z: 402 (M+1)

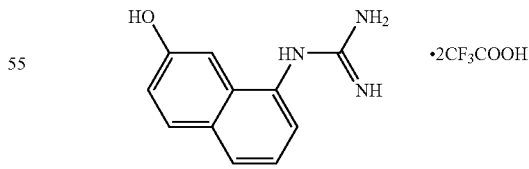

(b) 1-(7-Hydroxynaphthalen-1-yl)guanidine ditrifluoroacetic acid salt

A solution of product from step (a) above (2.0 g, 5.0 mmol) was treated with TFA/DCM (1:1) mixture (50 mL) and stirred at RT for 16 h. The reaction mixture was concentrated and dried under vacuo to give the title compound as an off-white solid. MS (ESI, pos. ion) m/z: 202 (M+1).

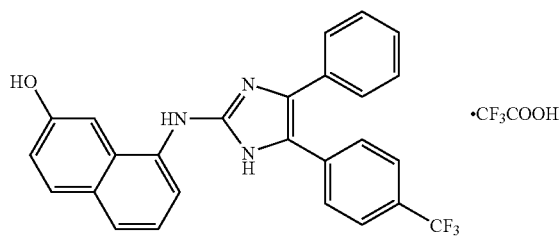

(b) 8-(4-Phenyl-5-(4-(trifluoromethyl)phenyl)-1H-imidazol-2-ylamino)naphthalen-2-ol, trifluoroacetic acid salt 1-(7-Hydroxynaphthalen-1-yl)guanidine, ditrifluoroacetic acid salt from step (b) above (199 mg, 0.46 mmol) reacted with 1-phenyl-2-(4-(trifluoromethyl)phenyl)ethane-1,2-dione (109 mg, 0.39 mmol, Example 4(a)) under the conditions of Example 4(b). The crude product was purified by preparative HPLC [gradient 10-90% MeCN (0.1% TFA)/H$_2$O (0.1% TFA) to give the title compound as pale-yellow amorphous solid. MS (ESI, pos. ion) m/z: 446 (M+1).

EXAMPLE 20

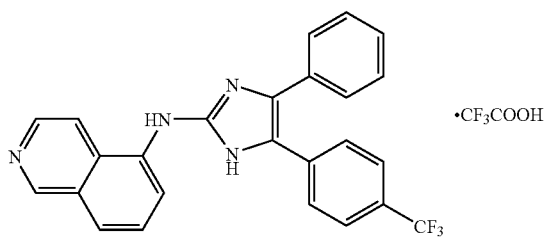

N-(4-Phenyl-5-(4-(trifluoromethyl)phenyl)-1H-imidazol-2-yl)isoquinolin-5-amine, trifluoroacetic acid salt

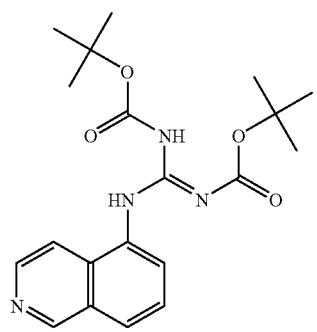

(a) 2,3-Bis(tert-butoxycarbonyl)-1-(Isoquinolin-5-yl)guanidine

To a solution of Isoquinolin-5-amine (1.11 g, 7.69 mmol, Aldrich) and 1,3-bis(tert-butoxycarbonyl)-2-methyl-2-thiopseudourea (2.28 g, 7.85 mmol, Aldrich) in DCM (25 mL) was added triethylamine (1.60 g, 15.78 mmol, Aldrich) and mercuric chloride (2.1 g, 7.74 mmol, Aldrich). The reaction mixture was stirred at room temperature for 15 h and filtered. The filter cake was washed with DCM (2×25 mL). The combined filtrates were concentrated and the residue was purified by silica gel column chromatography, eluting with EtOAc/hexane (1:5) to give 2.29 mg (77%) of the title compound as a pale-yellow amorphous solid. MS (ESI, pos. ion) m/z: 387 (M+1).

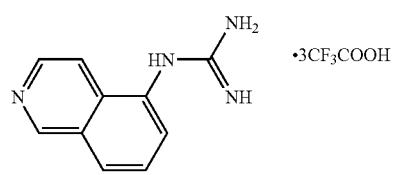

(b) 1-(Isoquinolin-5-yl)guanidine, tritrifluoroacetic acid salt 2,3-Bis(tert-butoxycarbonyl)-1-(Isoquinolin-5-yl)guanidine from step (b) above (2.29 mg, 5.93 mmol) was treated with TFA/DCM (1:1) mixture (60 mL) and stirred at room temperature for 16 h. The reaction mixture was concentrated and dried under vacuo to give 3.1 mg (99%) of the title compound. MS (ESI, pos. ion) m/z: 187 (M+1).

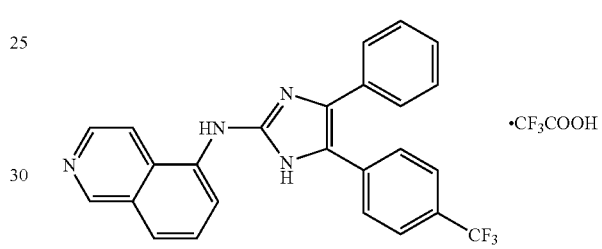

(c) N-(4-Phenyl-5-(4-(trifluoromethyl)phenyl)-1H-imidazol-2-yl)isoquinolin-5-amine, trifluoroacetic acid salt 1-(Isoquinolin-5-yl)guanidine, tritrifluoroacetic acid salt from step (a) above (245 mg, 0.59 mmol) reacted with 1-phenyl-2-(4-(trifluoromethyl)phenyl)ethane-1,2-dione (120 mg, 0.43 mmol, Example 4(a)) under the conditions of Example 4(b). The crude product was purified by preparative HPLC [gradient 10-90% MeCN (0.1% TFA)/H$_2$O (0.1% TFA) to give the title compound as pale-yellow amorphous solid. MS (ESI, pos. ion) m/z: 431 (M+1).

EXAMPLE 21

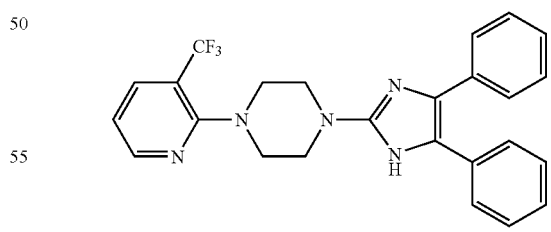

1-(4,5-Diphenyl-1H-imidazol-2-yl)-4-(3-(trifluoromethyl)pyridin-2-yl)piperazine 4-(3-(Trifluoromethyl)pyridin-2-yl)piperazine-1-carboxamidine (300 mg, 1.10 mmol, Example 3(a)) reacted with benzil (231 mg, 1.10 mmol, Aldrich) under the conditions of Example 4(b). The crude product was purified by silica gel

EXAMPLE 22

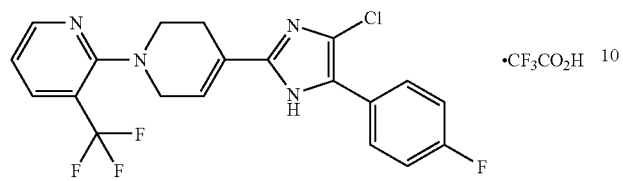

2-(4-(4-Chloro-5-(4-fluorophenyl)-1H-imidazol-2-yl)-5,6-dihydropyridin-1(2H)-yl)-3-(trifluoromethyl) pyridine trifluoro acetic acid salt

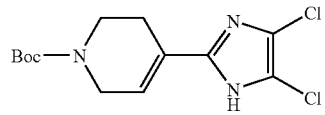

(a) 4-(4,5-Dichloro-1H-imidazol-2-yl)-3,6-dihydro-2H-pyridine-1-carboxylic acid tert-butyl ester A mixture if 2-bromo-4,5-dichloro-1H-imidazole (5 g, 23 mmol, Aldrich), 4-(4,4,5,5-tetramethyl-[1,3,2]dioxaborolan-2-yl)-3,6-dihydro-2H-pyridine-1-carboxylic acid tert-butyl ester (8 g, 26 mmol, Chemshop), dichloro-bis(triphenylphosphine) palladium (II) (3.28 g, 4.68 mmol, Aldrich), sodium carbonate (9.8 g, 93.6 mmol, Aldrich), and DME/H$_2$O/EtOH (7:3:2) solution (156 mL) was heated to 90° C. for 12 h under nitrogen. The reaction mixture was cooled to RT and evaporated in vacuo. The residue was purified by silica gel column chromatography (gradient 0-100% EtOAc/hexane) to give the title compound as a yellow solid. MS (ESI, positive ion) m/z: 318 (M+1).

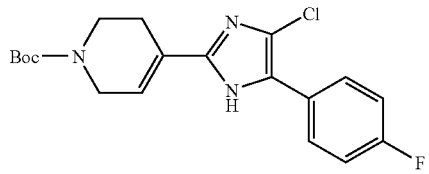

(b) 4-[4-Chloro-5-(4-fluoro-phenyl)-1H-imidazol-2-yl]-3,6-dihydro-2H-pyridine-1-carboxylic acid tert-butyl ester A mixture of 4-(4,5-dichloro-1H-imidazol-2-yl)-3,6-dihydro-2H-pyridine-1-carboxylic acid tert-butyl ester from step (a) above (300 mg, 0.94 mmol), 4-fluorophenyl boronic acid (265 mg, 1.89 mmol, Aldrich), dichloro-bis(triphenylphosphine) palladium (II) (266 mg, 0.38 mmol, Aldrich), sodium carbonate (397 mg, 3.78 mmol, Aldrich), and DME/H$_2$O/EtOH (7:3:2) solution (6 mL) was heated to 90° C. for 12 h under nitrogen. The reaction mixture was cooled to RT and the solvents were evaporated. The residue was purified by silica gel column chromatography (gradient 10-50% EtOAc/hexane) to give the title compound as a yellow solid, which was directly used in the next step. MS (ESI, positive ion) m/z: 378 (M+1).

column chromatography (1:3 EtOAc/hexane) to give the title compound as a white amorphous solid. MS (ESI, pos. ion) m/z: 450.

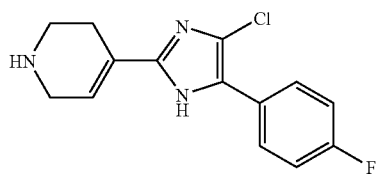

(c) 4-[4-Chloro-5-(4-fluoro-phenyl)-1H-imidazol-2-yl]-1,2,3,6-tetrahydropyridine A solution of 4-[4-chloro-5-(4-fluoro-phenyl)-1H-imidazol-2-yl]-3,6-dihydro-2H-pyridine-1-carboxylic acid tert-butyl ester from step (b) above in 30% TFA in DCM (5 mL) was stirred at RT for 1 h. The solvents were removed, and the residue was stirred with sat. aqueous solution of NaHCO$_3$ (10 mL) at RT for 0.5 h. The reaction mixture was extracted with EtOAc (2×10 mL). The combined organic extracts were dried over MgSO$_4$ and filtered. The filtrate was evaporated in vacuo to give the title compound, which was directly used in the next step without additional purification. MS (ESI, positive ion) m/z: 278 (M+1).

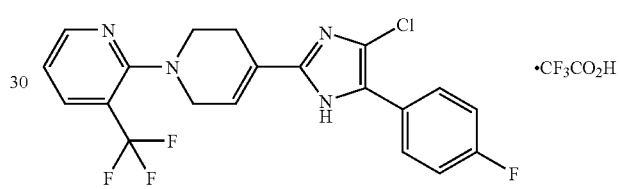

(d) 2-(4-(4-Chloro-5-(4-fluorophenyl)-1H-imidazol-2-yl)-5,6-dihydropyridin-1(2H)-yl)-3-(trifluoromethyl)pyridine, trifluoro acetic acid salt A mixture of 4-[4-chloro-5-(4-fluoro-phenyl)-1H-imidazol-2-yl]-1,2,3,6-tetrahydro-pyridine from step (c) above, 2-chloro-3-trifluoromethyl-pyridine (125 mg, 0.689 mmol, TCI America) and NaHCO$_3$ (84 mg, 1.0 mmol) in NMP (3 mL) was heated at 180° C. in a microwave synthesizer for 0.5 h. The reaction mixture was cooled to RT and was filtered. The filter cake was washed with NMP (2×2 mL) and the combined filtrates were concentrated in vacuo. The residue was dissolved in DMSO (2 mL) and purified by preparative HPLC [gradient 10-85% MeCN (0.1% TFA)/H$_2$O (0.1% TFA)] to give the title compound as a yellow solid. MS (ESI, positive ion) m/z: 423 (M+1).

EXAMPLE 23

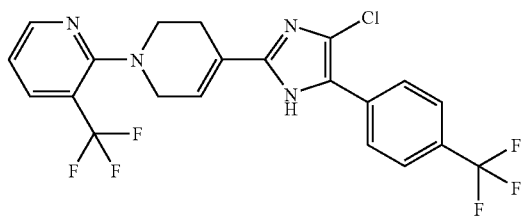

2-(4-(4-Chloro-5-(4-(trifluoromethyl)phenyl)-1H-imidazol-2-yl)-5,6-dihydropyridin-1(2H)-yl)-3-(trifluoromethyl)pyridine

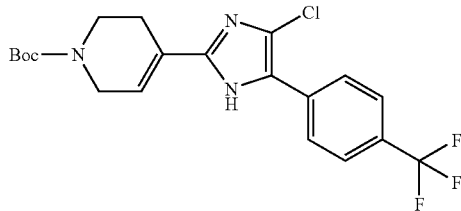

(a) 4-[4-Chloro-5-(4-trifluoromethyl-phenyl)-1H-imidazol-2-yl]-3,6-dihydro-2H-pyridine-1-carboxylic acid tert-butyl ester 4-(4,5-Dichloro-1H-imidazol-2-yl)-3,6-dihydro-2H-pyridine-1-carboxylic acid tert-butyl ester (1.6 g, 5.04 mmol, Example 22(a)) reacted with 4-(trifluoromethyl)benzeneboronic acid (1.05 g, 5.54 mmol, Aldrich) under the conditions of Example 22(b) to give the title compound as a yellow solid. MS (ESI, positive ion) m/z: 428 (M+1).

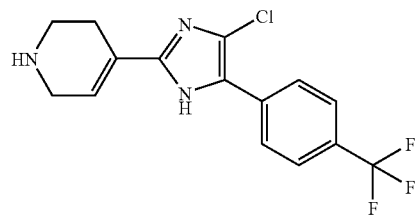

(b) 4-[4-Chloro-5-(4-trifluoromethyl-phenyl)-1H-imidazol-2-yl]-1,2,3,6-tetrahydro-pyridine 4-[4-Chloro-5-(4-trifluoromethyl-phenyl)-1H-imidazol-2-yl]-3,6-dihydro-2H-pyridine-1-carboxylic acid tert-butyl ester from step (a) above (540 mg, 1.26 mmol) reacted with TFA under the conditions of Example 22(c) to give the title compound as a light-brown oil, which was used directly in the next step without additional purification. MS (ESI, positive ion) m/z: 328 (M+1).

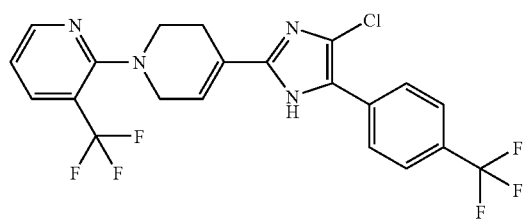

(c) 2-(4-(4-Chloro-5-(4-(trifluoromethyl)phenyl)-1H-imidazol-2-yl)-5,6-dihydropyridin-1(2H)-yl)-3-(trifluoromethyl)pyridine 4-[4-Chloro-5-(4-trifluoromethyl-phenyl)-1H-imidazol-2-yl]-1,2,3,6-tetrahydropyridine from step (b) above reacted with 2-chloro-3-trifluoromethyl-pyridine (251 mg, 1.39 mmol, TCI America) under the conditions of Example 22(d) to give the title compound as a yellow solid. MS (ESI, positive ion) m/z: 473 (M+1).

EXAMPLE 24

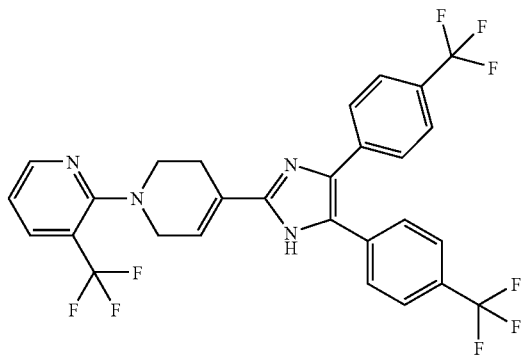

2-(4-(4,5-Bis-(4-(trifluoromethyl)phenyl)-1H-imidazol-2-yl)-5,6-dihydropyridin-1(2H)-yl)-3-(trifluoromethyl)pyridine

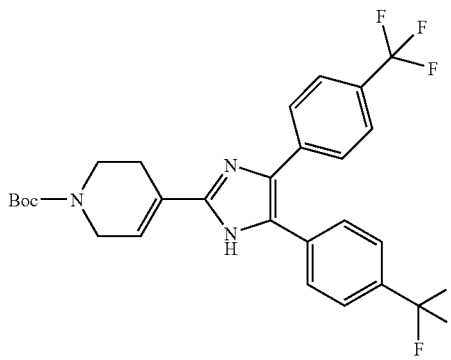

(a) 4-[4,5-Bis-(4-trifluoromethyl-phenyl)-1H-imidazol-2-yl]-3,6-dihydro-2H-pyridine-1-carboxylic acid tert-butyl ester A mixture of 4-(4,5-dichloro-1H-imidazol-2-yl)-3,6-dihydro-2H-pyridine-1-carboxylic acid tert-butyl ester (500. mg, 1.57 mmol, Example 23(a)), 4-(trifluoromethyl)phenylboronic acid (747 mg, 3.93 mmol, Aldrich), dichloro-bis (triphenylphosphine) palladium (II) (441 mg, 0.27 mmol, Aldrich), sodium carbonate (659 mg, 6.28 mmol, Aldrich), and a solution of DME/H$_2$O/EtOH (7:3:2) (10 mL) was heated at 130° C. in a microwave synthesizer for 1 h. The reaction mixture was cooled to RT, filtered, and the filter cake was washed with MeOH (2×10 mL). The combined filtrates were concentrated in vacuo and the residue was purified by silica gel column chromatography (gradient 0-100% EtOAc/hexane) to give the title compound, which was used directly in the next step. MS (ESI, positive ion) m/z: 538 (M+1).

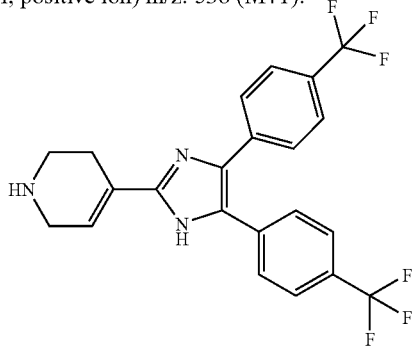

(b) 4-[4,5-Bis-(4-trifluoromethyl-phenyl)-1H-imidazol-2-yl]-1,2,3,6-tetrahydro-pyridine 4-[4,5-Bis-(4-trifluoromethyl-phenyl)-1H-imidazol-2-yl]-3,6-dihydro-2H-pyridine-1-carboxylic acid tert-butyl ester from step (a) above was treated with TFA under the condition of Example 22(c) to give the title compound, which was used directly in the next step without additional purification. MS (ESI, positive ion) m/z: 438 (M+1).

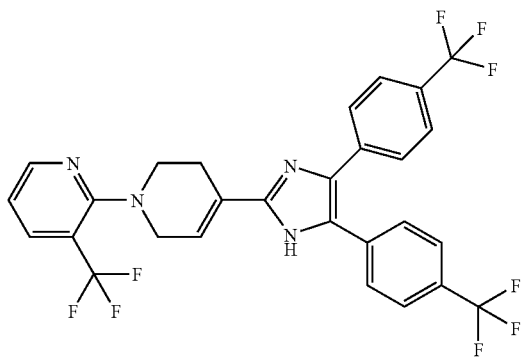

(c) 2-(4-(4,5-Bis-(4-(trifluoromethyl)phenyl)-1H-imidazol-2-yl)-5,6-dihydropyridin-1(2H)-yl)-3-(trifluoromethyl)pyridine 4-[4,5-Bis-(4-trifluoromethyl-phenyl)-1H-imidazol-2-yl]-1,2,3,6-tetrahydropyridine from step (b) above reacted with 2-chloro-3-trifluoromethyl-pyridine (352 mg, 1.95 mmol, TCI America) under the condition of Example 22(d) to give the title compound as a light-yellow solid. MS (ESI, positive ion) m/z: 583 (M+1).

EXAMPLE 25

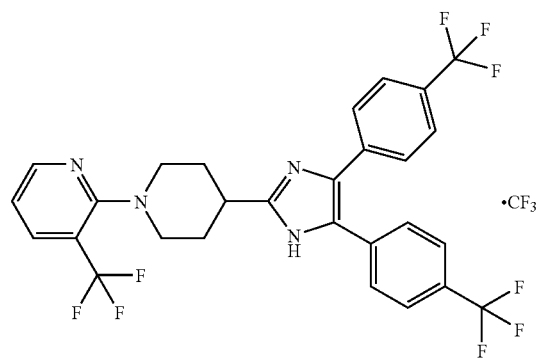

2-(4-(4,5-Bis(4-(trifluoromethyl)phenyl)-1H-imidazol-2-yl)piperidin-1-yl)-3-(trifluoromethyl)pyridine, trifluoroacetic acid salt A mixture of 2-(4-(4,5-bis-(4-(trifluoromethyl)phenyl)-1H-imidazol-2-yl)-5,6-dihydropyridin-1(2H)-yl)-3-(trifluoromethyl)pyridine (91 mg, 0.16 mmol, Example 24(c)) and 10% Pd/C (10 mg, Aldrich) in MeOH (1 mL) was stirred at RT under $H_2$ atmosphere for 48 h. The reaction mixture was filtered from the palladium catalyst through a Celite® pad and the filter cake was washed with MeOH (3×1 mL). The combined filtrates were concentrated in vacuo and the residue was dissolved in DMSO: MeOH (1:1) solution (1 mL) and purified by preparative HPLC [gradient 10-85% MeCN (0.1% TFA)/$H_2O$ (0.1% TFA)] to give 25 mg (27%) of the title compound as a white solid. MS (ESI, positive ion) m/z: 585 (M+1).

EXAMPLE 26

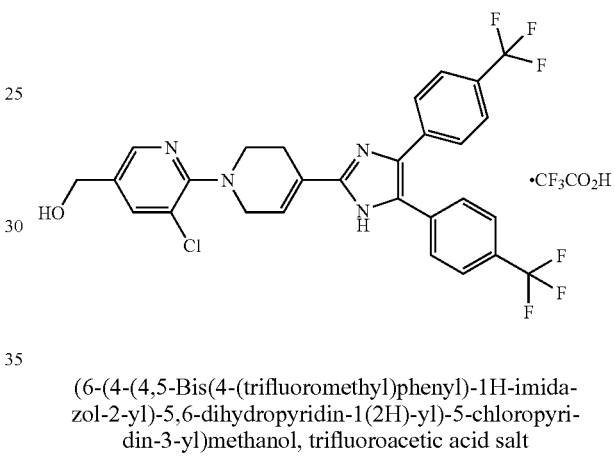

(6-(4-(4,5-Bis(4-(trifluoromethyl)phenyl)-1H-imidazol-2-yl)-5,6-dihydropyridin-1(2H)-yl)-5-chloropyridin-3-yl)methanol, trifluoroacetic acid salt 4-[4,5-Bis-(4-trifluoromethyl-phenyl)-1H-imidazol-2-yl]-1,2,3,6-tetrahydropyridine (25 mg, 0.057 mmol, Example 24(b)) reacted with (5,6-dichloro-pyridin-3-yl)-methanol (11 mg, 0.063 mmol, TCI) under the conditions of Example 22(d). The crude product was purified by preparative HPLC [gradient 10-85% MeCN (0.1% TFA)/$H_2O$ (0.1% TFA)] to give the title compound as a light-yellow solid. MS (ESI, positive ion) m/z: 579 (M+1).

EXAMPLE 27

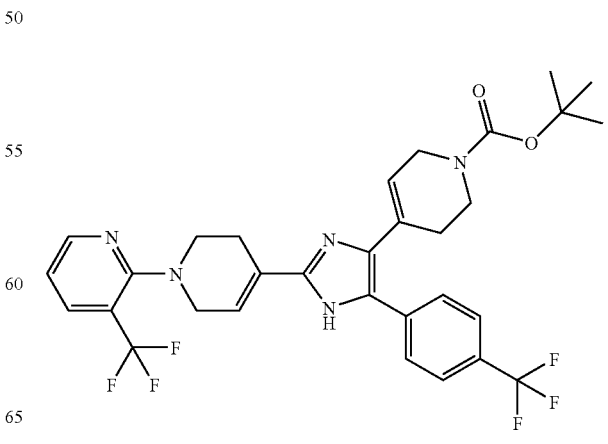

tert-Butyl 4-(5-(4-(trifluoromethyl)phenyl)-2-(1-(3-(trifluoromethyl)pyridin-2-yl)-1,2,3,6-tetrahydropyridin-4-yl)-1H-imidazol-4-yl)-5,6-dihydropyridine-1(2H)-carboxylate A mixture of 2-(4-(4-chloro-5-(4-(trifluoromethyl)phenyl)-1H-imidazol-2-yl)-5,6-dihydropyridin-1(2H)-yl)-3-(trifluoromethyl)pyridine (60 mg, 0.127 mmol, Example 23(c)), 4-(4,4,5,5-tetramethyl-[1,3,2]dioxaborolan-2-yl)-3,6-dihydro-2H-pyridine-1-carboxylic acid tert-butyl ester (59 mg, 0.19 mmol, Chemshop), dichloro-bis(triphenyl-phosphine) palladium (II) (5 mg, 0.006 mmol, Aldrich), sodium carbonate (27 mg, 0.254 mmol), and DME/H$_2$O/EtOH (7:3:2) solution (0.8 mL) was heated at 130° C. in a microwave synthesizer for 2 h. The reaction mixture was cooled to RT and filtered. The filter cake was washed with MeOH (2×1 mL) and the combined filtrates were concentrated in vacuo. The residue was dissolved in DMSO (1 mL) and purified by by preparative HPLC [gradient 10-85% MeCN (0.1% TFA)/H$_2$O (0.1% TFA)]. The fractions containing the desired product were combined and treated with sat. aqueous solution of NaHCO$_3$ (15 mL) at 0° C. for 24 h. The organic layer was separated, dried over MgSO$_4$, and filtered. The filtrate was evaporated and the residue dried in vacuo to give the title compound as an orange solid. MS (ESI, positive ion) m/z: 620 (M+1).

EXAMPLE 28

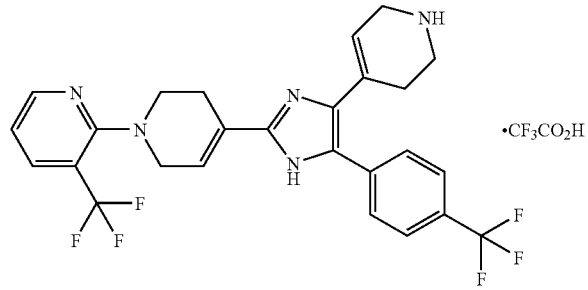

2-(4-(4-(1,2,3,6-Tetrahydropyridin-4-yl)-5-(4-(trifluoromethyl)phenyl)-1H-imidazol-2-yl)-5,6-dihydropyridin-1(2H)-yl)-3-(trifluoromethyl)pyridine, trifluoroacetic acid salt tert-Butyl 4-(5-(4-(trifluoromethyl)phenyl)-2-(1-(3-(trifluoromethyl)pyridin-2-yl)-1,2,3,6-tetrahydropyridin-4-yl)-1H-imidazol-4-yl)-5,6-dihydropyridine-1(2H)-carboxylate (25 mg, 0.04 mmol, Example 27) was treated with TFA under the conditions of Example 22(c). The crude product was purified by preparative HPLC [gradient 10-85% MeCN (0.1% TFA)/H$_2$O (0.1% TFA)] to give the title compound as a light-yellow solid. MS (ESI, positive ion) m/z: 520 (M+1).

EXAMPLE 29

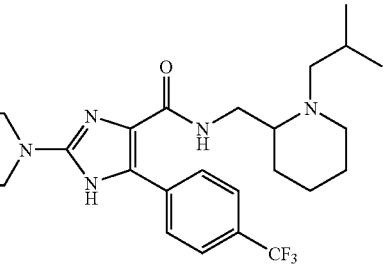

N-((1-Isobutylpiperidin-2-yl)methyl)-5-(4-(trifluoromethyl)phenyl)-2-(4-(3-(trifluoromethyl)pyridin-2-yl)piperazin-1-yl)-1H-imidazole-4-carboxamide

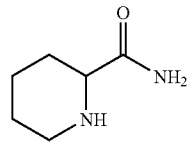

(a) Piperidine-2-carboxamide

A solution of methyl piperidine-2-carboxylate hydrochloride (5 g, 27 mmol, Aldrich) in NH$_4$OH (100 mL) was stirred at RT for 4 h. Then, the mixture was concentrated in vacuo to give the title compound, which was used in the next step without purification. MS (ESI, positive ion) m/z: 129 (M+1).

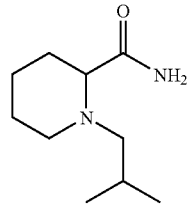

(b) 1-Isobutylpiperidine-2-carboxamide

A solution of piperidine-2-carboxamide from step (a) above in DCE (100 mL) was mixed with isobutyraldehyde (3.23 mL, Aldrich) and sodium-triacetoxyborohydride (7.5 g, Aldrich). The mixture was stirred at RT for 24 h. Then, saturated Na$_2$CO$_3$ (300 mL) was added and the mixture was extracted with EtOAc (2×300 mL). The combined organic extracts were dried over Na$_2$CO$_3$(s) and concentrated. The residue was then taken up in EtOAc (100 mL), dried over Na$_2$CO$_3$(s), and concentrated in vacuo to give the title compound as an off-white solid. MS (ESI, positive ion) m/z: 185 (M+1).

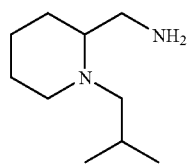

(c) (1-Isobutylpiperidin-2-yl)methanamine

A solution of 1-isobutylpiperidine-2-carboxamide from step (b) above (3.24 g, 17.7 mmol) in THF (100 mL) was treated with lithium aluminum hydride (35.4 mL, 1M in THF, Aldrich) at 0° C. for over 10 min. The mixture was warmed up to 50° C. for 15 h. Then, the mixture was cooled to 0° C. and was quenched carefully with $H_2O$ (1.3 mL), 15% NaOH (1.3 mL), and then $H_2O$ (3 mL). The mixture was stirred at RT for 15 min and was filtered. The filtrate was washed with THF (100 mL), DCM (100 mL), and then DCM with 1% MeOH (2M in $NH_3$). The filtrate was then concentrated in vacuo and the residue was purified on silica gel using ISCO Combiflash® system with DCM/2M methanolic ammonia gradient to give the title compound as pale yellow oil. MS (ESI, positive ion) m/z: 171 (M+1).

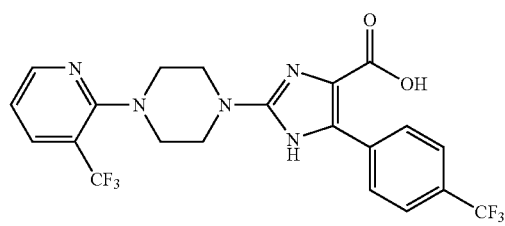

(d) 5-(4-(Trifluoromethyl)phenyl)-2-(4-(3-(trifluoromethyl)pyridin-2-yl)piperazin-1-yl)-1H-imidazole-4-carboxylic acid A solution of 5-(4-(trifluoromethyl)phenyl)-2-(4-(3-(trifluoromethyl)pyridin-2-yl)piperazin-1-yl)-1-((2-(trimethylsilyl)ethoxy)methyl)-1H-imidazole-4-carboxylic acid (90. mg, 0.146 mmol, Example 16(e)) in TFA (1.5 mL) reacted under the condition of Example 16(g) to give the title compound as a white solid. MS (ESI, positive ion) m/z: 486 (M+1).

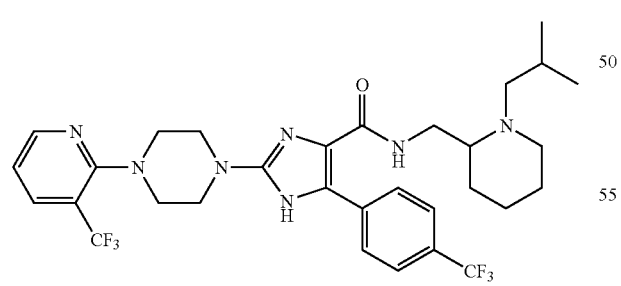

(e) N-((1-Isobutylpiperidin-2-yl)methyl)-5-(4-(trifluoromethyl)phenyl)-2-(4-(3-(trifluoromethyl)pyridin-2-yl)piperazin-1-yl)-1H-imidazole-4-carboxamide A mixture of 5-(4-(trifluoromethyl)phenyl)-2-(4-(3-(trifluoromethyl)pyridin-2-yl)piperazin-1-yl)-1H-imidazole-4-carboxylic acid from step (d) above (50. mg, 0.103 mmol), (1-isobutylpiperidin-2-yl)methanamine (26 mg, 0.15 mmol, Example 29(c)), benzotriazol-1-yloxy-tris(dimethylamino)phosphonium hexafluorophosphate (68 mg, 0.154 mmol, Aldrich), and DIEA (0.053 mL, 0.975 mmol, Aldrich) in DCM (0.6 mL) reacted under the condition of Example 16(f) to give the title compound as a white solid. MS (ESI, positive ion) m/z: 638 (M+1).

EXAMPLE 30

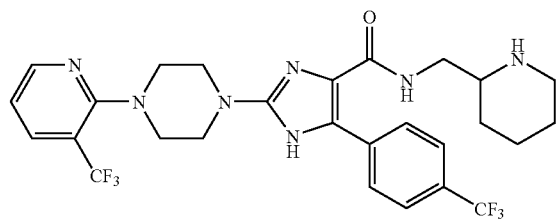

N-(piperidin-2-ylmethyl)-5-(4-(trifluoromethyl)phenyl)-2-(4-(3-(trifluoromethyl)pyridin-2-yl)piperazin-1-yl)-1H-imidazole-4-carboxamide

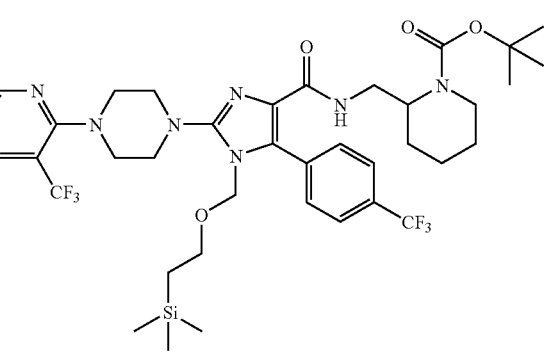

(a) Tert-butyl 2-((5-(4-(trifluoromethyl)phenyl)-2-(4-(3-(trifluoromethyl)pyridin-2-yl)piperazin-1-yl)-1-((2-(trimethylsilyl)ethoxy)methyl)-1H-imidazole-4-carboxamido)methyl)piperidine-1-carboxylate A mixture of 5-(4-(trifluoromethyl)phenyl)-2-(4-(3-(trifluoromethyl)pyridin-2-yl)piperazin-1-yl)-1-((2-(trimethylsilyl)ethoxy)methyl)-1H-imidazole-4-carboxylic acid (300. mg, 0.487 mmol, Example 16(e)), tert-butyl 2-(aminomethyl)piperidine-1-carboxylate (209 mg, 0.974 mmol, Astatech), benzotriazol-1-yloxy-tris(dimethylamino)phosphonium hexafluorophosphate (323 mg, 0.731 mmol, Aldrich), and DIEA (0.25 mL, 0.98 mmol, Aldrich) in DCM (3 mL) reacted under the condition of Example 16(f) to give the title compound as a light purple solid. MS (ESI, positive ion) m/z: 812 (M+1).

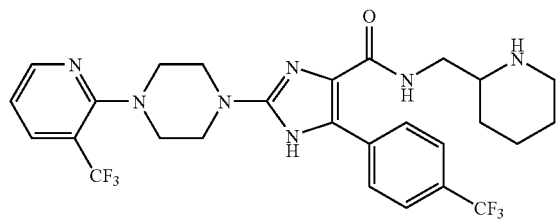

(b) N-(piperidin-2-ylmethyl)-5-(4-(trifluoromethyl)phenyl)-2-(4-(3-(trifluoromethyl)pyridin-2-yl)piperazin-1-yl)-1H-imidazole-4-carboxamide A solution of tert-butyl 2-((5-(4-(trifluoromethyl)phenyl)-2-(4-(3-(trifluoromethyl)pyridin-2-yl)piperazin-1-yl)-1-((2-(trimethylsilyl)ethoxy)methyl)-1H-imidazole-4-carboxamido)methyl)piperidine-1-carboxylate from step (a) above (200. mg, 0.247 mmol) in TFA:DCM (4:1) was stirred at RT for 7 min. The solvent was removed and the residue was added H$_2$O (0.5 mL). Then, saturated NaHCO$_3$ was added at 0° C. until pH ~7 and the solvents were removed. The residue was purified on silica gel using ISCO Combiflash® system with DCM/2M methanolic ammonia gradient to give the title compound as a light yellow solid. MS (ESI, positive ion) m/z: 582 (M+1).

EXAMPLE 31

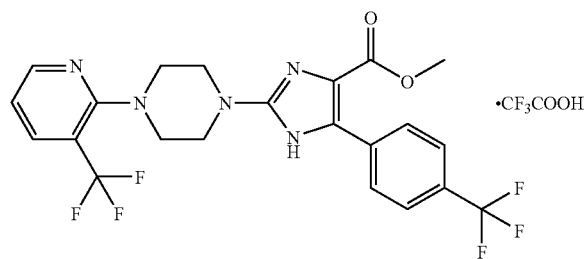

Methyl 4-(4-(trifluoromethyl)phenyl)-2-(4-(3-(trifluoromethyl)pyridin-2-yl)piperazin-1-yl)-1H-imidazole-5-carboxylate, trifluoroacetic acid salt

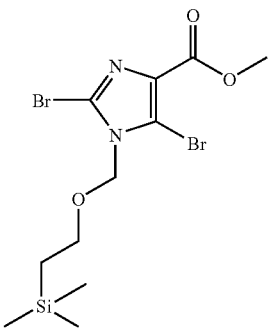

(a) 2,5-Dibromo-1H-imidazole-4-carboxylic acid methyl ester

1H-Imidazole-4-carboxylic acid methyl ester (1.8 g, 14 mmol, Aldrich) reacted with bromine (1.6 mL, 29.8 mmol, Adrich) in acetic acid (20 mL) was stirred at RT for 12 h. The reaction mixture was filtered from the yellow precipitate, and the filter cake was washed with DCM (2×20 mL). The cake was mixed with sat. aqueous solution of NaHCO$_3$ (100 mL) and EtOAc (200 mL), and the mixture was stirred for 1 h at RT. The organic layer was separated and the aqueous phase was extracted with EtOAc (2×200 mL). The organic extracts were combined, dried over MgSO$_4$ and filtered. The filtrate was concentrated and the residue was purified by preparative HPLC [gradient 10-85% MeCN (0.1% TFA)/H$_2$O (0.1% TFA)] to give the title compound as light-yellow solid. MS (ESI, positive ion) m/z: 282, 284 (M+I).

(b) Methyl 2,5-dibromo-1-((2-(trimethylsilyl)ethoxy)methyl)-1H-imidazole-4-carboxylate A mixture of 2-(trimethylsilyl)ethoxymethyl chloride (0.49 mL, 2.76 mmol, Aldrich), and sodium hydride (48 mg, 2.02 mmol, Aldrich) in THF (5 mL) was stirred at RT for 0.1 h. A solution of 2,5-dibromo-1H-imidazole-4-carboxylic acid methyl ester from step (a) above (520 mg, 1.84 mmol) in THF (5 mL) was added dropwise to the stirred reaction mixture, and the stirring was continued for 12 h at RT. The reaction mixture was diluted with H$_2$O (20 mL), and extracted with EtOAc (2×50 mL). The combined organic extracts were dried over MgSO$_4$, filtered, and the filtrate concentrated in vacuo. The residue was purified by silica gel column chromatography (gradient 10-50% EtOAc/hexane) to give the title compound as colorless oil.

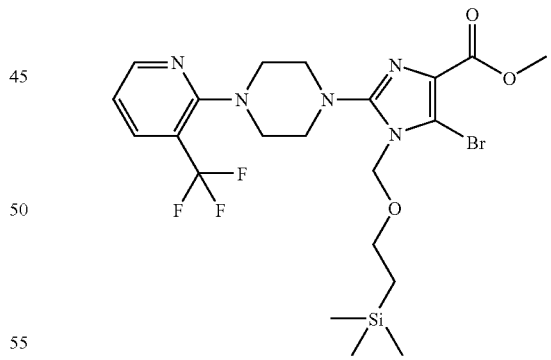

(c) Methyl 5-bromo-2-(4-(3-(trifluoromethyl)pyridin-2-yl)piperazin-1-yl)-1-((2-(trimethylsilyl)ethoxy)methyl)-1H-imidazole-4-carboxylate A mixture of methyl 2,5-dibromo-1-((2-(trimethylsilyl)ethoxy)methyl)-1H-imidazole-4-carboxylate from step (b) above (100. mg, 0.24 mmol) and 1-(3-trifluoromethyl-pyridin-2-yl)-piperazine (277 mg, 1.2 mmol, Oakwood) was heated at 130° C. in a microwave synthesizer for 15 min. The reaction mixture was cooled to RT, diluted with MeOH (2 mL), and purified by preparative HPLC [gradient 10-85%

MeCN (0.1% TFA)/H₂O (0.1% TFA)]. The fractions containing the desired product were combined and treated with sat. aqueous solution of NaHCO₃ (15 mL). The organic layer was separated, dried over MgSO₄, and filtered. The filtrate was evaporated and the residue dried in vacuo to give the title compound as a light-yellow oil. MS (ESI, positive ion) m/z: 564 (M+1).

EXAMPLE 32

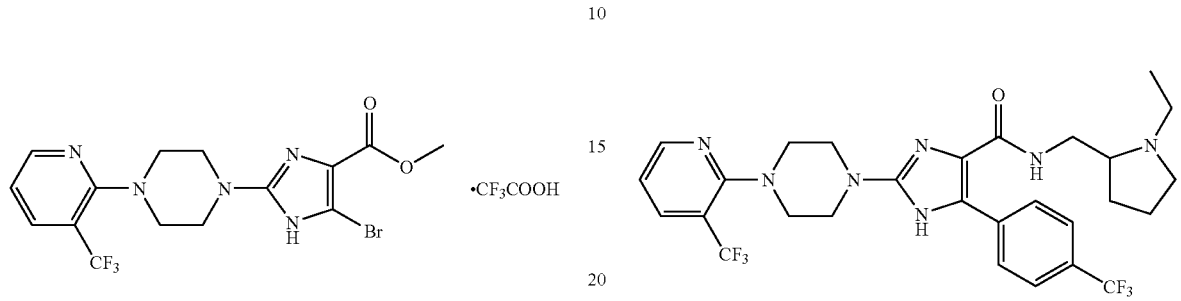

(d) Methyl 5-bromo-2-(4-(3-(trifluoromethyl)pyridin-2-yl)piperazin-1-yl)-1H-imidazole-4-carboxylate, trifluoroacetic acid salt A solution of methyl 5-bromo-2-(4-(3-(trifluoromethyl)pyridin-2-yl)piperazin-1-yl)-1-((2-(trimethylsilyl)ethoxy)methyl)-1H-imidazole-4-carboxylate from step (c) above (30 mg, 0.053 mmol) in TFA (0.5 mL) was stirred at RT for 0.75 h. The solvent was removed and the residue was dissolved in MeOH (0.5 mL), and purified by preparative HPLC [gradient 10-85% MeCN (0.1% TFA)/H₂O (0.1% TFA)] to give the title compound as a white solid. MS (ESI, positive ion) m/z: 435 (M+1).

N-((1-Ethylpyrrolidin-2-yl)methyl)-5-(4-(trifluoromethyl)phenyl)-2-(4-(3-(trifluoromethyl)pyridin-2-yl)piperazin-1-yl)-1H-imidazole-4-carboxamide A mixture of 5-(4-(trifluoromethyl)phenyl)-2-(4-(3-(trifluoromethyl)pyridin-2-yl)piperazin-1-yl)-1-((2-(trimethylsilyl)ethoxy)methyl)-1H-imidazole-4-carboxylic acid (200. mg, 0.325 mmol, Example (16e)), (1-ethylpyrrolidin-2-yl)methanamine (83 mg, 0.65 mmol, Acros), benzotriazol-1-yloxy-tris(dimethylamino)phosphonium hexafluorophosphate (216 mg, 0.487 mmol, Aldrich), and DIEA (0.170 mL, 0.975 mmol, Aldrich) in DCM (2 mL) reacted under the condition of Example 16(f) and Example 16(g) to give the title compound as a light yellow solid. MS (ESI, positive ion) m/z: 596 (M+1).

EXAMPLE 33

(e) Methyl 4-(4-(trifluoromethyl)phenyl)-2-(4-(3-(trifluoromethyl)pyridin-2-yl)piperazin-1-yl)-1H-imidazole-5-carboxylate, trifluoroacetic acid salt Methyl 5-bromo-2-(4-(3-(trifluoromethyl)pyridin-2-yl)piperazin-1-yl)-1H-imidazole-4-carboxylate, trifluoroacetic acid salt (29 mg, 0.067 mmol, Example 31(d)) reacted with 4-(trifluoromethyl)phenylboronic acid (15 mg, 0.08 mmol, Aldrich) under the condition of Example 24(a). The crude product was purified by preparative HPLC [gradient 10-85% MeCN (0.1% TFA)/H₂O (0.1% TFA)] to give the title compound as colorless oil. MS (ESI, positive ion) m/z: 500 (M+1).

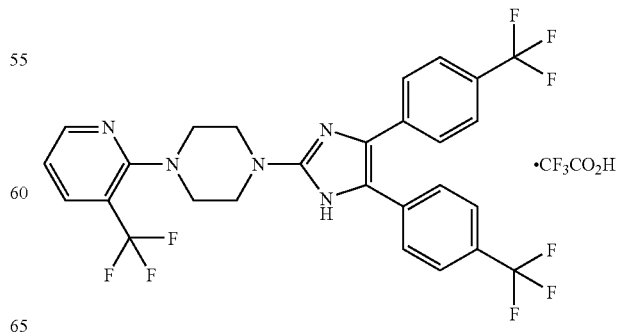

1-[4,5-Bis-(4-trifluoromethyl-phenyl)-1H-imidazol-2-yl]-4-(3-trifluoromethyl-pyridin-2-yl)-piperazine, trifluoroacetic acid salt

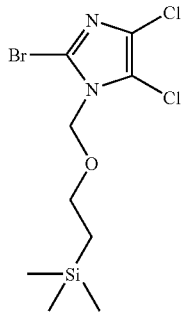

(a) 2-Bromo-4,5-dichloro-1-((2-(trimethylsilyl)ethoxy)methyl)-1H-imidazole

2-Bromo-4,5-dichloro-1H-imidazole (25 g, 117 mmol, Aldrich) reacted with 2-(trimethylsilyl)ethoxymethyl chloride (23 mL, 129 mmol, Aldrich) under the condition of Example 31(b) to give the title compound as a light-yellow oil.

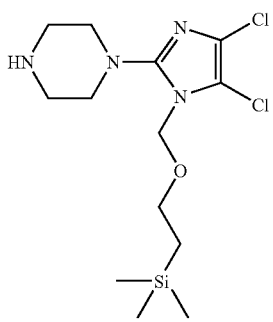

(b) 1-(4,5-Dichloro-1-((2-(trimethylsilyl)ethoxy)methyl)-1H-imidazol-2-yl)piperazine A mixture of 2-bromo-4,5-dichloro-1-((2-(trimethylsilyl)ethoxy)methyl)-1H-imidazole from step (a) above (10. g, 29 mmol) and piperazine (20. g, 230 mmol, Aldrich) was heated at 130° C. in a microwave synthesizer for 0.25 h. The reaction mixture was cooled to RT and diluted with DCM (50 mL). The solution was purified by silica gel column chromatography eluting with DCM/2M NH$_3$ in MeOH (20:1) to give the title compound as a yellow oil. MS (ESI, positive ion) m/z: 351 (M+1).

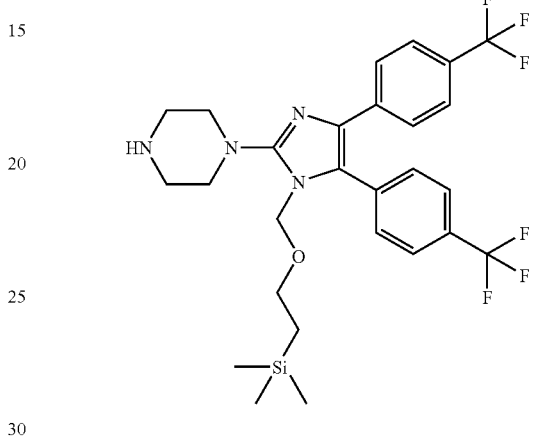

(c) 1-(4,5-Bis(4-(trifluoromethyl)phenyl)-1-((2-(trimethylsilyl)ethoxy)methyl)-1H-imidazol-2-yl)piperazine 1-(4,5-Dichloro-1-((2-(trimethylsilyl)ethoxy)methyl)-1H-imidazol-2-yl)piperazine from step (b) above (300. mg, 0.86 mmol) reacted with 4-(trifluoromethyl)phenylboronic acid (326 mg, 1.71 mmol, Aldrich) under the condition of Example 24(a) to give the title compound, which was used directly in the next step without additional purification. MS (ESI, positive ion) m/z: 571 (M+1).

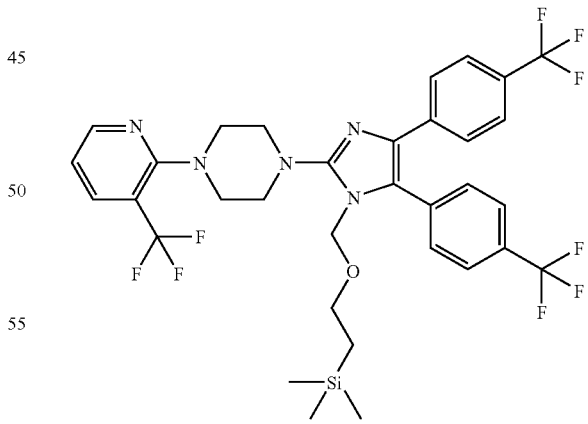

(d) 1-(4,5-Bis(4-(trifluoromethyl)phenyl)-1-((2-(trimethylsilyl)ethoxy)methyl)-1H-imidazol-2-yl)-4-(3-(trifluoromethyl)pyridin-2-yl)piperazine 1-(4,5-Bis(4-(trifluoromethyl)phenyl)-1-((2-(trimethylsilyl)ethoxy)methyl)-1H-imidazol-2-yl)piperazine from step (c) above reacted with 2-chloro-3-trifluoromethyl-pyridine (40 mg, TCI America) under the condition of Example 22(d)

to give the title compound, which was used directly in the next step without additional purification MS (ESI, positive ion) m/z: 716 (M+1).

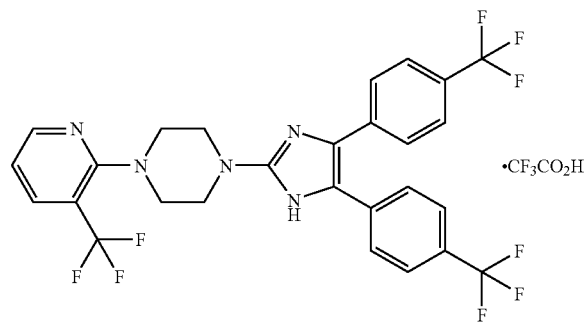

(e) 1-[4,5-Bis-(4-trifluoromethyl-phenyl)-1H-imidazol-2-yl]-4-(3-trifluoromethyl-pyridin-2-yl)-piperazine, trifluoroacetic acid salt 1-(4,5-Bis(4-(trifluoromethyl)phenyl)-1-((2-(trimethylsilyl)ethoxy)methyl)-1H-imidazol-2-yl)-4-(3-(trifluoromethyl)pyridin-2-yl)piperazine from step (d) above reacted with TFA (1 mL) under the conditions of Example 31(d). The crude product was purified by preparative HPLC [gradient 10-85% MeCN (0.1% TFA)/H$_2$O (0.1% TFA)] to give the title compound as a light-yellow solid. MS (ESI, positive ion) m/z: 586 (M+1).

EXAMPLE 34

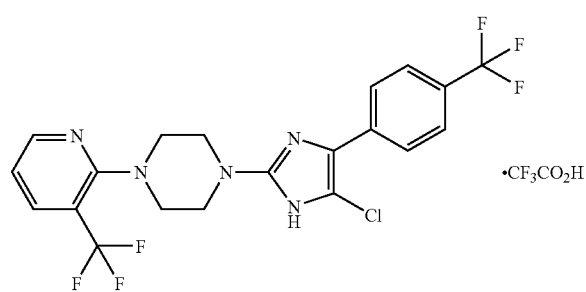

1-(5-Chloro-4-(4-(trifluoromethyl)phenyl)-1H-imidazol-2-yl)-4-(3-(trifluoromethyl)pyridin-2-yl)piperazine, trifluoroacetic acid salt

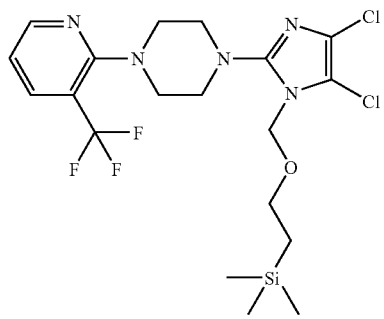

(a) 1-(4,5-Dichloro-1-((2-(trimethylsilyl)ethoxy)methyl)-1H-imidazol-2-yl)-4-(3-(trifluoromethyl)pyridin-2-yl)piperazine 2-Bromo-4,5-dichloro-1-((2-(trimethylsilyl)ethoxy)methyl)-1H-imidazole (1.2 g, 3.5 mmol, Example 33(a)) reacted with 1-(3-trifluoromethyl-pyridin-2-yl)piperazine (4 g, 17 mmol, Oakwood) under the conditions of Example 31(c) to give the title compound as a colorless oil. MS (ESI, positive ion) m/z: 496 (M+1).

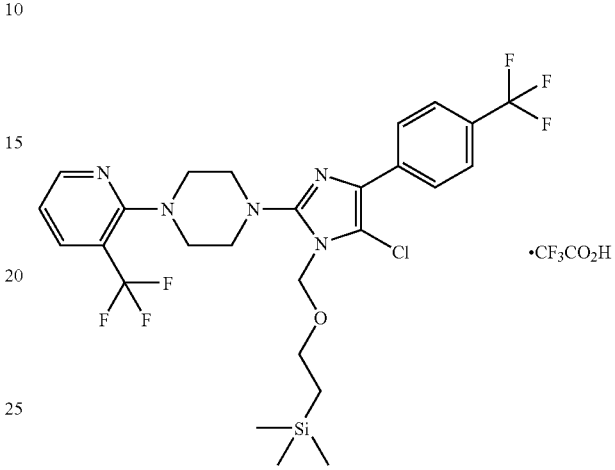

(b) 1-(5-Chloro-4-(4-(trifluoromethyl)phenyl)-1-((2-(trimethylsilyl)ethoxy)methyl)-1H-imidazol-2-yl)-4-(3-(trifluoromethyl)pyridin-2-yl)piperazine, trifluoroacetic acid salt 1-(4,5-Dichloro-1-((2-(trimethylsilyl)ethoxy)methyl)-1H-imidazol-2-yl)-4-(3-(trifluoromethyl)pyridin-2-yl)piperazine from step (a) above (96 mg, 0.19 mmol) reacted with (4-trifluoromethyl)phenylboronic acid (147 mg, 0.772 mmol, Aldrich) under the condition of Example 24(a). The crude product was purified by preparative HPLC [gradient 10-85% MeCN (0.1% TFA)/H$_2$O (0.1% TFA)] to give the title compound, which was used directly in the next step. MS (ESI, positive ion) m/z: 606 (M+1).

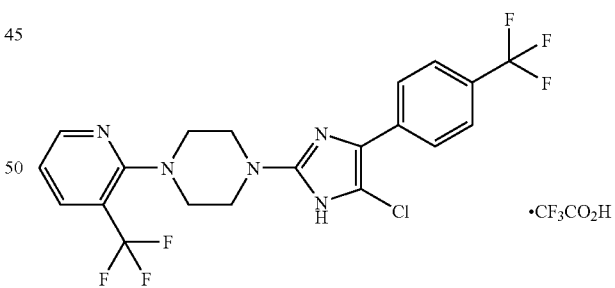

(c) 1-(5-Chloro-4-(4-(trifluoromethyl)phenyl)-1H-imidazol-2-yl)-4-(3-(trifluoromethyl)pyridin-2-yl)piperazine, trifluoroacetic acid salt 1-(5-Chloro-4-(4-(trifluoromethyl)phenyl)-1-((2-(trimethylsilyl)ethoxy)methyl)-1H-imidazol-2-yl)-4-(3-(trifluoromethyl)pyridin-2-yl)piperazine, trifluoroacetic acid salt from step (b) above reacted with TFA (1 mL) under the conditions of Example 31(d). The crude product was purified by preparative HPLC [gradient 10-85% MeCN (0.1% TFA)/H$_2$O (0.1% TFA)] to give the title compound as a light-yellow solid. MS (ESI, positive ion) m/z: 476 (M+1).

EXAMPLE 35

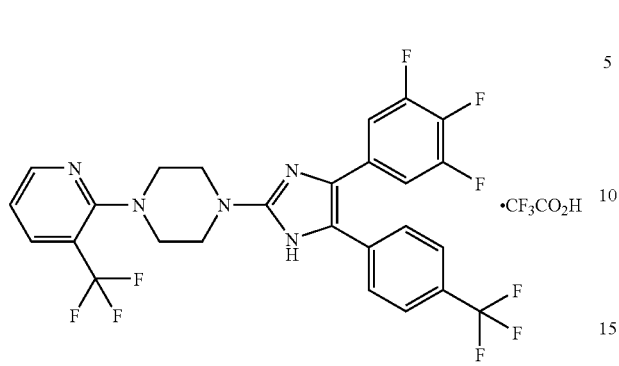

1-(5-(4-(Trifluoromethyl)phenyl)-4-(3,4,5-trifluorophenyl)-1H-imidazol-2-yl)-4-(3-(trifluoromethyl)pyridin-2-yl)piperazine, trifluoroacetic acid salt

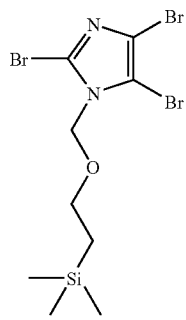

(a) 2,4,5-Tribromo-1-((2-(trimethylsilyl)ethoxy)methyl)-1H-imidazole 2,4,5-Tribromo-1H-imidazole (10. g, 33 mmol, Aldrich) reacted with 2-(trimethylsilyl)ethoxymethyl chloride (9 mL, 50 mmol, Aldrich) under the conditions of Example 31(b) to give the title compound as a white solid.

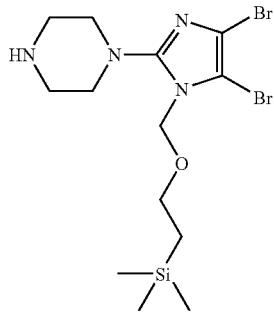

(b) 1-(4,5-Dibromo-1-((2-(trimethylsilyl)ethoxy)methyl)-1H-imidazol-2-yl)piperazine 2,4,5-Tribromo-1-((2-(trimethylsilyl)ethoxy)methyl)-1H-imidazole from step (a) above (26.5 g, 61.3 mmol) reacted with piperazine (42 g, 490 mmol, Aldrich) under the conditions of Example 33(b) to give the title compound as a yellow oil. MS (ESI, positive ion) m/z: 439 (M+1).

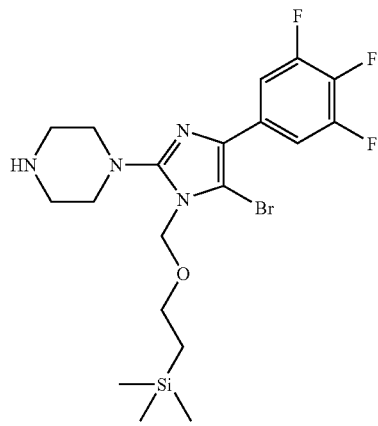

(c) 1-(5-Bromo-4-(3,4,5-trifluorophenyl)-1-((2-(trimethylsilyl)ethoxy)methyl)-1H-imidazol-2-yl)piperazine 1-(4,5-Dibromo-1-((2-(trimethylsilyl)ethoxy)methyl)-1H-imidazol-2-yl)piperazine from step (b) above reacted with (3,4,5-trifluoromethyl)phenylboronic acid (240. mg, 1.37 mmol, Combi-blocks) under the condition of Example 24(a). The crude product was purified by preparative HPLC [gradient 10-85% MeCN (0.1% TFA)/H$_2$O (0.1% TFA)]. The fractions containing the desired product were combined and treated with sat. aqueous solution of NaHCO$_3$ (15 mL). The organic phase was separated and the aqueous solution was extracted with EtOAc (2×15 mL). The organic extracts were combined, dried over MgSO$_4$, filtered, and evaporated in vacuo to give the title compound as a yellow solid. MS (ESI, positive ion) m/z: 491 (M+1).

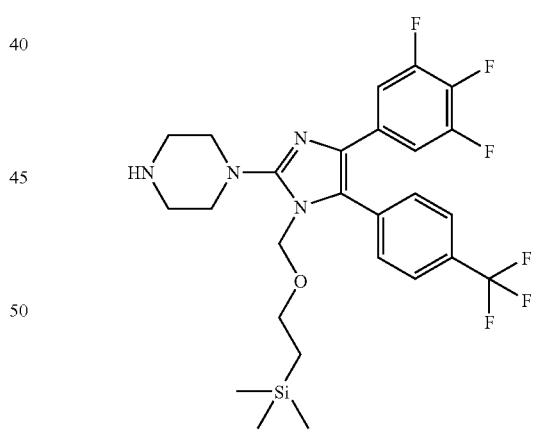

(d) 1-(5-(4-(Trifluoromethyl)phenyl)-4-(3,4,5-trifluorophenyl)-1-((2-(trimethylsilyl)ethoxy)methyl)-1H-imidazol-2-yl)piperazine.

1-(5-Bromo-4-(3,4,5-trifluorophenyl)-1-((2-(trimethylsilyl)ethoxy)methyl)-1H-imidazol-2-yl)piperazine from step (c) above (549 mg, 1.12 mmol) reacted with (4-trifluoromethyl)phenylboronic acid (213 mg, 1.12 mmol, Aldrich) under the conditions of Example 24(a) to give the title compound as a light-brown solid. MS (ESI, positive ion) m/z: 557 (M+1).

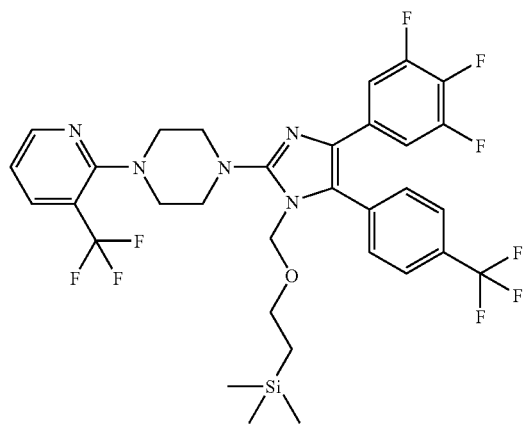

(e) 1-(5-(4-(Trifluoromethyl)phenyl)-4-(3,4,5-trifluorophenyl)-1-((2-(trimethylsilyl)ethoxy)methyl)-1H-imidazol-2-yl)-4-(3-(trifluoromethyl)pyridin-2-yl)piperazine 1-(5-(4-(Trifluoromethyl)phenyl)-4-(3,4,5-trifluorophenyl)-1-((2-(trimethylsilyl)-ethoxy)methyl)-1H-imidazol-2-yl)piperazine from step (d) above (150. mg, 0.269 mmol) reacted with 2-chloro-3-trifluoromethyl-pyridine (49 mg, 0.269 mmol, TCI America) under the condition of Example 22(d) to give the title compound as a light-yellow solid. MS (ESI, positive ion) m/z: 702 (M+1).

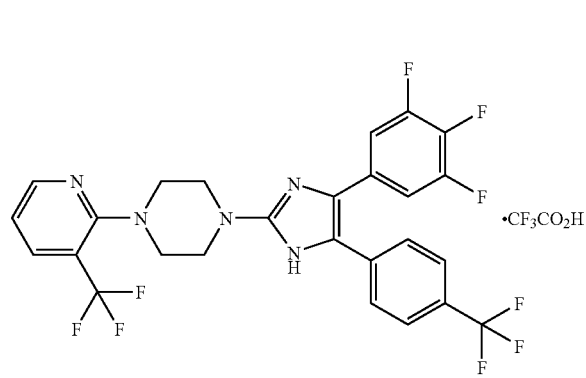

(f) 1-(5-(4-(Trifluoromethyl)phenyl)-4-(3,4,5-trifluorophenyl)-1H-imidazol-2-yl)-4-(3-(trifluoromethyl)pyridin-2-yl)piperazine, trifluoroacetic acid salt 1-(5-(4-(Trifluoromethyl)phenyl)-4-(3,4,5-trifluorophenyl)-1-((2-(trimethylsilyl)-ethoxy)methyl)-1H-imidazol-2-yl)-4-(3-(trifluoromethyl)pyridin-2-yl)piperazine from step (e) above (105 mg, 0.15 mmol) reacted with TFA (2 mL) under the conditions of Example 31(d). The crude product was purified by preparative HPLC [gradient 10-85% MeCN (0.1% TFA)/H$_2$O (0.1% TFA)] to give the title compound as a white solid. MS (ESI, positive ion) m/z: 572 (M+1).

EXAMPLE 36

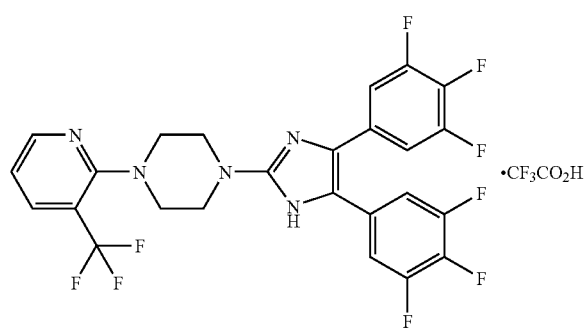

1-(4,5-Bis(3,4,5-trifluorophenyl)-1H-imidazol-2-yl)-4-(3-(trifluoromethyl)pyridin-2-yl)piperazine, trifluoroacetic acid salt

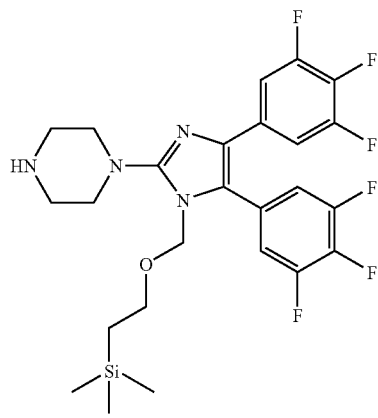

(a) 1-(4,5-Bis(3,4,5-trifluorophenyl)-1-((2-(trimethylsilyl)ethoxy)methyl)-1H-imidazol-2-yl)piperazine 1-(4,5-Dibromo-1-((2-(trimethylsilyl)ethoxy)methyl)-1H-imidazol-2-yl)piperazine (2.3 g, 5.25 mmol, Example 35(b)) reacted with 3,4,5-trifluorophenylboronic acid (462 mg, 2.63 mmol, Combi-blocks) under the conditions of Example 24(a) to give the title compound as a yellow oil. MS (ESI, positive ion) m/z: 543 (M+1).

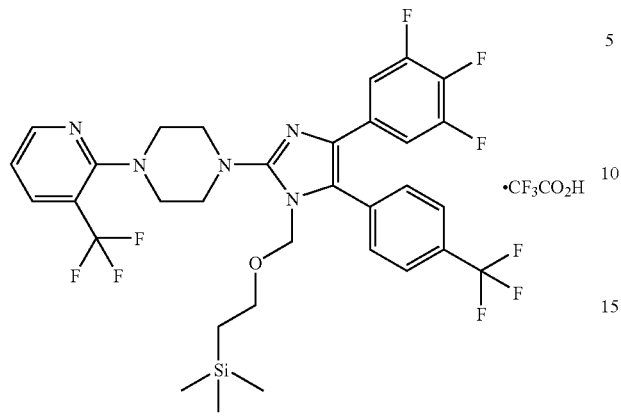

(b) 1-(5-(4-(Trifluoromethyl)phenyl)-4-(3,4,5-trifluorophenyl)-1-((2-(trimethylsilyl)ethoxy)methyl)-1H-imidazol-2-yl)-4-(3-(trifluoromethyl)pyridin-2-yl)piperazine, trifluoroacetic acid salt 1-(4,5-Bis(3,4,5-trifluorophenyl)-1-((2-(trimethylsilyl)ethoxy)methyl)-1H-imidazol-2-yl)piperazine from step (a) above (230. mg, 0.424 mmol) reacted with 2-chloro-3-trifluoromethyl-pyridine (76 mg, 0.424 mmol, TCI America) under the condition of Example 22(d). The crude product was purified by preparative HPLC [gradient 10-85% MeCN (0.1% TFA)/H$_2$O (0.1% TFA)] to give the title compound as a yellow oil, which was used directly in the next step. MS (ESI, positive ion) m/z: 688 (M+1).

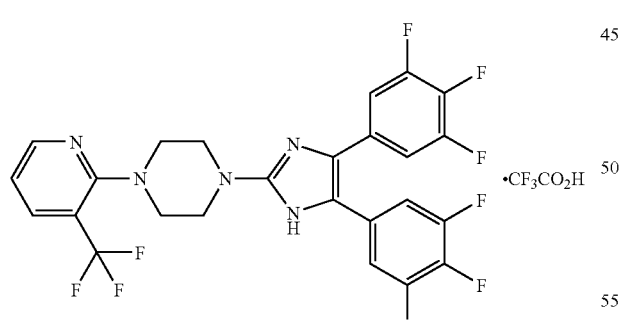

(c) 1-(4,5-Bis(3,4,5-trifluorophenyl)-1H-imidazol-2-yl)-4-(3-(trifluoromethyl)pyridin-2-yl)piperazine, trifluoroacetic acid salt 1-(5-(4-(Trifluoromethyl)phenyl)-4-(3,4,5-trifluorophenyl)-1-((2-(trimethylsilyl)ethoxy)methyl)-1H-imidazol-2-yl)-4-(3-(trifluoromethyl)pyridin-2-yl)-piperazine, trifluoroacetic acid salt from step (b) above reacted with TFA (1 mL) under the conditions of Example 31(d). The crude product was purified by preparative HPLC [gradient 10-85% MeCN (0.1% TFA)/H$_2$O (0.1% TFA)] to give the title compound as a white solid. MS (ESI, positive ion) m/z: 558 (M+1).

EXAMPLE 37

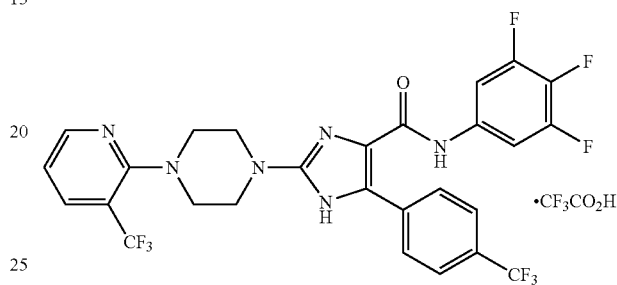

5-(4-(Trifluoromethyl)phenyl)-2-(4-(3-(trifluoromethyl)pyridin-2-yl)piperazin-1-yl)-N-(3,4,5-trifluorophenyl)-1H-imidazole-4-carboxamide, trifluoroacetic acid salt

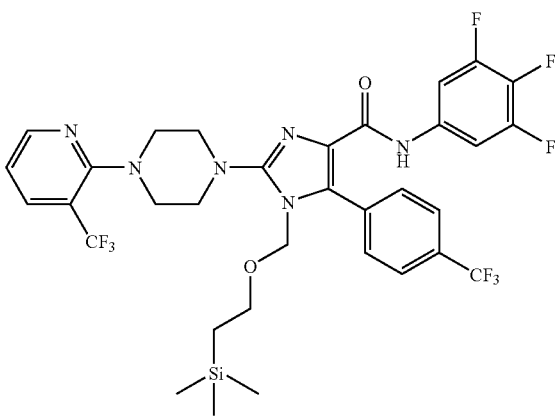

(a) 5-(4-(trifluoromethyl)phenyl)-2-(4-(3-(trifluoromethyl)pyridin-2-yl)piperazin-1-yl)-N-(3,4,5-trifluorophenyl)-1-((2-(trimethylsilyl)ethoxy)methyl)-1H-imidazole-4-carboxamide A mixture of 5-(4-(trifluoromethyl)phenyl)-2-(4-(3-(trifluoromethyl)pyridin-2-yl)piperazin-1-yl)-1-((2-(trimethylsilyl)ethoxy)methyl)-1H-imidazole-4-carboxylic acid (100. mg, 0.162 mmol, Example 16(e)), 3,4,5-trifluoroaniline (36 mg, 0.243 mmol, Aldrich), PS-carbodiimide (189 mg, 0.243 mmol, Argonaut Technologies Inc.), and HOAt (11 mg, 0.081 mmol, Perseptive Biosystems) in a solution of DMF/DCM (1:3) (1 mL) was stirred at RT for 16 h. The mixture was filtered and the resin was washed with MeOH (2×5 mL). The filtrate was concentrated in vacuo and dried under vacuum to give the title compound, which was used in the next step without purification. MS (ESI, positive ion) m/z: 745 (M+1).

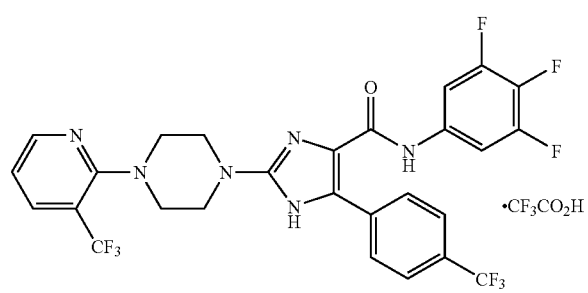

(b) 5-(4-(Trifluoromethyl)phenyl)-2-(4-(3-(trifluoromethyl) pyridin-2-yl)piperazin-1-yl)-N-(3,4,5-trifluorophenyl)-1H-imidazole-4-carboxamide trifluoroacetic acid A solution of 5-(4-(trifluoromethyl)phenyl)-2-(4-(3-(trifluoromethyl)pyridin-2-yl)piperazin-1-yl)-N-(3,4,5-trifluorophenyl)-1-((2-(trimethylsilyl)ethoxy)methyl)-1H-imidazole-4-carboxamide from step (a) above in TFA (2 mL) reacted under the condition of Example 16(g) to give the title compound as a yellow solid. MS (ESI, positive ion) m/z: 615 (M+1).

EXAMPLE 38

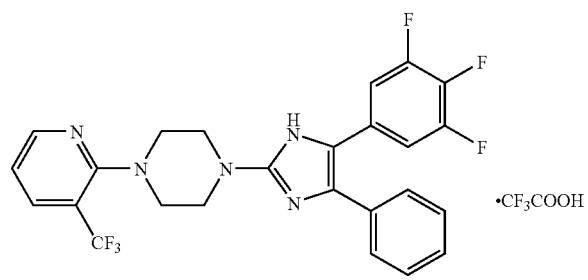

1-(4-Phenyl-5-(3,4,5-trifluorophenyl)-1H-imidazol-2-yl)-4-(3 (trifluoromethyl)pyridin-2-yl)piperazine, trifluoroacetic acid salt

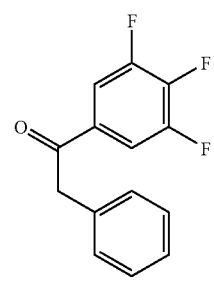

(a) 2-Phenyl-1-(3,4,5-trifluorophenyl)ethanone

A solution of CuCN (190 mg, 2.12 mmol, Aldrich) and LiBr (370. mg, 4.26 mmol, Aldrich) in THF (10 mL) was cooled to −50° C. and to this was added benzyl zinc(II) bromide (0.473 g, 2.00 mmol, Rieke Metals) followed by 3,4,5-trifluorobenzoyl chloride (0.368 g, 1.89 mmol, Oakwood) and under the conditions of Example 7(a). The crude product was purified on silica gel using ISCO Combiflash® system with EtOAc/Hexanes (1:10) as the eluant to give the title compound as a yellow amorphous solid. MS (ESI, pos. ion) m/z: 251

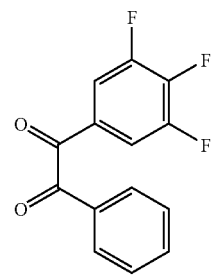

(b) 1-Phenyl-2-(3,4,5-trifluorophenyl)ethane-1,2-dione

A solution of 2-phenyl-1-(3,4,5-trifluorophenyl)ethanone from step (a) above (0.18 g, 0.74 mmol) and N-bromosuccimide (0.295 g, 1.66 mmol, Aldrich) in DMSO (5.5 mL) was reacted under the conditions of Example 7(b). The crude product was purified on silica gel using ISCO Combiflash® system with EtOAc/Hexanes (1:10) as the eluant to give the title compound as a yellow amorphous solid. MS (ESI, pos. ion) m/z: 265

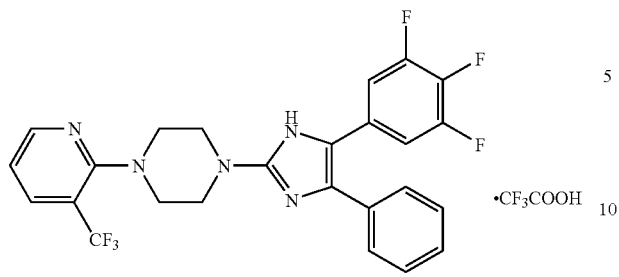

(c) (R)-1-(4,5-Bis(4-(trifluoromethyl)phenyl)-1H-imidazol-2-yl)-2-methyl-4-(3-(trifluoromethyl)pyridin-2-yl)piperazine 1-Phenyl-2-(3,4,5-trifluorophenyl)ethane-1,2-dione from step (b) above (108 mg, 0.41 mmol) reacted with 4-(3-(trifluoromethyl)pyridin-2-yl)piperazine-1-carboxamidine (81 mg, 0.30 mmol, Example 3(a)) under the conditions of Example 4(b). The crude product was purified by preparative HPLC [gradient 10-90% MeCN (0.1% TFA)/H₂O (0.1% TFA)] to give the title compound as an amorphous solid. MS (ESI, pos. ion) m/z: 504 (M+1).

EXAMPLE 39

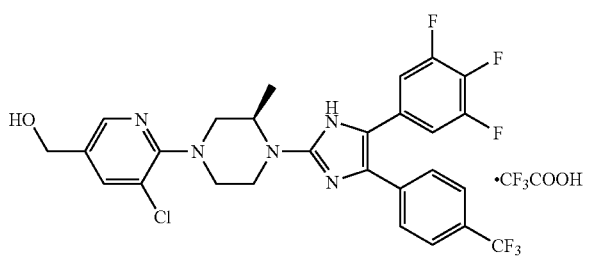

(R)-(5-Chloro-6-(3-methyl-4-(4-(4-(trifluoromethyl)phenyl)-5-(3,4,5-trifluorophenyl)-1H-imidazol-2-yl)piperazin-1-yl)pyridin-3-yl)methanol, trifluoroacetic acid salt

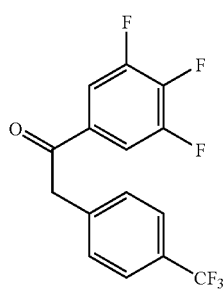

(a) 2-(4-(Trifluoromethyl)phenyl)-1-(3,4,5-trifluorophenyl)ethanone

A solution of CuCN (2.39 g, 26.7 mmol, Aldrich) and LiBr (4.73 g, 54.5 mmol, Aldrich) in THF (50 mL) was cooled to −50° C. and to this was added (4-(trifluoromethyl)benzyl)zinc(II) bromide (7.76 g, 25.5 mmol, Rieke Metals) followed by 3,4,5-trifluorobenzoyl chloride (4.97 g, 25.6 mmol, Oakwood) and under the conditions of Example 7(a). The crude product was purified on silica gel using ISCO Combiflash® system with EtOAc/Hexanes (1:10) as the eluant to give the title compound as a yellow amorphous solid. MS (ESI, pos. ion) m/z: 319

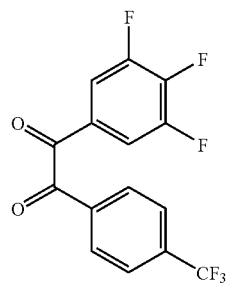

(b) 1-(4-(Trifluoromethyl)phenyl)-2-(3,4,5-trifluorophenyl)ethane-1,2-dione

A solution of 2-(4-(trifluoromethyl)phenyl)-1-(3,4,5-trifluorophenyl)ethanone from step (a) above (1.2 g, 3.77 mmol) and N-bromosuccimide (1.34 g, 7.54 mmol, Aldrich) in DMSO (20 mL) was reacted under the conditions of Example 7(b). The crude product was purified on silica gel using ISCO Combiflash® system with EtOAc/Hexanes (1:10) as the eluant to give the title compound as a yellow amorphous solid. MS (ESI, pos. ion) m/z: 333.

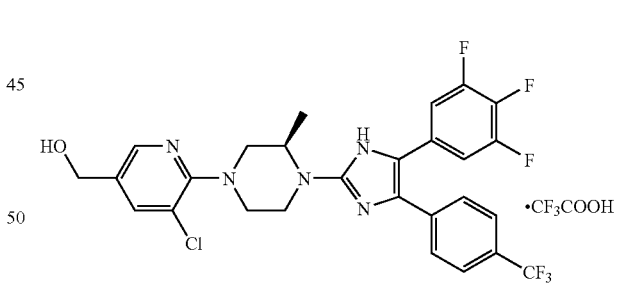

(c) (R)-(5-Chloro-6-(3-methyl-4-(4-(4-(trifluoromethyl)phenyl)-5-(3,4,5-trifluorophenyl)-1H-imidazol-2-yl)piperazin-1-yl)pyridin-3-yl)methanol 1-(4-(Trifluoromethyl)phenyl)-2-(3,4,5-trifluorophenyl)ethane-1,2-dione from step (b) above (190 mg, 0.57 mmol) reacted with (2R)-4-(3-chloro-5-(hydroxylmethyl)pyridin-2-yl)-2-methylpiperazine-1-carboxamidine dihydrochloride (160 mg, 0.45 mmol, Example 8(a)) under the conditions of Example 8(b). The crude product was purified by preparative HPLC [gradient 10-90% MeCN (0.1% TFA)/H₂O (0.1% TFA)] to give the title compound as a pale yellow amorphous solid. MS (ESI, pos. ion) m/z: 582 (M+1).

EXAMPLE 40

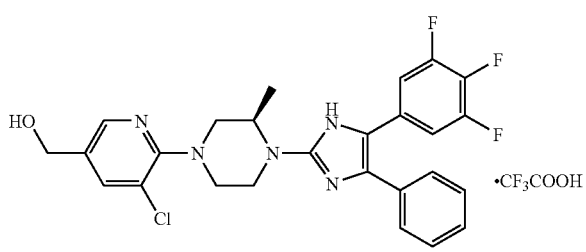

(R)-(5-Chloro-6-(3-methyl-4-(4-phenyl-5-(3,4,5-trifluorophenyl)-1H-imidazol-2-yl)piperazin-1-yl)pyridin-3-yl)methanol, trifluoroacetic acid salt 1-Phenyl-2-(3,4,5-trifluorophenyl)ethane-1,2-dione (60 mg, 0.23 mmol, Example 38(b)) was reacted with (2R)-4-(3-Chloro-5-(hydroxylmethyl)pyridin-2-yl)-2-methylpiperazine-1-carboxamidine dihydrochloride (84 mg, 0.24 mmol, Example 8(a)) under the conditions of Example 8(b). The crude product was purified by preparative HPLC [gradient 10-90% MeCN (0.1% TFA)/H$_2$O (0.1% TFA)] to give the title compound as a pale yellow amorphous solid. MS (ESI, pos. ion) m/z: 514

EXAMPLE 41

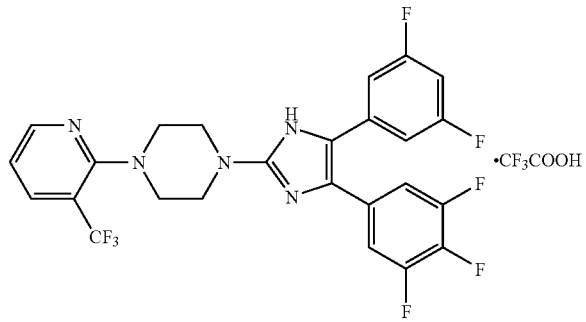

1-(5-(3,5-Difluorophenyl)-4-(3,4,5-trifluorophenyl)-H-imidazol-2-yl)-4-(3-(trifluoromethyl)pyridin-2-yl)piperazine, trifluoroacetic acid salt

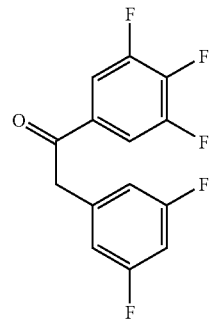

(a) 2-(3,5-Difluorophenyl)-1-(3,4,5-trifluorophenyl)ethanone

A solution of CuCN (0.685 g, 7.65 mmol, Aldrich) and LiBr (1.35 g, 15.57 mmol, Aldrich) in THF (8 mL) was cooled to −50° C. and to this was added (3,5-difluorobenzyl)zinc(II) bromide (2.00 g, 7.35 mmol, Rieke Metals) followed by 3,4,5-trifluorobenzoyl chloride (1.43 g, 7.35 mmol, Oakwood) and under the conditions of Example 7(a). The crude product was purified on silica gel using ISCO Combiflash® system with EtOAc/Hexanes (1:10) as the eluant to give the title compound as a yellow amorphous solid. MS (ESI, pos. ion) m/z: 287

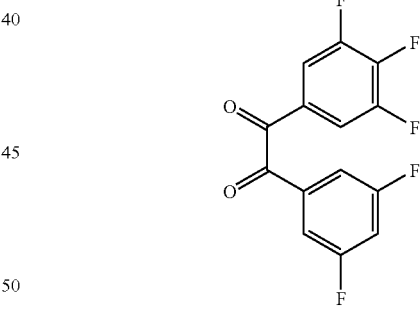

(b) 1-(3,5-Difluorophenyl)-2-(3,4,5-trifluorophenyl)ethane-1,2-dione

A solution of 2-(3,5-difluorophenyl)-1-(3,4,5-trifluorophenyl)ethanone from step (a) above (0.46 g, 1.61 mmol) and N-bromosuccimide (0.63 g, 3.6 mmol, Aldrich) in DMSO (8 mL) was reacted under the conditions of Example 7(b). The crude product was purified on silica gel using ISCO Combiflash® system with EtOAc/Hexanes (1:10) as the eluant to give the title compound as a yellow amorphous solid. MS (ESI, pos. ion) m/z: 301

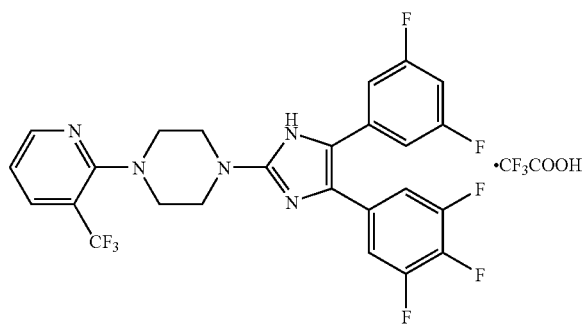

(c) 1-(5-(3,5-Difluorophenyl)-4-(3,4,5-trifluorophenyl)-1H-imidazol-2-yl)-4-(3-(trifluoromethyl)pyridin-2-yl)piperazine 1-(3,5-Difluorophenyl)-2-(3,4,5-trifluorophenyl)ethane-1,2-dione from step (b) above (117 mg, 0.39 mmol) reacted with 4-(3-(trifluoromethyl)pyridin-2-yl)piperazine-1-carboxamidine (100 mg, 0.37 mmol, Example 3(a)) under the conditions of Example 4(b). The crude product was purified by preparative HPLC [gradient 10-90% MeCN (0.1% TFA)/H$_2$O (0.1% TFA)] to give the title compound as an amorphous solid. MS (ESI, pos. ion) m/z: 540 (M+1)

EXAMPLE 42

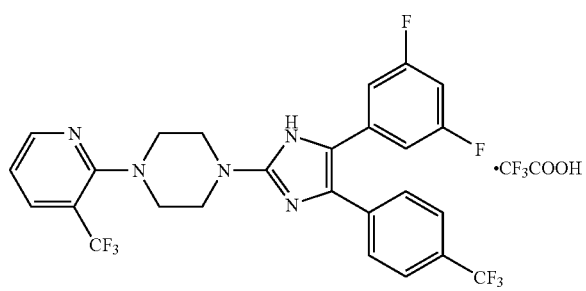

1-(5-(3,5-Difluorophenyl)-4-(4-(trifluoromethyl)phenyl)-1H-imidazol-2-yl)-4-(3-(trifluoromethyl)pyridin-2-yl)piperazine, trifluoroacetic acid salt

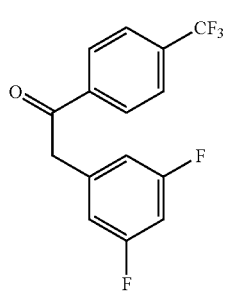

(a) 2-(3,5-Difluorophenyl)-1-(4-(trifluoromethyl)phenyl)ethanone

A solution of CuCN (0.335 g, 3.74 mmol, Aldrich) and LiBr (0.665 g, 7.66 mmol, Aldrich) in THF (5 mL) was cooled to −50° C. and to this was added (3,5-difluorobenzyl)zinc(II) bromide (1.01 g, 3.70 mmol, Rieke Metals) followed by 4-(trifluoromethyl)benzoyl chloride (0.632 g, 3.03 mmol, Aldrich) and under the conditions of Example 7(a). The crude product was purified on silica gel using ISCO Combiflash® system with EtOAc/Hexanes (1:10) as the eluant to give the title compound as a yellow amorphous solid. MS (ESI, pos. ion) m/z: 301

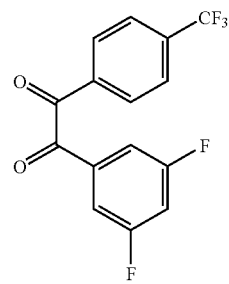

(b) 1-(3,5-Difluorophenyl)-2-(4-(trifluoromethyl)phenyl)ethane-1,2-dione

A solution of 2-(3,5-difluorophenyl)-1-(4-(trifluoromethyl)phenyl)ethanone from step (a) above (0.366 g, 1.22 mmol) and N-bromosuccimide (0.485 g, 2.73 mmol, Aldrich) in DMSO (8 mL) was reacted under the conditions of Example 7(b). The crude product was purified on silica gel using ISCO Combiflash® system with EtOAc/Hexanes (1:10) as the eluant to give the title compound as a yellow amorphous solid. MS (ESI, pos. ion) m/z: 315

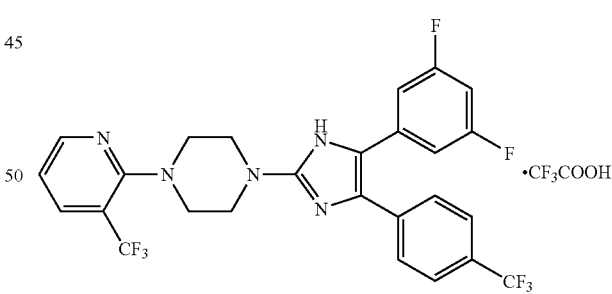

(c) 1-(5-(3,5-Difluorophenyl)-4-(4-(trifluoromethyl)phenyl)-1H-imidazol-2-yl)-4-(3-(trifluoromethyl)pyridin-2-yl)piperazine 1-(3,5-Difluorophenyl)-2-(4-(trifluoromethyl)phenyl)ethane-1,2-dione from step (b) above (120 mg, 0.38 mmol) reacted with 4-(3-(trifluoromethyl)pyridin-2-yl)piperazine-1-carboxamidine (100 mg, 0.37 mmol, Example 3(a)) under the conditions of Example 4(b). The crude product was purified by preparative HPLC [gradient 10-90% MeCN (0.1% TFA)/H$_2$O (0.1% TFA)] to give the title compound as an amorphous solid. MS (ESI, pos. ion) m/z: 554 (M+1)

EXAMPLE 43

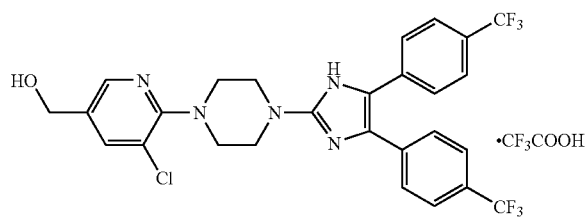

((6-(4-(4,5-Bis(4-(trifluoromethyl)phenyl)-1H-imidazol-2-yl)piperazin-1-yl)-5-chloropyridin-3-yl)methanol, trifluoroacetic acid salt 1,2-Bis(4-(trifluoromethyl)phenyl)ethane-1,2-dione (155 mg, 0.45 mmol, Example 7(b)) was reacted with (4-(3-chloro-5-(hydroxymethyl)pyridin-2-yl)piperazine-1-carboxamidine dihydrochloride (151 mg, 0.44 mmol, Example 9(a)) under the conditions of Example 8(b). The crude product was purified by preparative HPLC [gradient 10-90% MeCN (0.1% TFA)/H$_2$O (0.1% TFA)] to give the title compound as an off-white amorphous solid. MS (ESI, pos. ion) m/z: 582.

Biological Assays

Capsaicin-induced Ca$^{2+}$ influx in primary dorsal root ganglion neurons Embryonic 19 day old (E19) dorsal root ganglia (DRG) were dissected from timed-pregnant, terminally anesthetized Sprague-Dawley rats (Charles River, Wilmington, Mass.) and collected in ice-cold L-15 media (Life Technologies, Grand Island, N.Y.) containing 5% heat inactivated horse serum (Life Technologies). The DRG were then dissociated into single cell suspension using a papain dissociation system (Worthington Biochemical Corp., Freehold, N.J.). The dissociated cells were pelleted at 200×g for 5 min and re-suspended in EBSS containing 1 mg/ml ovomucoid inhibitor, 1 mg/ml ovalbumin and 0.005% DNase. Cell suspension was centrifuged through a gradient solution containing 10 mg/ml ovomucoid inhibitor, 10 mg/ml ovalbumin at 200×g for 6 min to remove cell debris; and filtered through a 88-μm nylon mesh (Fisher Scientific, Pittsburgh, Pa.) to remove any clumps. Cell number was determined with a hemocytometer and cells were seeded into poly-ornithine 100 μg/ml (Sigma) and mouse laminin 1 μg/ml (Life Technologies)-coated 96-well plates at 10×10$^3$ cells/well in complete medium. The complete medium consists of minimal essential medium (MEM) and Ham's F12, 1:1, penicillin (100 U/ml), and streptomycin (100 μg/ml), and nerve growth factor (10 ng/ml), 10% heat inactivated horse serum (Life Technologies). The cultures were kept at 37° C., 5% CO$_2$ and 100% humidity. For controlling the growth of non-neuronal cells, 5-fluoro-2'-deoxyuridine (75 μM) and uridine (180 μM) were included in the medium. Activation of VR1 is achieved in these cellular assays using either a capsaicin stimulus (ranging from 0.01-10 μM) or by an acid stimulus (addition of 30 mM Hepes/Mes buffered at pH 4.1). Compounds are also tested in an assay format to evaluate their agonist properties at VR1.

Capsaicin Antagonist Assay: E-19 DRG cells at 5 days in culture are incubated with serial concentrations of VR1 antagonists, in HBSS (Hanks buffered saline solution supplemented with BSA 0.1 mg/ml and 1 mM Hepes at pH 7.4) for 15 min, 37° C. Cells are then challenged with a VR1 agonist, capsaicin 200 nM, in activation buffer containing 0.1 mg/ml BSA, 15 mM Hepes, pH 7.4, and 10 μCi/ml $^{45}$Ca$^{2+}$ (Amersham) in Ham's F12 for 2 min at 37° C.

Acid Antagonist Assay: Compounds are pre-incubated with E-19 DRG cells for 2 minutes prior to addition of Calcium-45 in 30 mM Hepes/Mes buffer (Final Assay pH 5) and then left for an additional 2 minutes prior to compound washout. Final 45Ca (Amersham CES3-2mCi) at 10 μCi/mL.

Agonist Assay: Compounds are incubated with E-19 DRG cells for 2 minutes in the presence of Calcium-45 prior to compound washout. Final $^{45}$Ca$^{2+}$ (Amersham CES3-2mCi) at 10 μCi/mL.

Compound Washout and Analysis: Assay plates are washed using an ELX405 plate washer (Bio-Tek Instruments Inc.) immediately after functional assay. Wash 3× with PBS Mg2+/Ca2+ free, 0.1 mg/mL BSA. Aspirate between washes. Read plates using a MicroBeta Jet (Wallac Inc.). Compound activity is then calculated using appropriate computational algorithms.

$^{45}$Calcium$^{2+}$ Assay Protocol

Compounds may be assayed using Chinese Hamster Ovary cell lines stably expressing either human VR1 or rat VR1 under a CMV promoter. Cells can be cultured in Growth Medium, routinely passaged at 70% confluency using trypsin and plated in the assay plate 24 hours prior to compound evaluation.

Possible Growth Medium:
DMEM, high glucose (Gibco 11965-084).
10% Dialyzed serum (Hyclone SH30079.03).
1× Non-Essential Amino Acids (Gibco 11140-050).
1× Glutamine-Pen-Strep (Gibco 10378-016).
Geneticin, 450 μg/mL (Gibco 10131-035).

Compounds can be diluted in 100% DMSO and tested for activity over several log units of concentration [40 μM-2 pM]. Compounds may be further diluted in HBSS buffer (pH 7.4) 0.1 mg/mL BSA, prior to evaluation. Final DMSO concentration in assay would be 0.5%. Each assay plate can be controlled with a buffer only and a known antagonist compound (either capsazepine or one of the described VR1 antagonists).

Activation of VR1 can be achieved in these cellular assays using either a capsaicin stimulus (ranging from 0.1-1 μM) or by an acid stimulus (addition of 30 mM Hepes/Mes buffered at pH 4.1). Compounds may also tested in an assay format to evaluate their agonist properties at VR1.

Capsaicin Antagonist Assay: Compounds may be pre-incubated with cells (expressing either human or rat VR1) for 2 minutes prior to addition of Calcium-45 and Capsaicin and then left for an additional 2 minutes prior to compound washout. Capsaicin (0.5 nM) can be added in HAM's F12, 0.1 mg/mL BSA, 15 mM Hepes at pH 7.4. Final $^{45}$Ca (Amersham CES3-2mCi) at 10 μCi/mL.

Acid Antagonist Assay: Compounds can be pre-incubated with cells (expressing either human or rat VR1) for 2 minutes prior to addition of Calcium-45 in 30 mM Hepes/Mes buffer (Final Assay pH 5) and then left for an additional 2 minutes prior to compound washout. Final $^{45}$Ca (Amersham CES3-2mCi) at 10 μCi/mL.

Agonist Assay: Compounds can be incubated with cells (expressing either human or rat VR1) for 2 minutes in the presence of Calcium-45 prior to compound washout. Final $^{45}$Ca (Amersham CES3-2mCi) at 10 μCi/mL.

Compound Washout and Analysis: Assay plates can be washed using an ELX405 plate washer (Bio-Tek Instruments Inc.) immediately after functional assay. One can wash 3× with PBS $MG2^+/Ca^{2+}$ free, 0.1 mg/mL BSA, aspirating between washes. Plates may be read using a MicroBeta Jet (Wallac Inc.). Compound activity may then calculated using appropriate computational algorithms.

Useful nucleic acid sequences and proteins may be found in U.S. Pat. Nos. 6,335,180, 6,406,908 and 6,239,267, herein incorporated by reference in their entirety.

For the treatment of vanilloid-receptor-diseases, such as acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating vanilloid-receptor-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, isopropoxymethyl, α-methoxyethyl, groups such as α-(($C_1$-$C_4$) alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethylformamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound having the structure:

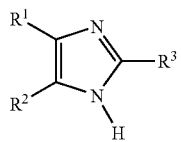

or any pharmaceutically-acceptable salt or hydrate thereof, wherein:

$R^1$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from $R^e$, halo, cyano, nitro, —C(=O)$R^b$, —C(=O)O$R^b$, —C(=O)NR$^a$R$^a$, —C(=NR$^a$)NR$^a$R$^a$, —OR$^a$, —OC(=O)$R^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)$R^b$, —S(=O)$_2$R$^b$, —S(=O)$_2$NR$^a$R$^a$, —S(=O)$_2$N(R$^a$)C(=O)$R^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)$R^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and the ring is additionally substituted by 0, 1, 2, 3, 4 or 5 substituents independently selected from Br, Cl, F and I;

$R^2$ is (A) a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from $R^e$, halo, cyano, nitro, —C(=O)$R^b$, —C(O)O$R^b$, —C(=O)NR$^a$R$^a$, —C(=NR$^a$)NR$^a$R$^a$, —OR$^a$, —OC(=O)$R^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, S(=O)$R^b$, —S(=O)$_2$R$^b$, —S(=O)$_2$NR$^a$R$^a$, —S(=O)$_2$ N(R$^a$)C(=O)$R^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)$R^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and the ring is additionally substituted by 0, 1, 2, 3, 4 or 5 substituents independently selected from Br, Cl, F and I; or $R^2$ is (B) $C_{1-6}$alkyl substituted by 1, 2 or 3 substituents independently selected from $C_{1-4}$haloalkyl, halo, oxo, cyano, nitro, —C(=O)$R^b$, —C(=O)O$R^b$, —C(=O)NR$^a$R$^a$, —C(=NR$^a$)NR$^a$R$^a$, —OR$^a$, —OC(=O)$R^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)$R^b$, —S(=O)$_2$R$^b$, —S(=O)$_2$NR$^a$R$^a$, —S(=O)$_2$N(R$^a$)C(=O)$R^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)$R^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by 0 or 1 saturated, partially saturated or unsaturated 5-, 6- or 7-membered monocyclic or 6-, 7-, 8-, 9-, 10- or 11-membered bicyclic rings containing 0, 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from $C_{1-8}$alkyl, $C_{1-4}$haloalkyl, halo, cyano, oxo, nitro, —C(=O)$R^b$, —C(=O)O$R^b$, —C(=O)NR$^a$R$^a$, —C(=NR$^a$)NR$^a$R$^a$, —OR$^a$, —OC(=O)$R^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)$R^b$, —S(=O)$_2$R$^b$, —S(=O)$_2$NR$^a$R$^a$, —S(=O)$_2$N(R$^a$)C(=O)$R^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)$R^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and the ring is additionally substituted by 0, 1, 2, 3, 4 or 5 substituents independently selected from Br, Cl, F and I; or $R^2$ is (C) halo, cyano, nitro, —(=O)$R^g$, —C(=O)$R^b$, —C(=O)O$R^b$, —C(=O)OR$^e$, —C(=O)OR$^g$, —C(=O)NR$^a$R$^a$, —C(=O)NR$^a$R$^e$, —C(=O)NR$^a$R$^g$, —C(=NR$^a$)NR$^a$R$^a$, —C(=NR$^a$)NR$^a$R$^e$, —C(=NR$^a$)NR$^a$R$^g$, —OR$^a$, —OR$^e$, —OR$^g$, —OC(=O)$R^b$, —OC(=O)R$^e$, —OC(=O)R$^g$, —OC(=O)NR$^a$R$^a$, —OC(=O)NR$^a$R$^e$, —OC(=O)NR$^a$R$^g$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)$R^b$, —S(=O)$_2$R$^b$, —S(=O)$_2$NR$^a$R$^a$, —S(=O)$_2$N(R$^a$)C(=O)$R^b$, —S(=O)$_2$N(R$^a$)C(=O)OR$^b$, —S(=O)$_2$N(R$^a$)C(=O)NR$^a$R$^a$, —NR$^a$R$^a$, NR$^a$R$^e$, NR$^a$R$^g$, —N(R$^a$)C(=O)$R^b$, —N(R$^a$)C(=O)R$^e$, —N(R$^a$)C(=O)OR$^b$, —N(R$^a$)C(=O)R$^g$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkyl-NR$^a$R$^a$ or —NR$^a$C$_{2-6}$alkylOR$^a$;

$R^3$ is selected from

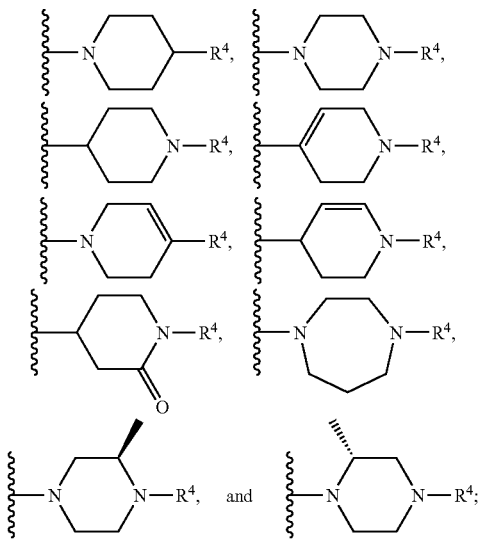

or $R^3$ is -J-$R^6$;

J is NH, N($C_{1-3}$alkyl), O, S(=O) or S(=O)$_2$;

$R^4$ is phenyl or naphthyl, wherein the phenyl and naphthyl are substituted by 1, 2, 3 or 4 substituents selected from $R^c$, $R^e$, halo, $C_{1-4}$haloalkyl, cyano, nitro, —C(=O)$R^e$, —C(=O)O$R^h$, —C(=O)N$R^aR^h$, —C(=N$R^a$)N$R^aR^h$, —O$R^h$, —OC(=O)$R^e$, —OC(=O)N$R^aR^h$, —OC(=O)N($R^a$)S(=O)$_2R^e$, —O$C_{2-6}$alkylN$R^aR^h$, —O$C_{2-6}$alkylO$R^h$, —S$R^e$, —S(=O)$R^e$, —S(=O)$_2R^e$, —S(=O)$_2$N$R^aR^h$, —S(=O)$_2$N($R^a$)C(=O)$R^e$, —S(=O)$_2$N($R^a$)C(=O)O$R^h$, —S(=O)$_2$N($R^a$)C(=O)N$R^aR^h$, —N$R^aR^h$, —N($R^a$)C(=O)$R^e$, —N($R^a$)C(=O)O$R^h$, —N($R^a$)C(=O)N$R^aR^h$, —N($R^a$)C(=N$R^a$)N$R^aR^h$, —N($R^a$)S(=O)$_2R^e$, —N($R^a$)S(=O)$_2$N$R^aR^h$, —N$R^aC_{2-6}$alkylN$R^aR^h$, —N$R^aC_{2-6}$alkylO$R^h$, —C(=O)$R^g$, —C(=O)O$R^g$, —C(=O)N$R^aR^g$, —C(=N$R^a$)N$R^aR^g$, —O$R^g$, —OC(=O)$R^g$, —OC(=O)N$R^aR^g$, —OC(=O)N($R^a$)S(=O)$_2R^g$, —OC(=O)N($R^g$)S(=O)$_2R^e$, —O$C_{2-6}$alkylN$R^aR^g$, —O$C_{2-6}$alkylO$R^g$, —S$R^g$, —S(=O)$R^g$, —S(=O)$_2R^g$, —S(=O)$_2$N$R^aR^g$, —S(=O)$_2$N($R^g$)C(=O)$R^e$, —S(=O)$_2$N($R^a$)C(=O)$R^g$, —S(=O)$_2$N($R^g$)C(=O)O$R^h$, —S(=O)$_2$N($R^a$)C(=O)O$R^g$, —S(=O)$_2$N($R^g$)C(=O)N$R^aR^h$, —S(=O)$_2$N($R^a$)C(=O)N$R^aR^g$, —N$R^aR^g$, —N($R^g$)C(=O)$R^e$, —N($R^a$)C(=O)$R^g$, —N($R^g$)C(=O)O$R^h$, —N($R^a$)C(=O)O$R^g$, —N($R^g$)C(=O)N$R^aR^h$, —N($R^a$)C(=O)N$R^aR^g$, —N($R^g$)C(=N$R^a$)N$R^aR^h$, —N($R^a$)C(=N$R^a$)N$R^aR^g$, —N($R^g$)S(=O)$_2R^e$, —N($R^a$)S(=O)$_2R^g$, —N($R^g$)S(=O)$_2$N$R^aR^h$, —N($R^a$)S(=O)$_2$N$R^aR^g$, —N$R^hC_{2-6}$alkylN$R^aR^g$, —N$R^aC_{2-6}$alkylN$R^aR^g$, —N$R^gC_{2-6}$alkylO$R^h$ and —N$R^aC_{2-6}$alkylO$R^g$; or $R^4$ is $R^c$ substituted by 1, 2, 3 or 4 substituents selected from $R^c$, $R^e$, halo, $C_{1-4}$haloalkyl, cyano, nitro, —C(=O)$R^e$, —C(=O)O$R^h$, —C(=O)N$R^aR^h$, —C(=N$R^a$)N$R^aR^h$, —O$R^h$, —OC(=O)$R^e$, —OC(=O)N$R^aR^h$, —OC(=O)N($R^a$)S(=O)$_2R^e$, —O$C_{2-6}$alkylN$R^aR^h$, —O$C_{2-6}$alkylO$R^h$, —S$R^e$, —S(=O)$R^e$, —S(=O)$_2R^e$, —S(=O)$_2$N$R^aR^h$, —S(=O)$_2$N($R^a$)C(=O)$R^e$, —S(=O)$_2$N($R^a$)C(=O)O$R^h$, —S(=O)$_2$N($R^a$)C(=O)N$R^aR^h$, —N$R^aR^h$, —N($R^a$)C(=O)$R^e$, —N($R^a$)C(=O)O$R^h$, —N($R^a$)C(=O)N$R^aR^h$, —N($R^a$)C(=N$R^a$)N$R^aR^h$, —N($R^a$)S(=O)$_2R^e$, —N($R^a$)S(=O)$_2$N$R^aR^h$, —N$R^aC_{2-6}$alkylN$R^aR^h$, —N$R^aC_{2-6}$alkylO$R^h$, —C(=O)$R^g$, —C(=O)O$R^g$, —C(=O)N$R^aR^g$, —O$R^g$, —OC(=O)$R^g$, —OC(=O)N$R^aR^g$, —OC(=O)N($R^g$)S(=O)$_2R^e$, —O$C_{2-6}$alkylN$R^aR^g$, —O$C_{2-6}$alkylO$R^g$, —S$R^g$, —S(=O)$R^g$, —S(=O)$_2R^g$, —S(=O)$_2$N$R^aR^g$, —S(=O)$_2$N($R^g$)C(=O)$R^e$, —S(=O)$_2$N($R^a$)C(=O)$R^g$, —S(=O)$_2$N($R^g$)C(=O)O$R^h$, —S(=O)$_2$N($R^a$)C(=O)O$R^g$, —S(=O)$_2$N($R^g$)C(=O)N$R^aR^h$, —S(=O)$_2$N($R^a$)C(=O)N$R^aR^g$, —N$R^aR^g$, —N($R^g$)C(=O)$R^e$, —N($R^a$)C(=O)$R^g$, —N($R^g$)C(=O)O$R^h$, —N($R^a$)C(=O)O$R^g$, —N($R^g$)C(=O)N$R^aR^h$, —N($R^a$)C(=O)N$R^aR^g$, —N($R^g$)C(=N$R^a$)N$R^aR^h$, —N($R^a$)C(=N$R^a$)N$R^aR^g$, —N($R^g$)S(=O)$_2R^e$, —N($R^a$)S(=O)$_2R^g$, —N($R^g$)S(=O)$_2$N$R^aR^h$, —N($R^a$)S(=O)$_2$N$R^aR^g$, —N$R^hC_{2-6}$alkylN$R^aR^g$, —N$R^aC_{2-6}$alkylN$R^aR^g$, —N$R^gC_{2-6}$alkylO$R^h$ and —N$R^aC_{2-6}$alkylO$R^g$, wherein $R^4$ is not imidazole or any sustituted derivative thereof;

$R^5$ is, independently, in each instance, H, $C_{1-8}$alkyl, $C_{1-4}$haloalkyl, —O($C_{1-7}$alkyl), —N($C_{1-7}$alkyl)$R^a$, or a $C_{1-6}$alkyl substituted by 1, 2 or 3 substituents selected from halo, cyano, —O$R^a$, —OC(=O)$R^b$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N$R^aC_{2-6}$alkylN$R^aR^a$ and —N$R^aC_{2-6}$alkylO$R^a$; wherein any two geminal $R^5$ groups may additionally be oxo;

$R^{5'}$ is, independently, in each instance, H, $C_{1-8}$alkyl, $C_{1-4}$haloalkyl, —O($C_{1-7}$alkyl), —N($C_{1-7}$alkyl)$R^a$, or a $C_{1-6}$alkyl substituted by 1, 2 or 3 substituents selected from halo, cyano, —O$R^a$, —OC(=O)$R^b$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N$R^aC_{2-6}$alkylN$R^aR^a$ and —N$R^aC_{2-6}$alkylO$R^a$; wherein any two geminal $R^{5'}$ groups may additionally be oxo;

$R^6$ is phenyl vicinally fused with a 5-, 6- or 7-membered saturated, partially-saturated or unsaturated ring containing 0, 1, 2 or 3 heteroatoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$, and the ring is additionally substituted by 0, 1, 2, 3, 4 or 5 substituents independently selected from Br, Cl, F and I;

$R^a$ is independently, at each instance, H or $R^b$;

$R^b$ is independently, at each instance, phenyl, benzyl or $C_{1-6}$alkyl, the phenyl, benzyl and $C_{1-6}$alkyl being substituted by 0, 1, 2 or 3 substituents selected from halo, $C_{1-4}$alkyl, $C_{1-3}$haloalkyl, —O$C_{1-4}$alkyl, —NH$_2$, —NH$C_{1-4}$alkyl, and —N($C_{1-4}$alkyl)$C_{1-4}$alkyl;

$R^c$ is independently at each instance a saturated, partially saturated or unsaturated 5-, 6- or 7-membered monocyclic or 6-, 7-, 8-, 9-, 10- or 11-membered bicyclic ring containing 1, 2, 3 or 4 atoms selected from N, O and S, wherein the carbon atoms of the ring are substituted by 0, 1 or 2 oxo groups;

$R^d$ is independently at each instance $C_{1-8}$alkyl, $C_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

$R^e$ is independently at each instance $C_{1-6}$alkyl substituted by 0, 1, 2 or 3 substituents independently selected from $R^d$ and additionally substituted by 0 or 1 substituents selected from $R^g$;

$R^g$ is independently at each instance a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; and $R^h$ is independently at each instance $R^e$ or H.

2. A compound according to claim 1, wherein $R^3$ selected from

3. The compound according to claim 1, wherein $R^3$ is -J-R$^6$.

4. The compound selected from:
(2R)-1-(4,5-bis(4-(methyloxy)phenyl)-1H-imidazol-2-yl)-2-methyl-4-(3-(trifluoromethyl)-2-pyridinyl)piperazine;
(2R)-1-(4,5-bis(4-(trifluoromethyl)phenyl)-1H-imidazol-2-yl)-2-methyl-4-(3-(trifluoromethyl)-2-pyridinyl)piperazine;
(2R)-2-methyl-1-(5-phenyl-4-(4-(trifluoromethyl)phenyl)-1H-imidazol-2-yl)-4-(3-(trifluoromethyl)-2-pyridinyl)piperazine;
(2R)-4-(3-chloro-2-pyridinyl)-1-(4-(3,4-difluorophenyl)-5-(4-(trifluoromethyl)phenyl)-1H-imidazol-2-yl)-2-methylpiperazine;
(2S)-8-((4-phenyl-5-(4-(trifluoromethyl)phenyl)-1H-imidazol-2-yl)amino)-1,2,3,4-tetrahydro-2-naphthalenol;
(4-(4,5-bis(4-(trifluoromethyl)phenyl)-1H-imidazol-2-yl)-3'-chloro-3,6-dihydro-2H-1,2'-bipyridin-5'-yl)methanol;
(5-chloro-6-((3R)-3-methyl-4-(5-(4-(trifluoromethyl)phenyl)-4-(3,4,5-trifluorophenyl)-1H-imidazol-2-yl)-1-piperazinyl)-3-pyridinyl)methanol;
(5-chloro-6-((3R)-3-methyl-4-(5-phenyl-4-(3,4,5-trifluorophenyl)-1H-imidazol-2-yl)-1-piperazinyl)-3-pyridinyl)methanol;
(5-chloro-6-((3R)-3-methyl-4-(5-phenyl-4-(4-(trifluoromethyl)phenyl)-1H-imidazol-2-yl)-1-piperazinyl)-3-pyridinyl)methanol;
(5-chloro-6-((3R)-4-(4-(3,4-difluorophenyl)-5-(4-(trifluoromethyl)phenyl)-1H-imidazol-2-yl)-3-methyl-1-piperazinyl)-3-pyridinyl)methanol;
(5-chloro-6-(4-(5-phenyl-4-(4-(trifluoromethyl)phenyl)-1H-imidazol-2-yl)-1-piperazinyl)-3-pyridinyl)methanol;
(6-((3R)-4-(4,5-bis(4-(methyloxy)phenyl)-1H-imidazol-2-yl)-3-methyl-1-piperazinyl)-5-chloro-3-pyridinyl)methanol;
(6-((3R)-4-(4,5-bis(4-(trifluoromethyl)phenyl)-1H-imidazol-2-yl)-3-methyl-1-piperazinyl)-5-chloro-3-pyridinyl)methanol;
(6-((3 R)-4-(4,5-bis(4-(trifluoromethyl)phenyl)-1H-imidazol-2-yl)-3-methyl-1-piperazinyl)-3-pyridinyl)methanol;
(6-(4-(4,5-bis(4-(trifluoromethyl)phenyl)-1H-imidazol-2-yl)-1-piperazinyl)-5-chloro-3-pyridinyl)methanol;
(6-(4-(5-phenyl-4-(4-(trifluoromethyl)phenyl)-1H-imidazol-2-yl)-1-piperazinyl)-3-pyridinyl)methanol;
1-(1-methylethyl)-4-((4-(4-(trifluoromethyl)phenyl)-2-(4-(3-(trifluoromethyl)-2-pyridinyl)-1-piperazinyl)-1H-imidazol-5-yl)carbonyl)piperazine;
1-(3-chloro-2-pyridinyl)-4-(5-(4-(trifluoromethyl)phenyl)-4-(3,4,5-trifluorophenyl)-1H-imidazol-2-yl)piperazine;
1-(4-(3,5-difluorophenyl)-5-(3,4,5-trifluorophenyl)-1H-imidazol-2-yl)-4-(3-(trifluoromethyl)-2-pyridinyl)piperazine;
1-(4-(3,5-difluorophenyl)-5-(4-(trifluoromethyl)phenyl)-1H-imidazol-2-yl)-4-(3-(trifluoromethyl)-2-pyridinyl)piperazine;
1-(4-(4-(trifluoromethyl)phenyl)-5-(3,4,5-trifluorophenyl)-1H-imidazol-2-yl)-4-(3-(trifluoromethyl)-2-pyridinyl)piperazine;
1-(4,5-bis(3,4,5-trifluorophenyl)-1H-imidazol-2-yl)-4-(3-(trifluoromethyl)-2-pyridinyl)piperazine;
1-(4,5-bis(4-(trifluoromethyl)phenyl)-1H-imidazol-2-yl)-4-(3-(trifluoromethyl)-2-pyridinyl)piperazine;

1-(4,5-bis(4-fluorophenyl)-1H-imidazol-2-yl)-4-(3-(trifluoromethyl)-2-pyridinyl)piperazine;
1-(4,5-diphenyl-1H-imidazol-2-yl)-4-(3-(trifluoromethyl)-2-pyridinyl)piperazine;
1-(5-chloro-4-(4-(trifluoromethyl)phenyl)-1H-imidazol-2-yl)-4-(3-(trifluoromethyl)-2-pyridinyl)piperazine;
1-(5-phenyl-4-(3-(trifluoromethyl)phenyl)-1H-imidazol-2-yl)-4-(3-(trifluoromethyl)-2-pyridinyl)piperazine;
1-(5-phenyl-4-(3,4,5-trifluorophenyl)-1H-imidazol-2-yl)-4-(3-(trifluoromethyl)-2-pyridinyl)piperazine;
1-(5-phenyl-4-(4-(trifluoromethyl)phenyl)-1H-imidazol-2-yl)-4-(3-(trifluoromethyl)-2-pyridinyl)piperazine;
1,1-dimethylethyl 4-(2-(3'-(trifluoromethyl)-3,6-dihydro-2H-1,2'-bipyridin-4-yl)-4-(4-(trifluoromethyl)phenyl)-1H-imidazol-5-yl)-3,6-dihydro-1(2H)-pyridinecarboxylate;
2-(4-(4,5-bis(4-(trifluoromethyl)phenyl)-1H-imidazol-2-yl)-1-piperidinyl)-3-(trifluoromethyl)pyridine;
4-(4-(trifluoromethyl)phenyl)-2-(4-(3-(trifluoromethyl)-2-pyridinyl)-1-piperazinyl)-N-(3,4,5-trifluorophenyl)-1H-imidazole-5-carboxamide;
4-(4,5-bis(4-(trifluoromethyl)phenyl)-1H-imidazol-2-yl)-3'-(trifluoromethyl)-3,6-dihydro-2H-1,2'-bipyridine;
4-(4-chloro-5-(4-fluorophenyl)-1H-imidazol-2-yl)-3'-(trifluoromethyl)-3,6-dihydro-2H-1,2'-bipyridine;
4-(5-(1,2,3,6-tetrahydro-4-pyridinyl)-4-(4-(trifluoromethyl)phenyl)-1H-imidazol-2-yl)-3'-(trifluoromethyl)-3,6-dihydro-2H-1,2'-bipyridine;
4-(5-chloro-4-(4-(trifluoromethyl)phenyl)-1H-imidazol-2-yl)-3'-(trifluoromethyl)-3,6-dihydro-2H-1,2'-bipyridine;
8-((5-phenyl-4-(4-(trifluoromethyl)phenyl)-1H-imidazol-2-yl)amino)-2-naphthalenol;
methyl 5-(4-(trifluoromethyl)phenyl)-2-(4-(3-(trifluoromethyl)-2-pyridinyl)-1-piperazinyl)-1H-imidazole-4-carboxylate;
N-((1-(2-methylpropyl)-2-piperidinyl)methyl)-4-(4-(trifluoromethyl)phenyl)-2-(4-(3-(trifluoromethyl)-2-pyridinyl)-1-piperazinyl)-1H-imidazole-5-carboxamide;
N-((1-ethyl-2-pyrrolidinyl)methyl)-4-(4-(trifluoromethyl)phenyl)-2-(4-(3-(trifluoromethyl)-2-pyridinyl)-1-piperazinyl)-1H-imidazole-5-carboxamide;
N-(2-piperidinylmethyl)-4-(4-(trifluoromethyl)phenyl)-2-(4-(3-(trifluoromethyl)-2-pyridinyl)-1-piperazinyl)-1H-imidazole-5-carboxamide; and
N-(5-phenyl-4-(4-(trifluoromethyl)phenyl)-1H-imidazol-2-yl)-5-isoquinolinamine; or a pharmaceutically-acceptable salt or hydrate thereof.

5. A pharmaceutical composition comprising a compound according to claim 1 and a pharmaceutically-acceptable diluent or carrier.

6. A compound according to claim 2, wherein
$R^4$ is a ring selected from thiophene, pyrrole, 1,3-oxazole, 1,3-thiazole, 1,3,4-oxadiazole, 1,3,4-thiadiazole, 1,2,3-oxadiazole, 1,2,3-thiadiazole, 1H-1,2,3-triazole, isothiazole, 1,2,4-oxadiazole, 1,2,4-thiadiazole, 1,2,3,4-oxatriazole, 1,2,3,4-thiatriazole, 1H-1,2,3,4-tetraazole, 1,2,3,5-oxatriazole, 1,2,3,5-thiatriazole, furan, 1,2,4-triazol-4-yl, 1,2,4-triazol-5-yl, isoxazol-3-yl, isoxazol-5-yl, thiolane, pyrrolidine, tetrahydrofuran, 4,5-dihydrothiophene, 2-pyrroline, 4,5-dihydrofuran, pyridazine, pyrimidine, pyrazine, 1,2,3-triazine, 1,2,4-triazine, 1,2,4-triazine, 1,3,5-triazine, pyridine, 2H-3,4,5,6-tetrahydropyran, thiane, 1,2-diazaperhydroine, 1,3-diazaperhydroine, piperazine, 1,3-oxazaperhydroine, morpholine, 1,3-thiazaperhydroine, 1,4-thiazaperhydroine, piperidine, 2H-3,4-dihydropyran, 2,3-dihydro-4H-thiin, 1,4,5,6-tetrahydropyridine, 2H-5,6-dihydropyran, 2,3-dihydro-6H-thiin, 1,2,5,6-tetrahydropyridine, 3,4,5,6-tetrahydropyridine, 4H-pyran, 4H-thiin, 1,4-dihydropyridine, 1,4-dithiane, 1,4-dioxane, 1,4-oxathiane, 1,2-oxazolidine, 1,2-thiazolidine, pyrazolidine, 1,3-oxazolidine, 1,3-thiazolidine, 1,2,4-oxadiazolidine, 1,3,4-oxadiazolidine, 1,2,4-thiadiazolidine, 1,3,4-thiadiazolidine, 1,2,4-triazolidine, 2-pyrazoline, 2,3-dihydroisothiazole, 4,5-dihydroisoxazole, 4,5-dihydroisothiazole, 2,5-dihydroisoxazole, 2,5-dihydroisothiazole, 2,3-dihydroisoxazole, 4,5-dihydrooxazole, 2,3-dihydrooxazole, 2,5-dihydrooxazole, 4,5-dihydrothiazole, 2,3-dihydrothiazole, 2,5-dihydrothiazole, 1,3,4-oxathiazolidine, 1,4,2-oxathiazolidine, 2,3-dihydro-1H-[1,2,3]triazole, 2,5-dihydro-1H-[1,2,3]triazole, 4,5-dihydro-1H-[1,2,3]triazole, 2,3-dihydro-1H-[1,2,4]triazole, 4,5-dihydro-1H-[1,2,4]triazole, 2,3-dihydro-[1,2,4]oxadiazole, 2,5-dihydro-[1,2,4]oxadiazole, 4,5-dihydro-[1,2,4]thiadiazole, 2,3-dihydro-[1,2,4]thiadiazole, 2,5-dihydro-[1,2,4]thiadiazole, 4,5-dihydro-[1,2,4]thiadiazole, 2,5-dihydro-[1,2,4]oxadiazole, 2,3-dihydro-[1,2,4]oxadiazole, 4,5-dihydro-[1,2,4]oxadiazole, 2,5-dihydro-[1,2,4]thiadiazole, 2,3-dihydro-[1,2,4]thiadiazole, 4,5-dihydro-[1,2,4]thiadiazole, 2,3-dihydro-[1,3,4]oxadiazole, 2,3-dihydro-[1,3,4]thiadiazole, [1,4,2]oxathiazole, [1,3,4]oxathiazole, 1,3,5-triazaperhydroine, 1,2,4-triazaperhydroine, 1,4,2-dithiazaperhydroine, 1,4,2-dioxazaperhydroine, 1,3,5-oxadiazaperhydroine, 1,2,5-oxadiazaperhydroine, 1,3,4-thiadiazaperhydroine, 1,3,5-thiadiazaperhydroine, 1,2,5-thiadiazaperhydroine, 1,3,4-oxadiazaperhydroine, 1,4,3-oxathiazaperhydroine, 1,4,2-oxathiazaperhydroine, 1,4,5,6-tetrahydropyridazine, 1,2,3,4-tetrahydropyridazine, 1,2,3,6-tetrahydropyridazine, 1,2,5,6-tetrahydropyrimidine, 1,2,3,4-tetrahydropyrimidine, 1,4,5,6-tetrahydropyrimidine, 1,2,3,6-tetrahydropyrazine, 1,2,3,4-tetrahydropyrazine, 5,6-dihydro-4H-[1,2]oxazine, 5,6-dihydro-2H-[1,2]oxazine, 3,6-dihydro-2H-[1,2]oxazine, 3,4-dihydro-2H-[1,2]oxazine, 5,6-dihydro-4H-[1,2]thiazine, 5,6-dihydro-2H-[1,2]thiazine, 3,6-dihydro-2H-[1,2]thiazine, 3,4-dihydro-2H-[1,2]thiazine, 5,6-dihydro-2H-[1,3]oxazine, 5,6-dihydro-4H-[1,3]oxazine, 3,6-dihydro-2H-[1,3]oxazine, 3,4-dihydro-2H-[1,3]oxazine, 3,6-dihydro-2H-[1,4]oxazine, 3,4-dihydro-2H-[1,4]oxazine, 5,6-dihydro-2H-[1,3]thiazine, 5,6-dihydro-4H-[1,3]thiazine, 3,6-dihydro-2H-[1,3]thiazine, 3,4-dihydro-2H-[1,3]thiazine, 3,6-dihydro-2H1-[1,4]thiazine, 3,4-dihydro-2H-[1,4]thiazine, 1,2,3,6-tetrahydro-[1,2,4]triazine, 1,2,3,4-tetrahydro-[1,2,4]triazine, 1,2,3,4-tetrahydro-[1,3,5]triazine, 2,3,4,5-tetrahydro-[1,2,4]triazine, 1,4,5,6-tetrahydro-[1,2,4]triazine, 5,6-dihydro-[1,4,2]dioxazine, 5,6-dihydro-[1,4,2]dioxazine, 5,6-dihydro-[1,4,2]dithiazine, 2,3-dihydro-[1,4,2]dioxazine, 3,4-dihydro-2H-[1,3,4]oxadiazine, 3,6-dihydro-2H-[1,3,4]oxadiazine, 3,4-dihydro-2H-[1,3,5]oxadiazine, 3,6-dihydro-2H-[1,3,5]oxadiazine, 5,6-dihydro-2H-[1,2,5]oxadiazine, 5,6-dihydro-4H-[1,2,5]oxadiazine, 3,4-dihydro-2H-[1,3,4]thiadiazine, 3,6-dihydro-2H-[1,3,4]thiadiazine, 3,4-dihydro-2H-[1,3,5]thiadiazine, 3,6-dihydro-2H-[1,3,5]thiadiazine, 5,6-dihydro-2H-[1,2,5]thiadiazine, 5,6-dihydro-4H-[1,2,5]thiadiazine, 5,6-dihydro-2H-[1,2,3]oxadiazine, 3,6-dihydro-2H-[1,2,5]oxadiazine, 5,6-dihydro-4H-[1,3,4]oxadiazine, 3,4-dihydro-2H-[1,2,5]oxadiazine, 5,6- dihydro-2H-[1,2,3]thiadiazine, 3,6-dihydro-2H-[1,2,5]thiadiazine, 5,6-dihydro-4H-[1,3,4]thiadiazine, 3,4-dihydro-2H-[1,2,5]thiadiazine, 5,6-dihydro-[1,4,3]oxathiazine, 5,6-dihydro-[1,4,2]oxathiazine, 2,3-dihydro-[1,4,3]oxathiazine, 2,3-dihydro-[1,4,2]oxathiazine, 4,5-dihydropyridine, 1,6-dihydropyridine, 5,6-dihydropyridine, 2H-pyran, 2H-thiin, 3,6-dihydropyridine, 2,3-dihydropyridazine, 2,5-dihydropyridazine, 4,5-dihydropyridazine, 1,2-dihydropyridazine, 2,3-dihydropyrimidine, 2,5-dihydropyrimidine, 5,6-dihydropyrimidine, 3,6-dihydropyrimidine, 4,5-dihydropyrazine, 5,6-dihydropyrazine, 3,6-dihydropyrazine, 4,5-dihydropyrazine, 1,4-dihydropyrazine, 1,4-dithiin, 1,4-dioxin, 2H-1,2-oxazine, 6H-1,2-oxazine, 4H-1,2-oxazine, 2H-1,3-oxazine, 4H-1,3-oxazine, 6H-1,3-oxazine, 2H-1,4-oxazine, 4H-1,4-oxazine, 2H-1,3-thiazine, 2H-1,4-thiazine, 4H-1,2-thiazine, 6H-1,3-thiazine, 4H-1,4-thiazine, 2H-1,2-thiazine, 6H-1,2-thiazine, 1,4-oxathiin, 2H, 5H-1,2,3-triazine, 1H,4H-1,2,3-triazine, 4,5-dihydro-1,2,3-triazine, 1H, 6H-1,2,3-triazine, 1,2-dihydro-1,2,3-triazine, 2,3-dihydro-1,2,4-triazine, 3H, 6H-1,2,4-triazine, 1H, 6H-1,2,4-triazine, 3,4-dihydro-1,2,4-triazine, 1H,4H-1,2,4-triazine, 5,6-dihydro-1,2,4-triazine, 4,5-dihydro-1,2,4-triazine, 2H,5H-1,2,4-triazine, 1,2-dihydro-1,2,4-triazine, 1H, 4H-1,3,5-triazine, 1,2-dihydro-1,3,5-triazine, 1,4,2-dithiazine, 1,4,2-dioxazine, 2H-1,3,4-oxadiazine, 2H-1,3,5-oxadiazine, 6H-1,2,5-oxadiazine, 4l-1-1,3,4-oxadiazine, 4H-1,3,5-oxadiazine, 4H-1,2,5-oxadiazine, 2H-1,3,5-thiadiazine, 6H-1,2,5-thiadiazine, 4H-1,3,4-thiadiazine, 4H-1,3,5-thiadiazine, 4H-1,2,5-thiadiazine, 2H-1,3,4-thiadiazine, 6H-1,3,4-thiadiazine, 6H-1,3,4-oxadiazine, 1,4,2-oxathiazine and any bicyclic derivative of any of the above rings containing a vicinally-fused phenyl, pyridine or pyrimidine, wherein the carbon atoms of the ring and bicyclic derivative are substituted by 0, 1 or 2 oxo or thioxo groups; wherein the ring or bicyclic derivative there of is substituted by 1, 2, 3 or 4 substituents selected from $R^c$, $R^e$, halo, $C_{1-4}$haloalkyl, cyano, nitro, —C(=O)$R^e$, —C(=O)O$R^h$, —C(=O)N$R^aR^h$, —C(=N$R^a$)N$R^aR^h$, —O$R^h$, —OC(=O)$R^e$, —OC(=O)N$R^aR^h$, —OC(=O)N($R^a$)S(=O)2$R^e$, —OC$_{2-6}$alkylN$R^aR^h$, —OC$_{2-6}$alkylO$R^h$, —S$R^e$, —S(=O)$R^e$, —S(=O)$_2R^e$, —S(=O)$_2$N$R^aR^h$, —S(=O)2N($R^a$)C(=O)$R^e$, —S(=O)$_2$N($R^a$)C(=O)O$R^h$, —S(=O)$_2$N($R^a$)C(=O)N$R^aR^h$, —N$R^aR^h$, —N($R^a$)C(=O)$R^e$, —N($R^a$)C(=O)O$R^h$, —N($R^a$)C(=O)N$R^aR^h$, —N($R^a$)C(=N$R^a$)N$R^aR^h$, —N($R^a$)S(=O)2$R^e$, —N($R^a$)S(=O)2N$R^aR^h$, —NR C$_{2-6}$alkylN$R^aR^h$, —N$R^aC_{2-6}$alkylO$R^h$, —C(=O)$R^g$, —C(=O)O$R^g$, —C(=O)N$R^aR^g$, —C(=N$R^a$)N$R^aR^g$, —O$R^g$, —OC(=O)$R^g$, —OC(=O)N$R^aR^g$, —OC(=O)N($R^a$)S(=O)$_2R^g$, —OC(=O)N($R^g$)S(=O)$_2R^e$, —OC$_{2-6}$lkylN$R^aR^g$, —OC$_{2-6}$alkylO$R^g$, —S$R^g$, —S(=O)$R^g$, —S(=O)$_2R^g$, —S(=O)$_2$N$R^aR^g$, —S(=O)$_2$N($R^g$)C(=O)$R^e$, —S(=O)$_2$N($R^a$)C(=O)$R^g$, —S(=O)$_2$N($R^g$)C(=O)O$R^h$, —(=O)$_2$N($R^a$)C(=O)O$R^g$, —S(=O)$_2$N($R^g$)C(=O)N$R^aR^h$, —S(=O)$_2$N($R^a$)C(=O)N$R^aR^g$, —N$R^aR^g$, —N($R^g$)C(=O)$R^e$, —N($R^a$)C(=O)$R^g$, —N($R^g$)C(=O)O$R^h$, —N($R^a$)C(=O)O$R^g$, —N($R^g$)C (=O)N$R^aR^h$, —N($R^a$)C(=O)N$R^aR^g$, —N($R^g$)C (=N$R^a$)N$R^aR^h$, —N($R^a$)C(=N$R^a$)N$R^aR^g$, —N($R^g$)S (=O)$_2R^e$, —N($R^a$)S(=O)$_2R^g$, —N($R^g$)S(=O)$_2$N$R^aR^h$, —N($R^a$)S(=O)$_2$N$R^aR^g$, —NR$^h$C$_{2-6}$alkylN$R^aR^g$, —NR$^aC_{2-6}$alkylN$R^aR^g$, —NR$^gC_{2-6}$alkylO$R^h$ and —NR$^aC_{2-6}$alkylO$R^g$.

7. A compound according to claim 2, wherein $R^c$ is independently at each instance a unsaturated 6-monocyclic ring containing 1 or 2 N atoms.

8. A compound according to claim 2, wherein $R^c$ is pyridinyl.

9. A compound according to claim 2, wherein
$R^4$ is pyridine substituted by 1, 2, 3 or 4 substituents selected from $R^c$, $R^e$, halo, $C_{1-4}$haloalkyl, cyano, nitro, —C(=O)$R^e$, —C(=O)O$R^h$, —C(=O)N$R^aR^h$, —C(N$R^a$)N$R^aR^h$, —O$R^h$, —OC(=O)$R^e$, —OC(=O) N$R^aR^h$, —OC(=O)N($R^a$)S(=O)2$R^e$, —OC$_{2-6}$alkylN$R^aR^h$, —OC$_{2-6}$alkylO$R^h$, —S$R^e$, —S(=O)$R^e$, —S(=O)$_2R^e$, —S(=O)$_2$N$R^aR^h$, —S(=O)$_2$N($R^a$)C (=O)$R^e$, —S(=O)$_2$N($R^a$)C(=O)O$R^h$, —S(=O)$_2$N ($R^a$)C(=O)N$R^aR^h$, —N$R^aR^h$, —N($R^a$)C(=O)$R^e$, —N($R^a$)C(=O)O$R^h$, N($R^a$)C(=O)N$R^aR^h$, —N($R^a$)C (=N$R^a$)N$R^aR^h$, —N($R^a$)S(=O)$_2R^e$, —N($R^a$)S(=O)$_2$ N$R^aR^h$, —NR$^aC_{2-6}$alkylN$R^aR^h$, —NR$^aC_{2-6}$alkylO$R^h$, —C(=O)$R^g$, —C(=O)O$R^g$, —C(=O)N$R^aR^g$, —C(=N$R^a$)N$R^aR^g$, —O$R^g$, —OC(=O)$R^g$, —OC (=O)N$R^aR^g$, —OC(=O)N($R^a$)S(=O)$_2R^g$, —OC (=O)N($R^g$)S(=O)$_2R^e$, —OC$_{2-6}$alkylN$R^aR^g$, —OC$_{2-6}$alkylO$R^g$, —S$R^g$, —S(=O)$R^g$, —S(=O)$R^g$, —S(=O)$_2$ N$R^aR^g$, —S(=O)$_2$N($R^g$)C(=O)$R^e$, —S(=O)$_2$N($R^a$)C(=O)$R^g$, —S(=O)$_2$N($R^g$)C(=O) O$R^h$, —S(=O)$_2$N($R^a$)C(=O)O$R^g$, —S(=O)$_2$N($R^g$)C (=O)N$R^aR^h$, —S(=O)$_2$N($R^a$)C(=O)N$R^aR^g$, —N$R^aR^g$, —N($R^g$)C(=O)$R^e$, —N($R^a$)C(=O)$R^g$, —N($R^g$)C(=O)O$R^h$, —N($R^a$)C(=O)O$R^g$, —N($R^g$)C (=O)N$R^aR^h$, —N($R^a$)C(=O)N$R^aR^g$, —N($R^g$)C (=N$R^a$)N$R^aR^h$, —N($R^a$)C(=N$R^a$)N$R^aR^g$, —N($R^g$)S (=O)$_2R^e$, —N($R^a$)S(=O)$_2R^g$, —N($R^g$)S(=O)$_2$ N$R^aR^h$, —N($R^a$)S(=O)$_2$N$R^aR^g$, —NR$^hC_{2-6}$alkylN$R^aR^g$, —NR$^aC_{2-6}$alkylN$R^aR^g$, —NR$^gC_{2-6}$alkylO$R^h$ and —NR$^aC_{2-6}$alkylO$R^g$.

10. A compound according to claim 2, wherein
$R^4$ is pyridine substituted by 1, 2 or 3 substituents selected from —CH$_2$OH, halo, or $C_{1-4}$haloalkyl.

11. A compound according to claim 2, wherein $R^2$ is —C(=O)$R^g$, —C(=O)$R^b$, —C(=O)O$R^b$, —C(=O)$R^e$, —C(=O)O$R^g$, —C(=O)N$R^aR^a$, —C(=O)N$R^aR^e$, —C(=O)N$R^aR^g$, —C(=N$R^a$)N$R^aR^e$, —(=N$R^a$)N$R^aR^g$, —O$R^a$, —O$R^e$, —O$R^g$, —OC(=O)$R^b$, —OC(=O)$R^e$, —OC(=O)$R^g$, —OC(=O)N$R^aR^a$, —OC(=O)N$R^aR^e$, —OC(=O)N$R^aR^g$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, N$R^aR^e$, N$R^aR^g$, —N($R^a$)C(=O)$R^b$, —N($R^a$)C(=O)$R^e$, —N($R^a$)C(=O)$R^g$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —NR$^cC_{2-6}$alkylNR$^aR^a$ or —NR$^aC_{2-6}$alkylO$R^a$.

* * * * *

UNITED STATES PATENT AND TRADEMARK OFFICE
CERTIFICATE OF CORRECTION

PATENT NO. : 7,439,360 B2  
APPLICATION NO. : 11/251445  
DATED : October 21, 2008  
INVENTOR(S) : Gore et al.

It is certified that error appears in the above-identified patent and that said Letters Patent is hereby corrected as shown below:

Column 90 line 10 change "fromBr" to read --from Br--.

Column 92 line 19 change "sustituted" to read --substituted--.

Column 93 line 42 change "selected" to read --is selected--.

Column 95 line 7 add this missing segment at line 7 --1-(5-methyl-4-(4-(trifluoromethyl)phenyl)-1H-imidazol-2-yl)-4-(3-(trifluoromethyl)-2-pyridinyl)piperazine;--.

Column 97 line 29 change "4-1-1-1,3,4" to read --4H-1,3,4--.

Signed and Sealed this

Twenty-third Day of June, 2009

JOHN DOLL  
*Acting Director of the United States Patent and Trademark Office*